United States Patent
Blair et al.

(10) Patent No.: US 9,730,850 B2
(45) Date of Patent: Aug. 15, 2017

(54) METHOD AND APPARATUS TO DETECT TRANSPONDER TAGGED OBJECTS, FOR EXAMPLE DURING MEDICAL PROCEDURES

(71) Applicant: RF Surgical Systems, Inc., Bellevue, WA (US)

(72) Inventors: William A. Blair, San Diego, CA (US); Bruce E. Barnes, Escondido, CA (US); David A. Poirier, Escondido, CA (US)

(73) Assignee: Covidien LP, Mansfield, MA (US)

( * ) Notice: Subject to any disclaimer, the term of this patent is extended or adjusted under 35 U.S.C. 154(b) by 325 days.

(21) Appl. No.: 14/531,932

(22) Filed: Nov. 3, 2014

(65) Prior Publication Data
US 2015/0054625 A1 Feb. 26, 2015

Related U.S. Application Data

(63) Continuation of application No. 13/462,734, filed on May 2, 2012, now Pat. No. 8,878,668, which is a
(Continued)

(51) Int. Cl.
*A61G 13/10* (2006.01)
*H01Q 21/00* (2006.01)
(Continued)

(52) U.S. Cl.
CPC ............... *A61G 13/10* (2013.01); *A61B 90/90* (2016.02); *A61B 90/98* (2016.02); *G06K 7/0008* (2013.01);
(Continued)

(58) Field of Classification Search
CPC ........ A61B 5/447; A61B 5/455; A61G 13/10; H01Q 5/00; H01Q 21/00; H01Q 21/06; H01Q 21/08; H01Q 21/10; H01Q 21/12
See application file for complete search history.

(56) References Cited

U.S. PATENT DOCUMENTS 2,740,405 A 4/1956 Riordan
3,031,864 A 5/1962 Freundlich
(Continued)

FOREIGN PATENT DOCUMENTS

AU 199852698 B2 3/1993
AU 2003249257 A1 2/2004
(Continued)

OTHER PUBLICATIONS

Extended European Search Report dated Jun. 24, 2016, for corresponding EP Application No. 16151391.6-1659, 8 pages.
(Continued)

*Primary Examiner* — Brian Zimmerman
*Assistant Examiner* — Sara Samson

(57) ABSTRACT

The presence or absence of objects (e.g., medical implements, medical supplies) tagged with transponders may be determined in an environment in which medical procedures (e.g., surgery) are performed via an interrogation and detection system which includes a controller and a plurality of antennas positioned along a patient support structure. The antennas may, for example, be positioned along an operating table, bed, a mattress or pad or a sheet and may be radiolucent. Respective antennas may successively be activated to transmit interrogation signals. Multiple antennas may be monitored for responses from transponders to the interrogation signals. For example, all antennas other than the antenna that transmitted the most recent interrogation signal may be monitored.

15 Claims, 41 Drawing Sheets

Related U.S. Application Data continuation of application No. 12/606,688, filed on Oct. 27, 2009, now Pat. No. 8,264,342.

(60) Provisional application No. 61/109,104, filed on Oct. 28, 2008, provisional application No. 61/222,443, filed on Jul. 1, 2009, provisional application No. 61/242,704, filed on Sep. 15, 2009.

(51) Int. Cl.

| | | |
|---|---|---|
| *H01Q 5/00* | (2015.01) | |
| *H01Q 7/00* | (2006.01) | |
| *G06K 7/00* | (2006.01) | |
| *G06K 7/10* | (2006.01) | |
| *A61B 90/90* | (2016.01) | |
| *A61B 90/98* | (2016.01) | |
| *A61G 13/12* | (2006.01) | |

(52) U.S. Cl.
CPC ..... *G06K 7/10079* (2013.01); *G06K 7/10128* (2013.01); *H01Q 5/00* (2013.01); *H01Q 7/00* (2013.01); *H01Q 21/00* (2013.01); *A61G 13/127* (2013.01); *A61G 13/1265* (2013.01)

(56) References Cited

U.S. PATENT DOCUMENTS

| | | |
|---|---|---|
| 3,422,816 A | 1/1969 | Robinson et al. |
| 3,587,583 A | 6/1971 | Greenberg |
| 3,717,876 A | 2/1973 | Volkers et al. |
| 3,783,282 A | 1/1974 | Hoppenstein |
| D240,166 S | 6/1976 | Cartmell et al. |
| 3,984,695 A | 10/1976 | Collica et al. |
| 4,034,297 A | 7/1977 | Giorgi et al. |
| 4,114,601 A | 9/1978 | Abels |
| 4,193,405 A | 3/1980 | Abels |
| 4,355,317 A | 10/1982 | Muzio |
| 4,422,548 A | 12/1983 | Cheesman et al. |
| D272,943 S | 3/1984 | Stone et al. |
| 4,477,256 A | 10/1984 | Hirsch |
| 4,540,398 A | 9/1985 | Barson et al. |
| 4,603,074 A | 7/1986 | Pate et al. |
| 4,626,251 A | 12/1986 | Shen |
| 4,636,208 A | 1/1987 | Rath |
| 4,639,253 A | 1/1987 | Dyer et al. |
| 4,645,499 A | 2/1987 | Rupinskas |
| 4,658,818 A | 4/1987 | Miller, Jr. et al. |
| 4,681,111 A | 7/1987 | Silvian |
| 4,704,109 A | 11/1987 | Rupinskas |
| 4,718,897 A | 1/1988 | Elves |
| 4,788,730 A | 12/1988 | Bexton |
| 4,893,118 A | 1/1990 | Lewiner et al. |
| 4,917,694 A | 4/1990 | Jessup |
| 4,935,019 A | 6/1990 | Papp, Jr. |
| 4,938,901 A | 7/1990 | Groitzsch et al. |
| 4,966,595 A | 10/1990 | Meringola |
| 4,991,585 A | 2/1991 | Mawhinney |
| 4,992,675 A | 2/1991 | Conner, Jr. et al. |
| 5,031,642 A | 7/1991 | Nosek |
| 5,041,103 A | 8/1991 | Rupinskas |
| 5,045,080 A | 9/1991 | Dyer et al. |
| 5,049,219 A | 9/1991 | Johns et al. |
| 5,057,095 A | 10/1991 | Fabian |
| 5,105,829 A | 4/1992 | Fabian et al. |
| 5,107,862 A | 4/1992 | Fabian et al. |
| 5,112,325 A | 5/1992 | Zachry |
| 5,131,103 A | 7/1992 | Thomas et al. |
| D330,872 S | 11/1992 | Ball |
| 5,181,021 A | 1/1993 | Lee et al. |
| 5,188,126 A | 2/1993 | Fabian et al. |
| 5,190,059 A | 3/1993 | Fabian et al. |
| 5,203,767 A | 4/1993 | Cloyd |
| 5,224,593 A | 7/1993 | Bennett |
| 5,231,273 A | 7/1993 | Caswell et al. |
| 5,235,326 A | 8/1993 | Beigel et al. |
| 5,258,742 A | 11/1993 | Soldevila Domingo et al. |
| 5,281,941 A | 1/1994 | Bernstein |
| 5,329,944 A | 7/1994 | Fabian et al. |
| 5,353,011 A | 10/1994 | Wheeler et al. |
| D353,343 S | 12/1994 | Eberhardt |
| D354,927 S | 1/1995 | Andrau |
| 5,390,360 A | 2/1995 | Scop et al. |
| D356,052 S | 3/1995 | Andrau |
| D359,705 S | 6/1995 | Ball |
| 5,437,653 A | 8/1995 | Gilman et al. |
| 5,446,447 A | 8/1995 | Carney et al. |
| 5,450,622 A | 9/1995 | Vandegraaf |
| 5,456,718 A | 10/1995 | Szymaitis |
| 5,482,036 A | 1/1996 | Diab et al. |
| 5,557,279 A | 9/1996 | D'Hont |
| 5,575,781 A | 11/1996 | DeBusk |
| D378,614 S | 3/1997 | Jensen |
| 5,629,498 A | 5/1997 | Pollock et al. |
| 5,650,596 A | 7/1997 | Morris et al. |
| 5,664,582 A | 9/1997 | Szymaitis |
| D385,037 S | 10/1997 | Jensen |
| 5,678,569 A | 10/1997 | Chew et al. |
| 5,725,517 A | 3/1998 | DeBusk |
| 5,767,816 A | 6/1998 | Cosman |
| 5,792,128 A | 8/1998 | DeBusk |
| D412,135 S | 7/1999 | Saito |
| 5,923,001 A | 7/1999 | Morris et al. |
| 5,928,151 A | 7/1999 | Hossack et al. |
| 5,931,824 A | 8/1999 | Stewart et al. |
| 5,963,132 A | 10/1999 | Yoakum |
| 5,969,613 A | 10/1999 | Yeager et al. |
| D418,773 S | 1/2000 | Saito |
| 6,026,818 A | 2/2000 | Blair et al. |
| D423,673 S | 4/2000 | Bassøe |
| 6,073,284 A | 6/2000 | Borders |
| 6,075,797 A | 6/2000 | Thomas |
| 6,093,869 A | 7/2000 | Roe et al. |
| D429,337 S | 8/2000 | Sanfilippo |
| 6,172,608 B1 | 1/2001 | Cole |
| 6,201,469 B1 | 3/2001 | Balch et al. |
| 6,211,666 B1 | 4/2001 | Acker |
| 6,215,437 B1 | 4/2001 | Schürmann et al. |
| 6,223,137 B1 | 4/2001 | McCay et al. |
| 6,232,878 B1 | 5/2001 | Rubin |
| 6,270,460 B1 | 8/2001 | McCartan et al. |
| 6,276,033 B1 | 8/2001 | Johnson et al. |
| 6,287,253 B1* | 9/2001 | Ortega ................. A61B 5/0051 |
| | | 128/897 |
| 6,295,671 B1 | 10/2001 | Reesby et al. |
| 6,317,027 B1 | 11/2001 | Watkins |
| 6,349,234 B2 | 2/2002 | Pauly et al. |
| 6,353,406 B1 | 3/2002 | Lanzl et al. |
| 6,354,493 B1 | 3/2002 | Mon |
| 6,359,562 B2 | 3/2002 | Rubin |
| 6,366,206 B1 | 4/2002 | Ishikawa et al. |
| 6,378,149 B1 | 4/2002 | Sanders et al. |
| D456,907 S | 5/2002 | Sanfilippo |
| D457,634 S | 5/2002 | Rouns et al. |
| 6,384,296 B1 | 5/2002 | Roe et al. |
| 6,401,283 B2 | 6/2002 | Thomas et al. |
| 6,401,722 B1 | 6/2002 | Krag |
| 6,441,741 B1 | 8/2002 | Yoakum |
| D471,281 S | 3/2003 | Baura et al. |
| 6,557,752 B1 | 5/2003 | Yacoob |
| 6,566,997 B1 | 5/2003 | Bradin |
| 6,578,219 B1 | 6/2003 | Gabel et al. |
| 6,588,661 B2 | 7/2003 | Degrauwe et al. |
| 6,599,448 B1 | 7/2003 | Ehrhard, Jr. et al. |
| 6,620,187 B2 | 9/2003 | Carson et al. |
| 6,632,216 B2 | 10/2003 | Houzego et al. |
| 6,633,226 B1 | 10/2003 | Nysen |
| 6,641,039 B2 | 11/2003 | Southard |
| 6,645,232 B2 | 11/2003 | Carson |
| 6,648,223 B2 | 11/2003 | Boukhny et al. |
| 6,648,905 B2 | 11/2003 | Hoglund et al. |
| 6,650,143 B1 | 11/2003 | Peng |
| 6,650,240 B2 | 11/2003 | Lee et al. |
| 6,653,607 B2 | 11/2003 | Ellis et al. |

(56) References Cited

U.S. PATENT DOCUMENTS

| | | |
|---|---|---|
| 6,654,629 B2 | 11/2003 | Montegrande |
| 6,660,027 B2 | 12/2003 | Gruszecki et al. |
| 6,667,902 B2 | 12/2003 | Peng |
| 6,669,715 B2 | 12/2003 | Hoglund et al. |
| 6,671,040 B2 | 12/2003 | Fong et al. |
| 6,692,518 B2 | 2/2004 | Carson |
| 6,696,954 B2 | 2/2004 | Chung |
| 6,699,267 B2 | 3/2004 | Voorhees et al. |
| 6,700,151 B2 | 3/2004 | Peng |
| 6,722,783 B2 | 4/2004 | Jackson, Sr. |
| 6,734,795 B2 | 5/2004 | Price |
| 6,744,378 B1 | 6/2004 | Tyburski |
| 6,753,783 B2 * | 6/2004 | Friedman ............ A61B 5/0002 324/207.11 |
| 6,766,960 B2 | 7/2004 | Peng |
| D495,055 S | 8/2004 | Silber |
| 6,774,800 B2 | 8/2004 | Friedman et al. |
| 6,777,623 B2 | 8/2004 | Ballard |
| 6,777,757 B2 | 8/2004 | Peng et al. |
| 6,778,089 B2 | 8/2004 | Yoakum |
| 6,786,405 B2 | 9/2004 | Wiedenhoefer |
| 6,791,891 B1 | 9/2004 | Peng et al. |
| 6,798,693 B2 | 9/2004 | Peng |
| 6,799,063 B2 | 9/2004 | Carson |
| 6,811,113 B1 | 11/2004 | Silansky et al. |
| 6,812,824 B1 | 11/2004 | Goldinger et al. |
| 6,812,842 B2 | 11/2004 | Dimmer |
| 6,814,889 B1 | 11/2004 | O'Grady et al. |
| 6,822,570 B2 | 11/2004 | Dimmer et al. |
| 6,822,888 B2 | 11/2004 | Peng |
| 6,832,398 B2 | 12/2004 | Borders et al. |
| 6,838,990 B2 | 1/2005 | Dimmer |
| 6,856,540 B2 | 2/2005 | Peng et al. |
| D502,419 S | 3/2005 | Copen |
| 6,861,639 B2 | 3/2005 | Al-Ali |
| 6,861,954 B2 | 3/2005 | Levin |
| 6,879,300 B2 | 4/2005 | Rochelle et al. |
| 6,898,116 B2 | 5/2005 | Peng |
| 6,903,656 B1 | 6/2005 | Lee |
| 6,909,366 B1 | 6/2005 | Marsh et al. |
| 6,912,749 B2 | 7/2005 | Thomas et al. |
| 6,918,144 B2 | 7/2005 | Friedman |
| 6,924,467 B2 | 8/2005 | Ellis et al. |
| 6,933,469 B2 | 8/2005 | Ellis et al. |
| 6,940,751 B2 | 9/2005 | Peng et al. |
| D511,004 S | 10/2005 | Masuda |
| 6,951,305 B2 | 10/2005 | Overhultz et al. |
| 6,956,258 B2 | 10/2005 | Peng |
| D511,384 S | 11/2005 | Masuda |
| 6,967,309 B2 | 11/2005 | Wyatt et al. |
| 6,972,986 B2 | 12/2005 | Peng et al. |
| 6,974,935 B2 | 12/2005 | O'Grady |
| 6,977,504 B2 | 12/2005 | Wright et al. |
| 6,988,284 B2 | 1/2006 | Bannister |
| 6,992,925 B2 | 1/2006 | Peng |
| 6,998,541 B2 | 2/2006 | Morris et al. |
| 7,001,366 B2 | 2/2006 | Ballard |
| 7,019,650 B2 | 3/2006 | Volpi et al. |
| 7,020,917 B1 | 4/2006 | Kolody et al. |
| 7,026,924 B2 | 4/2006 | Degrauwe et al. |
| 7,026,927 B2 | 4/2006 | Wright et al. |
| 7,031,209 B2 | 4/2006 | Wang et al. |
| 7,037,336 B2 | 5/2006 | Ward |
| 7,042,722 B2 | 5/2006 | Suzuki et al. |
| 7,071,791 B1 | 7/2006 | Wilson, III |
| D526,586 S | 8/2006 | McCaghren et al. |
| 7,098,793 B2 | 8/2006 | Chung |
| 7,098,866 B2 | 8/2006 | Desjeux et al. |
| 7,118,029 B2 | 10/2006 | Nycz et al. |
| 7,135,973 B2 | 11/2006 | Kittel et al. |
| 7,135,978 B2 | 11/2006 | Gisselberg et al. |
| 7,142,118 B2 | 11/2006 | Hamilton et al. |
| 7,142,815 B2 | 11/2006 | Desjeux et al. |
| D534,448 S | 1/2007 | Shaffer, II et al. |
| 7,158,030 B2 | 1/2007 | Chung |
| 7,158,754 B2 | 1/2007 | Anderson |
| 7,159,832 B2 | 1/2007 | Easterling |
| 7,160,258 B2 | 1/2007 | Imran et al. |
| D536,673 S | 2/2007 | Silber |
| 7,176,419 B2 | 2/2007 | Ellis et al. |
| 7,176,798 B2 | 2/2007 | Dimmer et al. |
| 7,183,914 B2 | 2/2007 | Norman et al. |
| 7,183,927 B2 | 2/2007 | Kolton et al. |
| 7,196,289 B2 | 3/2007 | Ellis et al. |
| 7,227,469 B2 | 6/2007 | Varner et al. |
| 7,245,893 B1 | 7/2007 | Husted et al. |
| 7,256,695 B2 | 8/2007 | Hamel et al. |
| 7,256,696 B2 | 8/2007 | Levin |
| 7,268,684 B2 | 9/2007 | Tethrake et al. |
| 7,269,047 B1 | 9/2007 | Fong et al. |
| 7,299,981 B2 | 11/2007 | Hickle et al. |
| D557,421 S | 12/2007 | Fleck et al. |
| D557,423 S | 12/2007 | Chen |
| D558,352 S | 12/2007 | Sanfilippo |
| 7,307,530 B2 | 12/2007 | Fabian et al. |
| D558,882 S | 1/2008 | Brady |
| 7,319,396 B2 | 1/2008 | Homanfar et al. |
| 7,319,397 B2 | 1/2008 | Chung et al. |
| 7,319,398 B2 | 1/2008 | Marino |
| 7,325,723 B2 | 2/2008 | Desjeux |
| 7,333,013 B2 | 2/2008 | Berger |
| 7,342,497 B2 | 3/2008 | Chung et al. |
| 7,362,228 B2 | 4/2008 | Nycz et al. |
| D568,186 S | 5/2008 | Blair et al. |
| 7,378,975 B1 * | 5/2008 | Smith ................ A61B 5/1126 340/573.1 |
| 7,382,255 B2 | 6/2008 | Chung |
| 7,397,364 B2 | 7/2008 | Govari |
| 7,399,899 B2 | 7/2008 | Fabian |
| 7,408,168 B1 | 8/2008 | Aufrichtig et al. |
| 7,420,468 B2 | 9/2008 | Fabian et al. |
| 7,423,535 B2 | 9/2008 | Chung et al. |
| 7,446,646 B2 | 11/2008 | Huomo |
| 7,449,614 B2 | 11/2008 | Ales, III |
| 7,464,713 B2 | 12/2008 | Fabian et al. |
| 7,465,847 B2 | 12/2008 | Fabian |
| 7,471,541 B2 | 12/2008 | Fong et al. |
| D584,414 S | 1/2009 | Lash et al. |
| 7,474,222 B2 | 1/2009 | Yang et al. |
| 7,480,950 B2 | 1/2009 | Feher |
| 7,492,257 B2 | 2/2009 | Tethrake et al. |
| 7,492,261 B2 | 2/2009 | Cambre et al. |
| 7,492,263 B2 | 2/2009 | Marsilio et al. |
| 7,508,308 B2 | 3/2009 | Chung |
| D590,342 S | 4/2009 | Dávila et al. |
| 7,513,425 B2 | 4/2009 | Chung |
| 7,557,710 B2 | 7/2009 | Sanchez et al. |
| D598,110 S | 8/2009 | Phillips et al. |
| D598,114 S | 8/2009 | Cryan |
| 7,589,634 B2 | 9/2009 | Frank |
| 7,609,538 B1 | 10/2009 | Lee et al. |
| 7,644,016 B2 | 1/2010 | Nycz et al. |
| 7,663,076 B2 | 2/2010 | Tarry |
| 7,696,877 B2 | 4/2010 | Barnes et al. |
| 7,769,422 B2 | 8/2010 | DiSilvestro et al. |
| 7,770,473 B2 | 8/2010 | Von Lilienfeld-Toal et al. |
| 7,795,491 B2 | 9/2010 | Stewart et al. |
| 7,855,656 B2 | 12/2010 | Maschke |
| 7,876,097 B2 | 1/2011 | Greim |
| 7,898,420 B2 | 3/2011 | Blair et al. |
| 7,909,861 B2 | 3/2011 | Balachandran et al. |
| 7,937,789 B2 | 5/2011 | Feher |
| 8,082,192 B2 | 12/2011 | Nycz et al. |
| 8,105,296 B2 | 1/2012 | Morris et al. |
| 8,111,162 B2 | 2/2012 | Barnes et al. |
| 8,193,938 B2 | 6/2012 | Halberthal et al. |
| 8,256,674 B2 | 9/2012 | Fleck et al. |
| 8,259,518 B2 | 9/2012 | Peng et al. |
| 8,279,068 B2 | 10/2012 | Morris et al. |
| 8,319,612 B2 | 11/2012 | Borcherding |
| 8,323,189 B2 | 12/2012 | Tran et al. |
| 8,371,448 B1 | 2/2013 | Reaux |
| 8,454,613 B2 | 6/2013 | Tethrake et al. |
| 8,477,076 B1 | 7/2013 | Nero, Jr. et al. |

(56) References Cited

U.S. PATENT DOCUMENTS

| | | |
|---|---|---|
| 8,477,077 B1 | 7/2013 | Nero, Jr. et al. |
| 8,479,989 B2 | 7/2013 | Fleck et al. |
| 8,535,246 B2 * | 9/2013 | Drennan ............... A61B 5/103 600/587 |
| 8,576,076 B2 | 11/2013 | Morris et al. |
| 8,780,660 B2 | 7/2014 | Peng |
| 8,872,662 B2 | 10/2014 | Halberthal et al. |
| 8,878,668 B2 | 11/2014 | Blair et al. |
| 8,937,575 B2 | 1/2015 | Ward et al. |
| 8,985,446 B2 | 3/2015 | Fleck et al. |
| 9,168,104 B2 | 10/2015 | Dein |
| 9,317,795 B2 * | 4/2016 | Forster ............... G06K 19/0717 |
| 9,414,973 B2 | 8/2016 | Fleck et al. |
| 2001/0030610 A1 | 10/2001 | Rochelle et al. |
| 2002/0011932 A1 | 1/2002 | Rodgers et al. |
| 2002/0032435 A1 | 3/2002 | Levin |
| 2002/0070863 A1 | 6/2002 | Brooking |
| 2002/0143320 A1 | 10/2002 | Levin |
| 2002/0165587 A1 | 11/2002 | Zhang et al. |
| 2002/0188259 A1 | 12/2002 | Hickle et al. |
| 2003/0004411 A1 | 1/2003 | Govari et al. |
| 2003/0052788 A1 | 3/2003 | Kwong-Tai Chung |
| 2003/0105394 A1 | 6/2003 | Fabian et al. |
| 2003/0111592 A1 | 6/2003 | Al-Ali |
| 2003/0175473 A1 | 9/2003 | Gillum et al. |
| 2003/0199624 A1 | 10/2003 | Yadav et al. |
| 2004/0008123 A1 | 1/2004 | Carrender et al. |
| 2004/0030372 A1 | 2/2004 | Ellingboe et al. |
| 2004/0030373 A1 | 2/2004 | Ellingboe et al. |
| 2004/0129279 A1 | 7/2004 | Fabian et al. |
| 2004/0137844 A1 | 7/2004 | Desjeux et al. |
| 2004/0138554 A1 | 7/2004 | Dimmer et al. |
| 2004/0250819 A1 | 12/2004 | Blair et al. |
| 2004/0254420 A1 | 12/2004 | Ward |
| 2005/0110640 A1 | 5/2005 | Chung |
| 2005/0131397 A1 | 6/2005 | Levin |
| 2005/0154293 A1 | 7/2005 | Gisselberg et al. |
| 2005/0154336 A1 | 7/2005 | Kloecker et al. |
| 2005/0201450 A1 | 9/2005 | Volpi et al. |
| 2005/0203470 A1 | 9/2005 | Ballard |
| 2005/0212673 A1 | 9/2005 | Forster |
| 2005/0247794 A1 | 11/2005 | Jones et al. |
| 2005/0249036 A1 | 11/2005 | Davies et al. |
| 2005/0267550 A1 | 12/2005 | Hess et al. |
| 2006/0010607 A1 | 1/2006 | Schneider |
| 2006/0047238 A1 | 3/2006 | Galdenzi et al. |
| 2006/0052851 A1 | 3/2006 | Anderson et al. |
| 2006/0055537 A1 | 3/2006 | Jackson |
| 2006/0065060 A1 * | 3/2006 | Ito ..................... A61B 5/103 73/862.046 |
| 2006/0084934 A1 | 4/2006 | Frank |
| 2006/0106368 A1 | 5/2006 | Miller et al. |
| 2006/0109086 A1 | 5/2006 | Amtmann |
| 2006/0163350 A1 | 7/2006 | Melton et al. |
| 2006/0187044 A1 | 8/2006 | Fabian et al. |
| 2006/0194899 A1 | 8/2006 | Ohashi et al. |
| 2006/0202827 A1 | 9/2006 | Volpi et al. |
| 2006/0212102 A1 | 9/2006 | Frey et al. |
| 2006/0232407 A1 | 10/2006 | Ballard |
| 2006/0235488 A1 | 10/2006 | Nycz et al. |
| 2006/0241396 A1 | 10/2006 | Fabian et al. |
| 2006/0241399 A1 | 10/2006 | Fabian |
| 2006/0243720 A1 | 11/2006 | Koch et al. |
| 2006/0244597 A1 | 11/2006 | Tethrake et al. |
| 2006/0244652 A1 | 11/2006 | Tethrake et al. |
| 2006/0270933 A1 | 11/2006 | Benson et al. |
| 2006/0271134 A1 | 11/2006 | Frey |
| 2006/0276864 A1 | 12/2006 | Collins |
| 2007/0004994 A1 | 1/2007 | Sherman |
| 2007/0005141 A1 | 1/2007 | Sherman |
| 2007/0034670 A1 | 2/2007 | Racenet et al. |
| 2007/0035383 A1 | 2/2007 | Roemerman et al. |
| 2007/0038233 A1 | 2/2007 | Martinez et al. |
| 2007/0055109 A1 | 3/2007 | Bass et al. |
| 2007/0069866 A1 | 3/2007 | Schuessler et al. |
| 2007/0109099 A1 | 5/2007 | Raphaeli et al. |
| 2007/0125392 A1 | 6/2007 | Olson, Jr. et al. |
| 2007/0152823 A1 | 7/2007 | Hirahara et al. |
| 2007/0209957 A1 | 9/2007 | Glenn et al. |
| 2007/0213837 A1 | 9/2007 | Ferreri et al. |
| 2007/0216062 A1 | 9/2007 | Frank |
| 2007/0219516 A1 | 9/2007 | Patel et al. |
| 2007/0238982 A1 | 10/2007 | Caylor, III |
| 2007/0239289 A1 | 10/2007 | Cambre et al. |
| 2007/0244470 A1 | 10/2007 | Barker, Jr. et al. |
| 2007/0244532 A1 | 10/2007 | Pierre et al. |
| 2007/0265690 A1 | 11/2007 | Lichtenstein et al. |
| 2007/0270660 A1 | 11/2007 | Caylor, III et al. |
| 2007/0285249 A1 | 12/2007 | Blair et al. |
| 2008/0001760 A1 | 1/2008 | Oh et al. |
| 2008/0007411 A1 | 1/2008 | Levin |
| 2008/0018469 A1 | 1/2008 | Volpi et al. |
| 2008/0020189 A1 | 1/2008 | Hofmair et al. |
| 2008/0021308 A1 | 1/2008 | Dimmer et al. |
| 2008/0024277 A1 | 1/2008 | Volpi et al. |
| 2008/0024281 A1 | 1/2008 | Shimura |
| 2008/0030303 A1 | 2/2008 | Kobren et al. |
| 2008/0051746 A1 | 2/2008 | Shen-Gunther |
| 2008/0058637 A1 | 3/2008 | Fischell et al. |
| 2008/0082092 A1 | 4/2008 | McPherson |
| 2008/0086771 A1 | 4/2008 | Li et al. |
| 2008/0119757 A1 | 5/2008 | Winter |
| 2008/0126122 A1 * | 5/2008 | Warner ................ G06F 19/327 705/2 |
| 2008/0132860 A1 | 6/2008 | Smith et al. |
| 2008/0161891 A1 | 7/2008 | Pierre et al. |
| 2008/0204245 A1 | 8/2008 | Blair et al. |
| 2008/0228248 A1 | 9/2008 | Guyuron et al. |
| 2008/0231452 A1 | 9/2008 | Levin |
| 2008/0237341 A1 | 10/2008 | Fleck et al. |
| 2008/0243404 A1 | 10/2008 | Banhegyesi |
| 2008/0244830 A1 | 10/2008 | Davis |
| 2008/0249520 A1 | 10/2008 | Dunning et al. |
| 2008/0249521 A1 | 10/2008 | Dunning et al. |
| 2008/0249524 A1 | 10/2008 | Dunning |
| 2008/0272913 A1 | 11/2008 | Barnes et al. |
| 2008/0281190 A1 | 11/2008 | Petcavich et al. |
| 2008/0284570 A1 | 11/2008 | Ryoo et al. |
| 2008/0296373 A1 | 12/2008 | Zmood et al. |
| 2009/0000614 A1 | 1/2009 | Carrano |
| 2009/0008449 A1 | 1/2009 | Qing et al. |
| 2009/0014518 A1 | 1/2009 | Stewart et al. |
| 2009/0051485 A1 | 2/2009 | Corry et al. |
| 2009/0110022 A1 | 4/2009 | Snyder et al. |
| 2009/0132008 A1 | 5/2009 | Snitting et al. |
| 2009/0228082 A1 | 9/2009 | Ross, III et al. |
| 2009/0248120 A1 | 10/2009 | Starr et al. |
| 2009/0267765 A1 | 10/2009 | Greene et al. |
| 2009/0315681 A1 | 12/2009 | Blair |
| 2009/0322485 A1 | 12/2009 | Barnes et al. |
| 2010/0033309 A1 | 2/2010 | Blair |
| 2010/0057170 A1 | 3/2010 | Robinson et al. |
| 2010/0108079 A1 | 5/2010 | Blair |
| 2010/0109848 A1 | 5/2010 | Blair et al. |
| 2010/0137704 A1 | 6/2010 | Vij et al. |
| 2010/0198320 A1 | 8/2010 | Pierre et al. |
| 2010/0204763 A1 | 8/2010 | Augustine et al. |
| 2010/0211138 A1 | 8/2010 | Pierre et al. |
| 2010/0211139 A1 | 8/2010 | Pierre et al. |
| 2010/0211141 A1 | 8/2010 | Pierre et al. |
| 2010/0241073 A1 | 9/2010 | Andersen et al. |
| 2010/0324433 A1 | 12/2010 | Wilson et al. |
| 2011/0004276 A1 | 1/2011 | Blair et al. |
| 2011/0011939 A1 | 1/2011 | Seah |
| 2011/0056017 A1 | 3/2011 | Schreiber et al. |
| 2011/0063078 A1 | 3/2011 | Souma |
| 2011/0098794 A1 | 4/2011 | Anderson et al. |
| 2011/0181394 A1 | 7/2011 | Blair |
| 2011/0277359 A1 | 11/2011 | Halberthal et al. |
| 2011/0304315 A1 | 12/2011 | McElhinny et al. |
| 2012/0031547 A1 | 2/2012 | Halberthal et al. |
| 2012/0116499 A1 | 5/2012 | Goetzen et al. |
| 2012/0139706 A1 | 6/2012 | Nero, Jr. et al. |
| 2013/0023225 A1 | 1/2013 | Weber |

(56) References Cited

U.S. PATENT DOCUMENTS

| | | |
|---|---|---|
| 2013/0199720 A1 | 8/2013 | Halberthal et al. |
| 2014/0068915 A1 | 3/2014 | Halberthal et al. |
| 2014/0243770 A1 | 8/2014 | Stewart |
| 2014/0303580 A1 | 10/2014 | Blair |
| 2015/0054625 A1 | 2/2015 | Blair et al. |
| 2015/0115121 A1 | 4/2015 | Blair |
| 2015/0164603 A1 | 6/2015 | Fleck et al. |
| 2015/0216610 A1 | 8/2015 | Augustine |
| 2015/0272688 A1 | 10/2015 | Blair et al. |
| 2015/0317555 A1 | 11/2015 | Dor et al. |
| 2016/0157957 A1 | 6/2016 | Blair |
| 2016/0206399 A1 | 7/2016 | Blair |
| 2016/0210548 A1 | 7/2016 | Blair |
| 2016/0259954 A1 | 9/2016 | Buhler et al. |
| 2016/0294040 A1 | 10/2016 | Blair |

FOREIGN PATENT DOCUMENTS

| | | |
|---|---|---|
| CN | 2865741 Y | 2/2007 |
| CN | 101460096 A | 6/2009 |
| EP | 1 612 554 A1 | 1/2006 |
| EP | 2 087 850 A2 | 8/2009 |
| JP | 2009539478 A | 11/2009 |
| WO | 86/02539 A1 | 5/1986 |
| WO | 02/39917 A1 | 5/2002 |
| WO | 03/073934 A1 | 9/2003 |
| WO | 2004/008387 A1 | 1/2004 |
| WO | 2004/054801 A1 | 7/2004 |
| WO | 2004/078039 A1 | 9/2004 |
| WO | 2004/086997 A1 | 10/2004 |
| WO | 2006/060781 A1 | 6/2006 |
| WO | 2007/024348 A2 | 3/2007 |
| WO | 2007/120736 A2 | 10/2007 |
| WO | 2007/146091 A1 | 12/2007 |
| WO | 2008/008449 A2 | 1/2008 |
| WO | 2008/024921 A1 | 2/2008 |
| WO | 2008/106552 A1 | 9/2008 |
| WO | 2008/112709 A1 | 9/2008 |
| WO | 2008/133634 A1 | 11/2008 |
| WO | 2009/151946 A1 | 12/2009 |
| WO | 2009/154987 A1 | 12/2009 |
| WO | 2012/125916 A2 | 9/2012 |
| WO | 2014/176072 A1 | 10/2014 |

OTHER PUBLICATIONS

International Search Report, mailed Mar. 24, 2015, for PCT/US2014/070547, 3 pages.
Black, "Method and Apparatus to Account for Transponder Tagged Objects During Clinical Procedures, Employing a Trocar," U.S. Appl. No. 62/360,869, filed Jul. 11, 2016, 99 pages.
Black, "Method and Apparatus to Account for Transponder Tagged Objects Used During Clinical Procedures, Employing a Trocar," U.S. Appl. No. 62/378,515, filed Aug. 23, 2016, 103 pages.
Extended European Search Report, dated Aug. 18, 2016, for corresponding European Application No. 16163825.9, 15 pages.
Extended European Search Report, dated Jul. 14, 2016, for corresponding European Application No. 16158315.8, 7 pages.
Giancoli, "Table of Resistivity," dated Mar. 14, 2014, retrieved from http://moodle1315.up.pt/pluginfile.php/167900/mod_resource/content/1/Resistivity%20and%20Temperature%20Coefficent%20at%2020%20C%20.pdf on Jul. 27, 2016, 1 page.
Haldor Advanced Technologies, "Haldor Advanced Technologies Releases a Breakthrough New Sponge Management Solution: Modular, Mobile, Wireless, and Tailored per Use-case and Requirements," Sep. 8, 2015, retrieved from http://ww1.prweb.com/prfiles/2015/09/06/12938762/ORLocate%205Sponge%20Solution-September%202015.pdf, 2 pages.
Hansen et al., "Method and Apparatus to Account for Transponder Tagged Objects Used During Clinical Procedures, Employing a Shielded Receptacle," U.S. Appl. No. 62/360,864, filed Jul. 11, 2016, 99 pages.
Hansen et al., "Method and Apparatus to Account for Transponder Tagged Objects Used During Clinical Procedures Employing a Shielded Receptacle With Antenna," U.S. Appl. No. 62/360,866, filed Jul. 11, 2016, 154 pages.
Poirier et al., "Method and Apparatus to Account for Transponder Tagged Objects Used During Clinical Procedures, for Example Including Count In and/or Count Out and Presence Detection," U.S. Appl. No. 62/360,868, filed Jul. 11, 2016, 113 pages.
Poirier et al., "Method and Apparatus to Account for Transponder Tagged Objects Used During Clinical Procedures, for Example Including Count In and/or Count Out and Presence Detection," U.S. Appl. No. 62/378,511, filed Aug. 23, 2016, 114 pages.
Reza et al., "RFID Transponder Collision Control Algorithm," *Wireless Pers. Commun.* 59:689-711, 2011.
Barnes et al., "Design for a FET based 1 MHz, 10kV Pulse Generator," Pulsed Power Conference, Digest of Technical Papers, Tenth IEEE International, 2:1335-1340, 1995.
Clearcount Medical Solutions, "The SmartSponge System," Downloaded from http://clearcount.com on Oct. 20, 2009, 7 pages.
Macario et al., "Initial Clinical Evaluation of a Handheld Device for Detecting Retained Surgical Gauze Sponges Using Radiofrequency Identification Technology," Arch Surg 141:659-662, Jul. 2006.
Inditherm, Patient Warming—Technology, URL=http://www.inditherm.com/default.asp?ContentID=70, download date Jun. 9, 2011.
Inditherm, SpeedHeat—Features and Benefits, URL=http://www.inditherm.com/default.asp?contentid=75, download date Jun. 9, 2011.
Inditherm, Therapeutic Heating (SpeedHeat), URL=http://www.inditherm.com/default.asp?contentid=74, download date Jun. 9, 2011.
Inditherm, Inditherm Medical, URL=http://www.inditherm.com/default.asp?chapterid=4&langid=1, download date Jun. 9, 2011.
International Search Report, mailed Jan. 4, 2010, for PCT/US2009/045312, 3 pages.
Written Opinion, mailed Jan. 4, 2010, for PCT/US2009/045312, 3 pages.
Blair et al., "Mat Based Antenna System to Detect Transponder Tagged Objects, for Example During Medical Procedures," U.S. Appl. No. 13/422,192, filed Mar. 16, 2012, 38 pages.
Blair et al., "Tag and Detection Device," U.S. Appl. No. 60/458,222, filed Mar. 27, 2003, 23 pages.
Blair et al., "Improved Apparatus and Method for Detecting Objects Using Tags and Wideband Detection Device," U.S. Appl. No. 60/811,376, filed Jun. 6, 2006, 16 pages.
Blair et al., "Method, Apparatus and Article for Detection of Transponder Tagged Objects, for Example During Surgery," U.S. Appl. No. 60/892,208, filed Feb. 28, 2007, 50 pages.
Blair et al., "Transponder Housing and Device to Mark Implements, Such as Surgical Implements, and Method of Using Same," U.S. Appl. No. 60/894,435, filed Mar. 12, 2007, 30 pages.
Blair, "Apparatus, Method, and Article for Detection and Identification of Multi-Mode Integral Transponder Tagged Objects," U.S. Appl. No. 61/056,229, filed May 27, 2008, 38 pages.
Barnes et al., "Method, Apparatus and Article for Detection of Transponder Tagged Objects, for Example During Surgery," U.S. Appl. No. 61/056,787, filed May 28, 2008, 60 pages.
Blair, "Transponder Device to Mark Implements, Such as Surgical Implements, and Method of Manufacturing and Using Same," U.S. Appl. No. 61/086,727, filed Aug. 6, 2008, 30 pages.
Barnes et al., "Method, Apparatus and Article for Detection of Transponder Tagged Objects, for Example During Surgery," U.S. Appl. No. 61/091,667, filed Aug. 25, 2008, 76 pages.
Blair, "Multi-Modal Transponder and Method and Apparatus to Detect Same," U.S. Appl. No. 61/102,749, filed Oct. 3, 2008, 48 pages.
Blair, "Detectable Surgical Objects and Methods of Making Same," U.S. Appl. No. 61/109,142, filed Oct. 28, 2008, 47 pages.
Blair, "Transponder Device to Mark Implements, Such as Surgical Implements, and Method of Manufacturing and Using Same," U.S. Appl. No. 61/220,452, filed Jun. 25, 2009, 46 pages.
Blair, "Radio Opaque Device with Resonant Nanostructures," U.S. Appl. No. 61/163,813, filed Mar. 26, 2009, 47 pages.

(56) References Cited

OTHER PUBLICATIONS

Blair et al., "Method and Apparatus to Detect Transponder Tagged Objects and to Communicate with Medical Telemetry Devices, for Example During Surgery," U.S. Appl. No. 61/222,847, filed Jul. 2, 2009, 122 pages.

Blair, "Transponder Device to Mark Implements, Such as Surgical Implements, and Method of Manufacturing and Using Same," U.S. Appl. No. 61/224,323, filed Jul. 9, 2009, 57 pages.

Blair et al., "Method and Apparatus to Detect Transponder Tagged Objects and to Communicate with Medical Telemetry Devices, for Example During Medical Procedures," U.S. Appl. No. 61/242,699, filed Sep. 15, 2009, 158 pages.

Blair, "Method and Apparatus to Account for Transponder Tagged Objects Used During Medical Procedures," U.S. Appl. No. 61/263,726, filed Nov. 23, 2009, 78 pages.

Blair et al., "Mat Based Antenna System to Detect Transponder Tagged Objects, for Example During Medical Procedures," U.S. Appl. No. 61/453,846, filed Mar. 17, 2011, 38 pages.

Blair et al., "Method and Apparatus to Detect Transponder Tagged Objects, for Example During Medical Procedures," Office Action mailed Jan. 31, 2012, for U.S. Appl. No. 12/606,688, 34 pages.

Blair et al., "Method and Apparatus to Detect Transponder Tagged Objects, for Example During Medical Procedures," Amendment filed Apr. 27, 2012, for U.S. Appl. No. 12/606,688, 20 pages.

Blair, "Transponder Housing," U.S. Appl. No. 29/322,539, filed Aug. 6, 2008, 6 pages.

Blair, "Attachment Article to Attach a Transponder to a Surgical Sponge," U.S. Appl. No. 29/336,007, filed Apr. 27, 2009, 4 pages.

Blair, "Attachment Article to Attach a Transponder to a Surgical Sponge," U.S. Appl. No. 29/336,008, filed Apr. 27, 2009, 7 pages.

Blair, "Article to Attach a Transponder to a Surgical Sponge," U.S. Appl. No. 29/336,009, filed Apr. 27, 2009, 4 pages.

Blair et al., "Method and Apparatus to Detect Transponder Tagged Objects, for Example During Medical Procedures," Notice of Allowance mailed May 14, 2012, for U.S. Appl. No. 12/606,688, 12 pages.

Blair et al., "Method and Apparatus to Detect Transponder Tagged Objects, for Example During Medical Procedures," Amendment filed May 10, 2012, for U.S. Appl. No. 13/462,734, 7 pages.

Blair et al., "Method and Apparatus to Detect Transponder Tagged Objects, for Example During Medical Procedures," Office Action mailed Aug. 17, 2012, for U.S. Appl. No. 13/462,734, 15 pages.

Blair et al., "Method and Apparatus to Detect Transponder Tagged Objects, for Example During Medical Procedures," Amendment filed Nov. 16, 2012, for U.S. Appl. No. 13/462,734, 33 pages.

Blair et al., "Method and Apparatus to Detect Transponder Tagged Objects, for Example During Medical Procedures," Office Action mailed Jan. 9, 2013, for U.S. Appl. No. 13/462,734, 8 pages.

Blair et al., "Method and Apparatus to Detect Transponder Tagged Objects, for Example During Medical Procedures," Amendment filed May 9, 2013, for U.S. Appl. No. 13/462,734, 10 pages.

Blair et al., "Method and Apparatus to Detect Transponder Tagged Objects, for Example During Medical Procedures," Office Action mailed May 29, 2013, for U.S. Appl. No. 13/462,734, 18 pages.

Blair et al., "Method and Apparatus to Detect Transponder Tagged Objects, for Example During Medical Procedures," Amendment filed Sep. 30, 2012, for U.S. Appl. No. 13/462,734, 13 pages.

Blair et al., "Method and Apparatus to Detect Transponder Tagged Objects, for Example During Medical Procedures," Office Action mailed Jan. 14, 2014, for U.S. Appl. No. 13/462,734, 15 pages.

Blair et al., "Method and Apparatus to Detect Transponder Tagged Objects, for Example During Medical Procedures," Amendment filed Jun. 13, 2014, for U.S. Appl. No. 13/462,734, 9 pages.

Blair et al., "Method and Apparatus to Detect Transponder Tagged Objects, for Example During Medical Procedures," Notice of Allowance mailed Jul. 2, 2014, for U.S. Appl. No. 13/462,734, 5 pages.

* cited by examiner

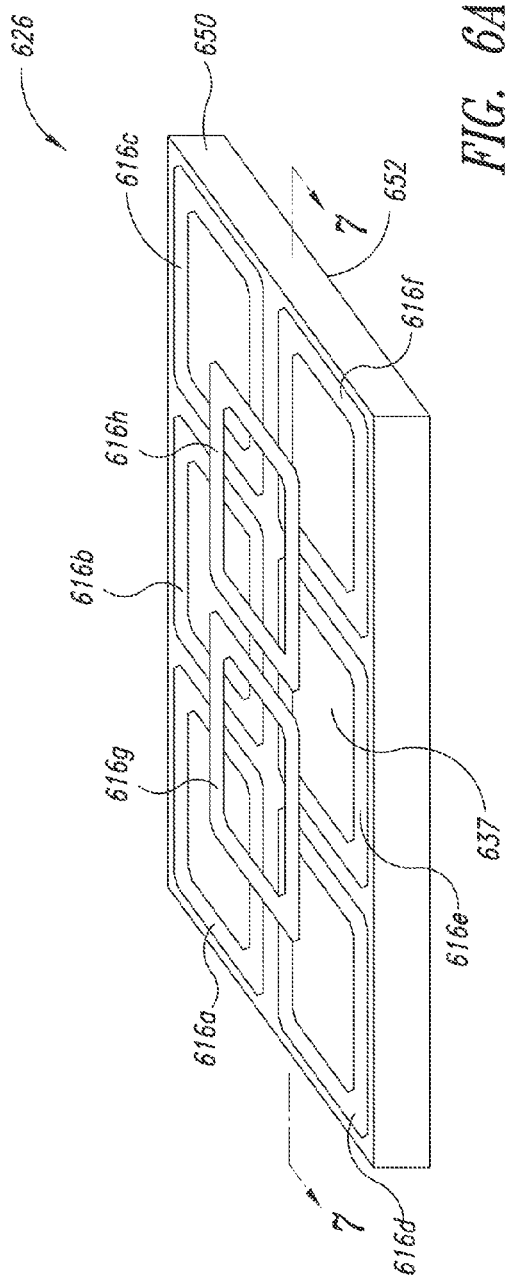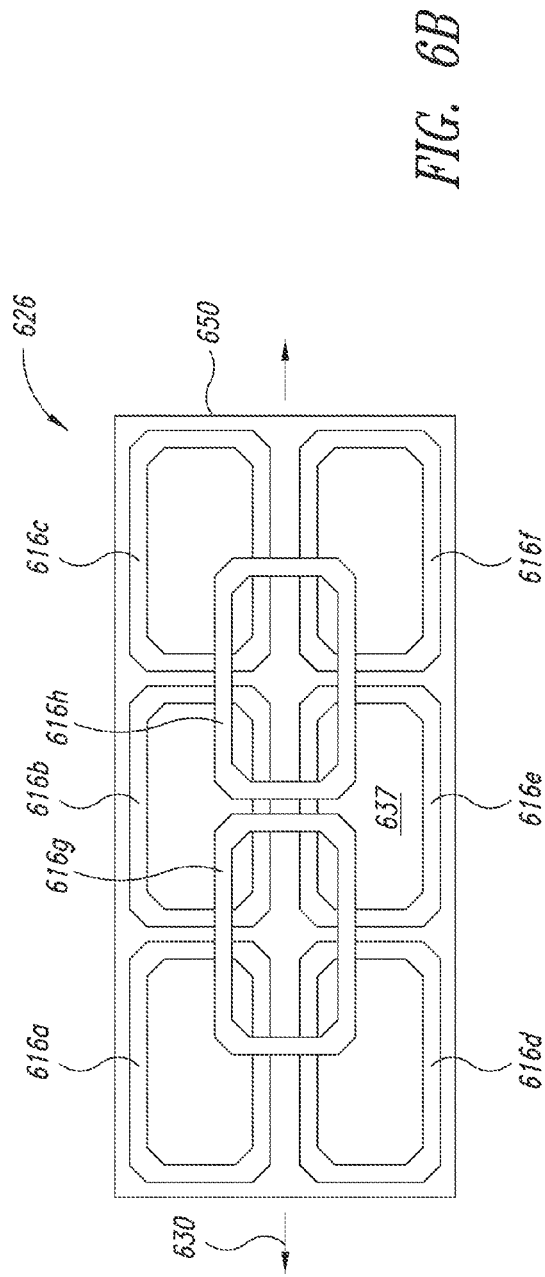

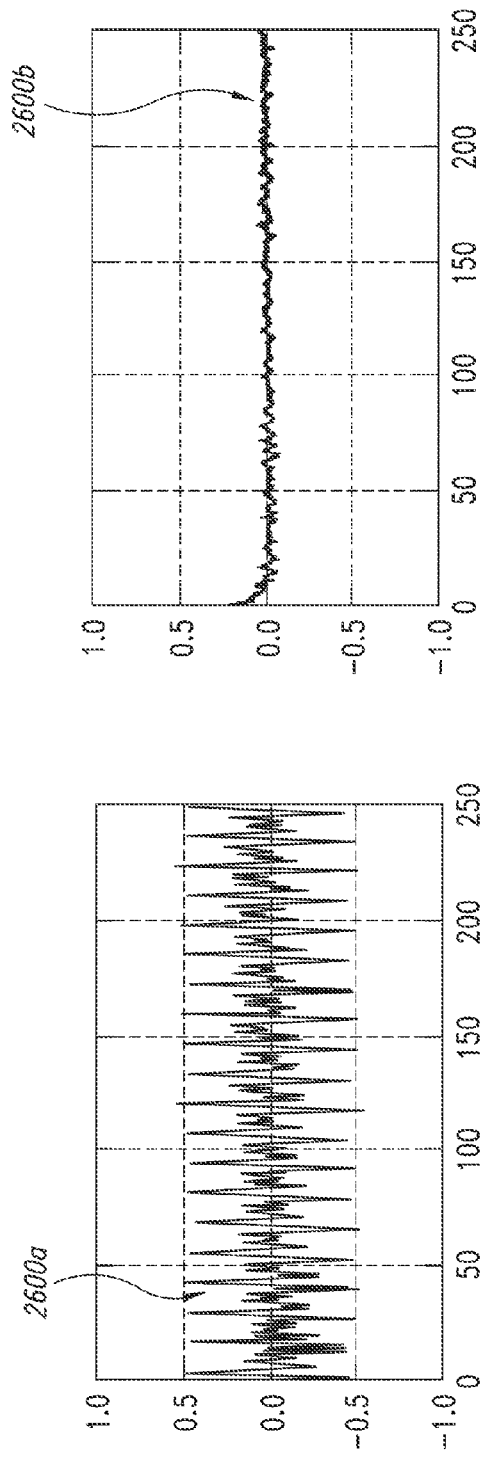
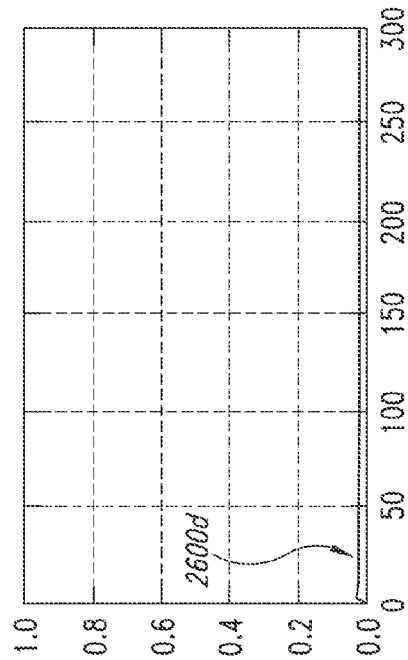
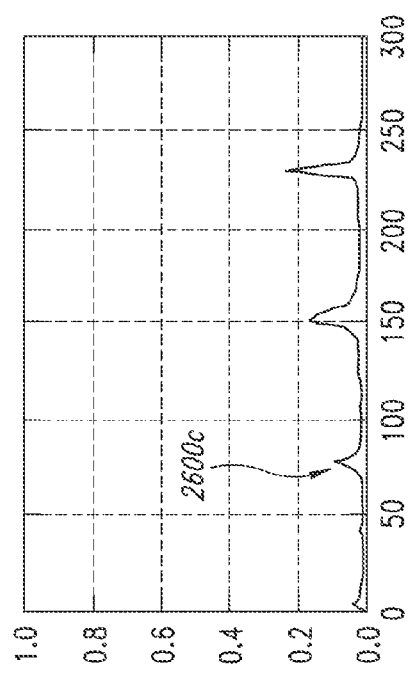
FIG. 26A
FIG. 26B
FIG. 26C
FIG. 26D

METHOD AND APPARATUS TO DETECT TRANSPONDER TAGGED OBJECTS, FOR EXAMPLE DURING MEDICAL PROCEDURES

CROSS REFERENCE TO RELATED APPLICATIONS

This application is a continuation of U.S. patent application Ser. No. 13/462,734 filed May 2, 2012, which is a continuation of U.S. patent application Ser. No. 12/606,688 filed Oct. 27, 2009, which claims benefit under 35 U.S.C. 119(e) to U.S. Provisional Patent Application Ser. No. 61/109,104 filed Oct. 28, 2008; U.S. Provisional Patent application Ser. No. 61/222,443 filed Jul. 1, 2009; and U.S. Provisional Patent Application Ser. No. 61/242,704 filed Sep. 15, 2009, all of which are incorporated herein by reference in their entireties.

BACKGROUND

Technical Field

This disclosure generally relates to the detection of the presence or absence of objects tagged with transponders, which may, for example, allow the detection of medical supplies, for instance surgical objects during surgery.

Description of the Related Art

It is often useful or important to be able to determine the presence or absence of an object.

For example, it is important to determine whether objects associated with a medical procedure, for instance a surgery or child birth deliveries, are present in a patient's body before completion of the medical procedure. Such objects may take a variety of forms used in medical procedures. For example, the objects may take the form of instruments, for instance scalpels, scissors, forceps, hemostats, and/or clamps. Also for example, the objects may take the form of related accessories and/or disposable objects, for instance sponges, gauzes, and/or absorbent pads. When used in surgery, failure to locate an object before closing the patient may require additional surgery, and in some instances may have serious adverse medical consequences. In other medical procedures, such as vaginal child birth deliveries, failure to remove objects, for instance gauze or absorbent pads can lead to infections.

Some hospitals have instituted procedures which include checklists or requiring multiple counts to be performed to track the use and return of objects during surgery. Such a manual approach is inefficient, requiring the time of highly trained personnel, and is prone to error.

Another approach employs transponders and a wireless interrogation and detection system. Such an approach employs wireless transponders which are attached to various objects used during surgery. The interrogation and detection system includes a transmitter that emits pulsed wideband wireless signals (e.g., radio or microwave frequency) and a detector for detecting wireless signals returned by the transponders in response to the emitted pulsed wideband signals. Such an automated system may advantageously increase accuracy while reducing the amount of time required of highly trained and highly compensated personnel. Examples of such an approach are discussed in U.S. Pat. No. 6,026,818, issued Feb. 22, 2000, and U.S. Patent Publication No. US 2004/0250819, published Dec. 16, 2004.

Commercial implementation of such an automated system requires that the overall system be cost competitive and highly accurate. In particular, false negatives must be avoided to ensure that objects are not mistakenly left in the patient. Some facilities may wish to install a single interrogation and detection system in each surgery theater or room in which medical procedures are conducted, while other facilities may move an interrogation and detection system between multiple surgical theaters or other rooms. In either case, the overall system will require a large number of transponders, since at least one transponder is carried, attached or otherwise coupled to each object which may or will be introduced into a patient or subject during the medical procedure. Consequently, the transponders must be inexpensive. However, inexpensive transponders typically have a relatively large variation in the frequency of signals they emit, making it difficult to accurately detect the signals returned by the transponders. This may be particularly difficult in some environments which are noisy with respect to the particular resonant frequencies of the transponders. Rooms in hospitals in which medical procedures are performed tend to have increasingly larger amounts of electronic equipment, and hence are becoming notoriously noisy environments. Consequently, a new approach to detection of the presence and absence of transponder that facilitates the use of inexpensive transponders is highly desirable.

BRIEF SUMMARY

An apparatus to detect transponder tagged objects which are used in performing medical procedures may be summarized as including a plurality of antennas, at least some of the antennas spaced at intervals along at least a portion of a length of a patient support structure that is sized to support a patient; and a control system communicatively coupled to the antennas and configured to successively transmit an interrogation signal via respective ones of at least two of the antennas and to monitor at least the other ones of the antennas for a response to the interrogation signal in a period following the transmission of the interrogation signal and preceding a transmission of another interrogation signal. The plurality of antennas may include at least three antennas and each of the antennas may include a respective antenna coils, a portion a projected area of each successive one of the antenna coils along the portion of the length of the patient support structure overlapping a portion of a projected area of at least one neighboring one of the antenna coils. The plurality of antennas may include at least six antennas. The control system may be configured to successively transmit an interrogation signal from all of the antennas in the plurality of antennas, one at a time, and to monitor all of the antennas in the plurality of antennas for a response to each of the interrogation signals. The control system may be configured to successively transmit an interrogation signal from all of the antennas in the plurality of antennas, one at a time, and to monitor all of the antennas in the plurality of antennas for a response to each of the interrogation signals except the antenna from which a most recent interrogation signal was transmitted. The control system may be configured to monitor a level of noise, successively transmit an interrogation signal from each the antennas, one at a time, and to monitor all of the antennas for a response to the interrogation signal, determine which of the antennas receives a strongest one of the responses to the interrogation signal, determine a noise estimation based on the monitored level of noise, and subtract the noise estimation from the strongest one of the responses to distinguish a signal portion of the response signal from a noise portion of the response signal. The control system may be configured to determine the noise estimation as an average based on the monitored level of noise on all antennas except the antenna that received the strongest one of the responses to the interrogation signals. The control system may be configured to measure a level of ambient noise detected via a plurality of the antennas during a noise detection portion of a cycle, the noise detection portion temporally spaced from any preceding interrogation portions of the cycle such that transponders, if any, are not responding to any electromagnetic interrogation signals transmitted during any preceding interrogation portions of the cycle; determine a set of noise cancellation factors for each of a number of antenna channels; determine a sample averaging time for sampling noise based on the measured level of ambient noise; determine a sample averaging time for sampling responses to interrogation signals based on the measured level of ambient noise; average noise corrected samples of noise sampled for the determined noise sample averaging time during the noise detection portion of the cycle; transmit a number of electromagnetic interrogation signals via one of the antennas during an interrogation portion of the cycle that follows the noise detection portion; average noise corrected samples of responses sampled for the determined signal averaging time during the interrogation portion of the cycle in a period while no electromagnetic interrogations signals are being transmitted by any of the antennas, the period spaced temporally sufficiently closely to the transmission of the electromagnetic interrogations signals that the transponders, if any, are still responding to the electromagnetic interrogation signals; and compare averaged noise corrected samples of responses to the interrogation signals to at least one transponder detection threshold.

The control system may be further configured to iterate through each of the antennas if averaged noise corrected samples of responses to interrogations signals does not satisfy the at least one transponder detection threshold.

The control system may be further configured provide a notification of detection of a transponder if the averaged noise corrected samples of responses to interrogations signals does satisfies the at least one transponder detection threshold an $N^{th}$ time, where N is greater than 1.

The control system may be further configured to compare at least one noise level measured from before a first interrogation portion of the cycle a noise level measured after the first interrogation portion of the cycle; and increase the sample averaging time for sampling responses to interrogation signals if a result of the comparison indicates a variation in excess of a variation threshold.

The control system may be further configured to determine the set of noise cancellation factors for each of the number of antenna channels by, for each respective antenna channel averaging the measured levels of ambient noise received on all the antenna channels other than the respective antenna channel for which the noise cancellation factor is being determined.

The antennas may be radiolucent, and may further include the patient support structure selected from the group consisting of: an operating table, a patient bed, a mattress, a pad and a sheet.

A method to detect transponder tagged objects which are used during medical procedures may be summarized as including for each of at least three antennas spaced at intervals along at least a portion of a length of a patient support structure, successively transmitting a number of interrogation signals via respective ones of the antennas; and monitoring at least the other ones of the antennas for a response to the interrogation signals in a period following the transmission of the interrogation signal and before transmitting another number of interrogation signals via a next one of the antennas. Successively transmitting a number of interrogation signals via respective ones of the antennas may include transmitting the interrogation signals from all of the antennas, one at a time, and monitoring at least the other ones of the antennas for a response to the interrogation signals may include monitoring all of the antennas in the plurality of antennas for a response to each of the interrogation signals. Successively transmitting a number of interrogation signals via respective ones of the antennas may include transmitting the interrogation signals from all of the antennas in the plurality of antennas, one at a time, and monitoring at least the other ones of the antenna for a response to the interrogation signals may include monitoring all of the antennas except the antenna from which a most recent interrogation signal was transmitted for a response to the most recent interrogation signal.

The method may further include measuring a level of ambient noise detected via a plurality of the antennas during a noise detection portion of a cycle, the noise detection portion temporally spaced from any preceding interrogation portions of the cycle such that transponders, if any, are not responding to any electromagnetic interrogation signals transmitted during any preceding interrogation portions of the cycle; determining a set of noise cancellation factors for each of a number of antenna channels; determining a sample averaging time for sampling noise based on the measured level of ambient noise; determining a sample averaging time for sampling responses to interrogation signals based on the measured level of ambient noise; averaging noise corrected samples of noise sampled for the determined noise sample averaging time during the noise detection portion of the cycle; and wherein successively transmitting a number of interrogation signals via respective ones of the antennas includes transmitting the number of electromagnetic interrogation signals via one of the antennas during an interrogation portion of the cycle that follows the noise detection portion; and monitoring at least the other ones of the antennas for a response to the interrogations signals in a period following transmission of the interrogation signal includes averaging noise corrected samples of responses sampled for the determined signal averaging time during the interrogation portion of the cycle in a period while no electromagnetic interrogations signals are being transmitted by any of the antennas, the period spaced temporally sufficiently closely to the transmission of the electromagnetic interrogations signals that the transponders, if any, are still responding to the electromagnetic interrogation signals.

The method may further include comparing averaged noise corrected samples of responses to the interrogation signals to at least one transponder detection threshold; and iterating through each of the antennas if averaged noise corrected samples of responses to interrogations signals does not satisfy the at least one transponder detection threshold.

The method may further include providing a notification of detection of a transponder if the averaged noise corrected samples of responses to interrogations signals does satisfies the at least one transponder detection threshold an $N^{th}$ time, where N is greater than 1.

The method may further include comparing at least one noise level measured from before a first interrogation portion of the cycle a noise level measured after the first interrogation portion of the cycle; and increasing the sample averaging time for sampling responses to interrogation signals if a result of the comparison indicates a variation in excess of a variation threshold. Determining the set of noise cancellation factors for each of the number of antenna channels may include, for each respective antenna channel averaging the measured levels of ambient noise received on all the antenna channels other than the respective antenna channel for which the noise cancellation factor is being determined. Successively transmitting a number of interrogation signals may include successively transmitting the interrogations signals at a number of different frequencies at a number of different times.

An apparatus to detect transponder tagged objects which are used in performing medical procedures may be summarized as including a patient support structure that is sized to support a patient; and at least three antennas positioned along at least a portion of a length of the patient support structure, each of the antennas positioned along the length of the patient support structure radiolucent to X-ray frequency electromagnetic energy, and each of the antennas having a respective range, the ranges of the antennas in each neighboring pair of antennas at least partially overlapping. The patient support structure may be elongated having a longitudinal axis and the antennas are coil antennas, at least some of the coil antennas arranged successively along the longitudinal axis. A portion of each successive one of the antenna coils may be arranged successively along the longitudinal axis of the surgical table with a projected area that overlaps a portion of a projected area of at least one neighboring one of the antenna coils. The patient support structure may have at least one X-ray film receiving receptacle and the antennas are positioned between a patient support surface of the patient support structure and the at least one X-ray film receiving receptacle. The antennas may each include a respective stripe-line aluminum coil having a number of windings, each stripe-line aluminum coil has a thickness that is not greater than 200 microns. Each stripe-line aluminum coil may have a thickness that is not greater than 100 microns.

The antennas may be carried by the patient support structure on, in or under a patient support surface, and may further include at least one pad that overlies at least one of the antennas.

The apparatus may further include a control system communicatively coupled to the antennas and configured to successively transmit an interrogation signal via respective ones of the antennas and to monitor at least the other ones of the antennas for a response to the interrogation signal in a period following the transmission of the interrogation signal and preceding a transmission of another interrogation signal.

The apparatus may further include a pedestal that supports the patient support structure, wherein the control system is at least partially housed in the pedestal.

The apparatus may further include at least one antenna port carried by the patient support structure, the at least one antenna port communicatively coupled to at least one of the antennas and communicatively coupleable to the control system.

The apparatus may further include at least one visual indicator carried by the patient support structure, the at least one visual indicator communicatively coupled to the control system and operable thereby to produce visual indications indicative of responses to the interrogation signals; and at least one user switch carried by the patient support structure, the at least one switch communicatively coupled to the control system and operable thereby to control at least one aspect of an operation of the control system. The patient support structure may be at least one of a pad or a mattress that carries the antennas on at least one of an exterior or an interior thereof, and the at least one of the pad or the mattress may include at least one communications interface to provide selectively decoupleable communicative coupling with at least some of the antennas. The at least one of the pad or the mattress may have a compliant inner portion and an outer cover that at least partially surrounds the compliant inner portion and which is impervious to bodily fluids, the compliant inner portion and the outer cover including radiolucent materials that can withstand multiple sterilization cycles. The patient support structure may be a sheet that carries the antennas on at least one of an exterior or an interior thereof, the sheet including at least one communications interface that provides communicative coupling with at least some of the antennas.

The apparatus may further include a number of sensors carried by the patient support structure, the sensors responsive to a respective force exerted by a respective portion of the patient. Each of the sensors may be communicatively coupled to provide a signal indicative of the respective force exerted by the respective portion of the patient.

The apparatus may further include a gel carried by the patient support structure at least at a number of locations that correspond to a number of defined locations of the patient when the patient is supported by the patient support structure.

A system may be summarized as including a transponder tag coupled to a medical supply item, the transponder tag configured to wirelessly receive electromagnetic energy in the form of a number of interrogation signals and to emit a response to the interrogation signal by radiating electromagnetic energy; an array of antennas located in a medical procedure environment in which medical procedures are performed; and a controller communicatively coupled to the array of antennas and configured to perform a transponder detection cycle that includes a number of noise detection portions and a number of interrogation portions temporally spaced from the noise detection portions, during which the controller: monitors at least two of the antennas of the array of antennas for an ambient noise in the medical procedure environment during the noise detection portions of the transponder detection cycle, the noise detection portions spaced sufficiently from the interrogation portions that the transponder is not emitting a response detectable by the controller to any previous interrogation signals; emits a number of interrogation signals from each of at least two of the antennas of the array of antennas, successively, during a number of transmission periods of the interrogation portions of the transponder detection cycle; and monitors at least two antennas for any responses to the interrogation signals during a number of detection periods of the interrogation portions of the transponder detection cycle, the detection periods following respective ones of the transmission periods sufficiently closely in time that the transponder is still emitting a response to the interrogation signals by all of the antennas in the array except one that emitted the most recent signal. The controller may monitor at least two antennas for any responses to the interrogation signals during a number of detection periods of the interrogation portions of the transponder detection cycle by monitoring all antennas of the antenna array. The controller may monitor at least two antennas for any responses to the interrogation signals during a number of detection periods of the interrogation portions of the transponder detection cycle by monitoring all antennas of the antenna array except the antenna that emitted a most recent one of the interrogation signals.

The controller may be further configured to determine a respective noise estimation for each antenna and to compensate any responses received via the antenna using the respective noise estimation.

The controller may be further configured to determine a respective noise estimation for each antenna based on noise monitored on a number of the antennas of the antenna array other than the antenna for which the noise estimation is being determined and to compensate any responses received via one of the antennas using the respective noise estimation for the antenna. The antennas of the antenna array may be physically coupled to a light fixture positioned above a patient support structure. The antennas of the antenna array may be physically coupled to the patient support structure. The antennas of the antenna array may be physically coupled to a curtain adjacent to the patient support structure.

The system may further include a hand held wand antenna communicatively coupled to the controller to emit an number of interrogation signals and to monitor for a number of responses to interrogation signals.

An apparatus may be summarized as including at least one electrically insulative substrate; and a first plurality of antennas distributed along at least a portion of the at least one insulative substrate, each antenna comprising at least one coil with a plurality of windings and composed of a plurality of segments electrically coupled in series to one another, the segments of each antenna carried on at least two different layers and electrically connected through at least one via, the segments on a first layer laterally spaced apart from one another with respect to a longitudinal axis of the coils to form gaps between successively adjacent ones the segments on the first layer, and the segments on at least a second layer laterally spaced apart from one another to form gaps between successively adjacent ones of the segments on the second layer, the segments on the second layer located directly below the gaps formed between the successively adjacent ones of the segments on the first layer. The segments may have a width and the gaps may have a width approximately equal to the width of the segments such that any attenuation of electromagnetic radiation by the segments may be approximately constant in an area enclosed between an outer perimeter and an inner perimeter of each of the antennas. Each antenna may include two coils, a first coil composed of segments on the first layer and the second coil composed of segments on the second layer, and a single electrical connection that electrically connects a distal end of the first coil to a distal end of the second coil through the at least one via.

The apparatus may further include a controller communicatively coupled to the antennas and configured to drive the antennas to emit a number of electromagnetic interrogation signals to provide energy to a transponder, the controller being further configured to monitor at least some of the antennas for any electromagnetic responses from the transponder to the interrogation signals.

The apparatus may further include a hand held wand antenna communicatively coupled to the controller to emit a number of interrogation signals and to monitor for a number of responses to interrogation signals. There may be from six to eight antennas in the first plurality of antennas. The first plurality of antennas may be arranged in a substantially non-overlapping configuration.

The apparatus may further include a second plurality of antennas spaced longitudinally from the first plurality of antennas and which overlap at least some of the antennas of the first plurality of antennas. There may be from six to eight antennas in the first plurality of antennas and from two to four antennas in the second plurality of antennas. The at least one electrically insulative substrate may be part of a patient support structure.

BRIEF DESCRIPTION OF THE SEVERAL VIEWS OF THE DRAWINGS

In the drawings, identical reference numbers identify similar elements or acts. The sizes and relative positions of elements in the drawings are not necessarily drawn to scale. For example, the shapes of various elements and angles are not drawn to scale, and some of these elements are arbitrarily enlarged and positioned to improve drawing legibility. Further, the particular shapes of the elements as drawn, are not intended to convey any information regarding the actual shape of the particular elements, and have been solely selected for ease of recognition in the drawings.

FIG. 6A is a top plan view of a support structure showing a number of antennas on a patient support surface and a number of antennas on an opposed surface, according to yet another illustrated embodiment.

FIG. 6B is a cross-sectional view of the patient support structure of FIG. 6A taken along section line 7 of FIG. 6A.

FIG. 26A is a graph showing a measured or sampled response versus time without noise cancellation where a noise source is present but no transponder is present, according to one illustrated embodiment.

FIG. 26B is a graph showing a measured or sampled response versus time with noise cancellation where a noise source is present but not transponder is present, according to one illustrated embodiment.

FIG. 26C is a graph showing a measured or sampled response versus frequency without noise cancellation where a noise source is present but no transponder is present, according to one illustrated embodiment.

FIG. 26D is a graph showing a measured or sampled response versus frequency with noise cancellation where a noise source is present but not transponder is present, according to one illustrated embodiment.

DETAILED DESCRIPTION

Figure 1:
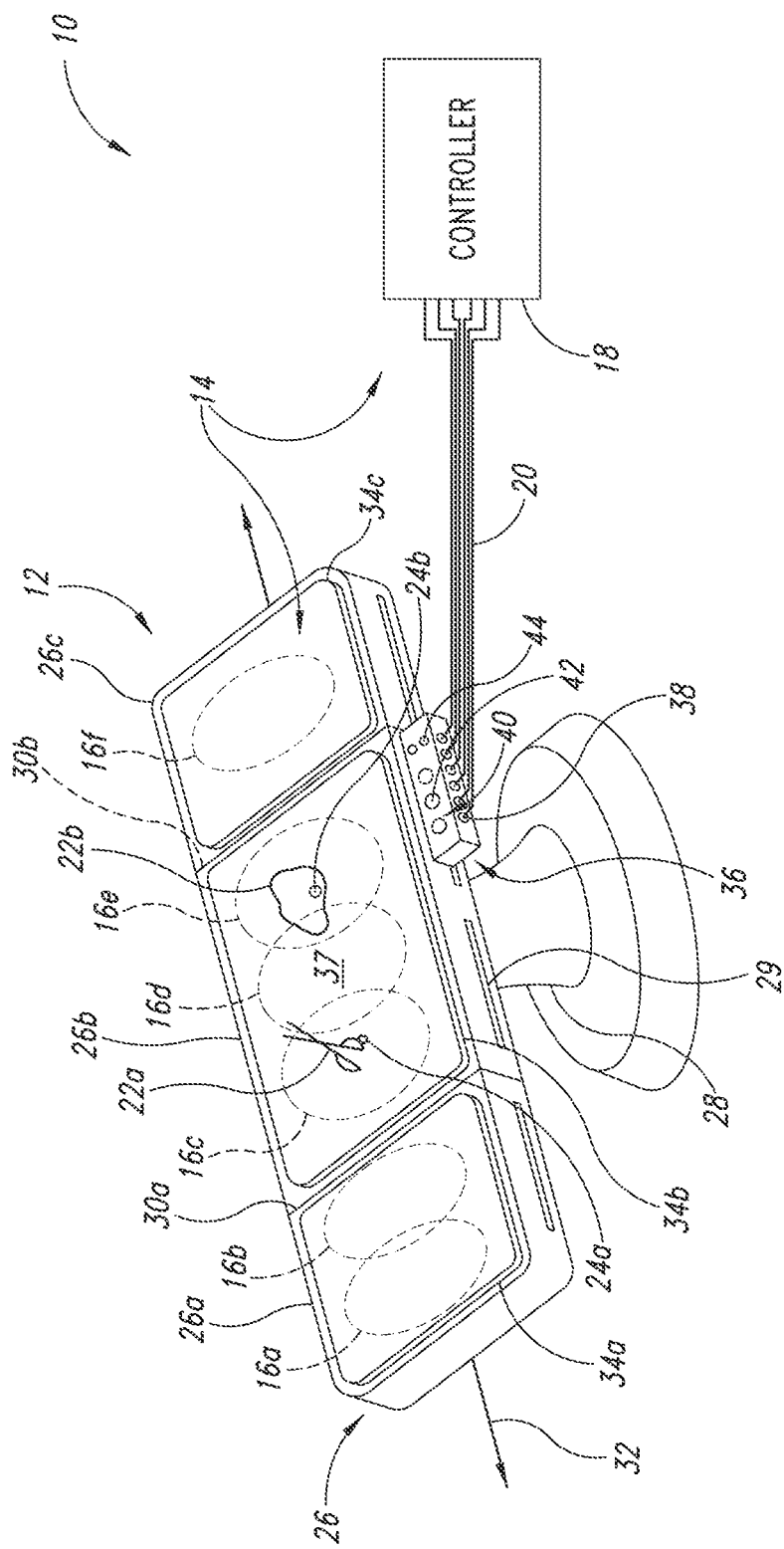
FIG. 1 is a schematic diagram showing an environment in which a medical procedure is performed, for example a surgical environment including a table, bed or other structure to carry or support at least a portion of a patient, that includes a plurality of antennas, and a controller communicatively coupled to the antennas an interrogation and detection system to detect an object tagged with a transponder in a patient, according to one illustrated embodiment.

In the following description, certain specific details are set forth in order to provide a thorough understanding of various disclosed embodiments. However, one skilled in the relevant art will recognize that embodiments may be practiced without one or more of these specific details, or with other methods, components, materials, etc. In other instances, well-known structures associated with transmitters, receivers, or transceivers and/or medical equipment and medical facilities have not been shown or described in detail to avoid unnecessarily obscuring descriptions of the embodiments.

Unless the context requires otherwise, throughout the specification and claims which follow, the word "comprise" and variations thereof, such as, "comprises" and "comprising" are to be construed in an open, inclusive sense, that is as "including, but not limited to."

Reference throughout this specification to "one embodiment" or "an embodiment" means that a particular feature, structure or characteristic described in connection with the embodiment is included in at least one embodiment. Thus, the appearances of the phrases "in one embodiment" or "in an embodiment" in various places throughout this specification are not necessarily all referring to the same embodiment. Further more, the particular features, structures, or characteristics may be combined in any suitable manner in one or more embodiments.

As used in this specification and the appended claims, the singular forms "a," "an," and "the" include plural referents unless the content clearly dictates otherwise. It should also be noted that the term "or" is generally employed in its sense including "and/or" unless the content clearly dictates otherwise.

The headings and Abstract of the Disclosure provided herein are for convenience only and do not interpret the scope or meaning of the embodiments.

Many of the embodiments described herein, perform interrogation and detection of transponder tagged objects using multiple antennas (e.g., six antennas). Successive ones of the antennas may be used to transmit an interrogation signal, while two or more antennas are monitored for a response to the interrogation signal. Such may provide significant advantages over more conventional methods, for example motion based methods that employ motion (e.g., sweeping) of an antenna (e.g., wand) over a patient. For instance, this allows the transmit and receive paths to the transponder to be different from one another (e.g., transmit path is from a first antenna to a transponder, while the receive path is from the transponder to a second antenna). Hence, the path length to the transponder may be shortened in many configurations, thus improving the signal. For instance, when using a single antenna to both transmit an interrogation signal and to receive a response to the interrogation signal, the power of the received signal is equal to about the $6^{th}$ root of the input power. However, when using multiple antennas to transmit and receive over the same area, interrogation path length in one direction may be shorter. Another advantage is that all scan time is averaged, allowing a longer noise time averaging (e.g., 10 seconds) as opposed to motion based scanning, where integration time may be limited (e.g., about 0.25 seconds per sample). Even further, a representative value of noise samples measured over a plurality of antennas may be employed to determine noise to be removed from noise plus signals received at one of the antennas, thereby advantageously lowering a noise floor and/or increasing range or performance. Thus, the various disclosed embodiments may provide significantly better performance.

Figure 2:
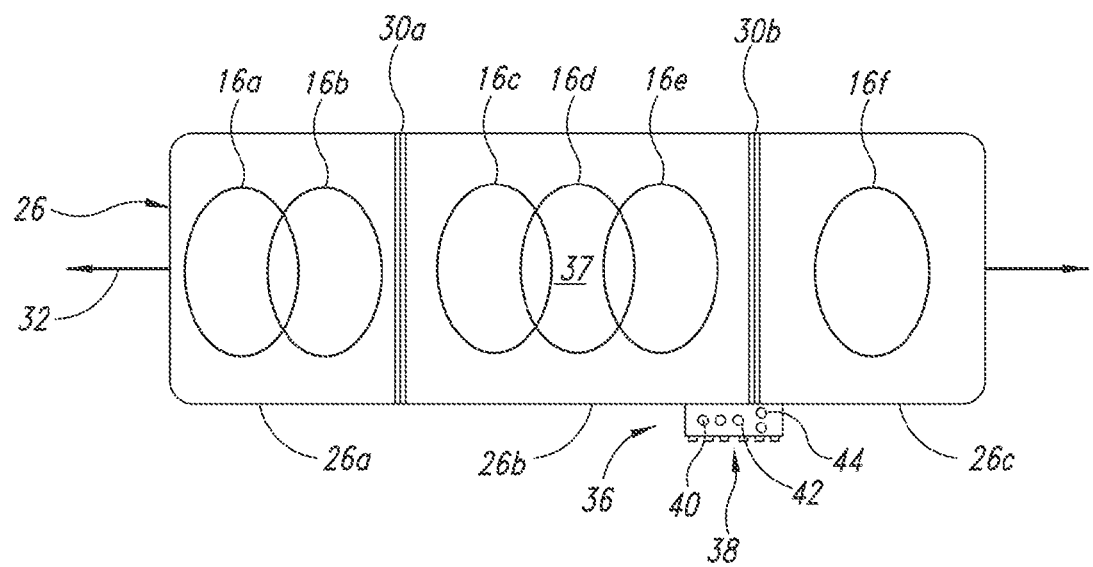
FIG. 2 a top plan view of the table, bed or other structure of FIG. 1 showing the plurality of antennas, according to one illustrated embodiment.

FIGS. 1 and 2 show a medical procedure environment 10 in which medical procedures are performed, for example a surgical environment in which surgeries are performed, a patient room in which child birth deliveries or other medical procedures are performed or a physician's office, etc. The medical procedure environment 10 includes a table (e.g., surgical table), bed, or other structure 12 which can carry a patient or portion thereof and an interrogation and detection system 14. The interrogation and detection system 14 includes a plurality of antennas 16a-16f (collectively 16, shown in broken line in FIG. 1 to indicate that such are hidden in that view) which are carried by the patient support surface 12. The interrogation and detection system 14 also includes a controller 18 communicatively coupleable to the antennas 16 by one or more wired or wireless communication paths, for example coaxial cable 20. As discussed in detail below, the interrogation and detection system 14 is operable to ascertain the presence or absence of objects 22a, 22b (collectively 22) tagged with transponders 24a, 24b (collectively 24), which may be in or on a patient (not shown).

Figure 4:
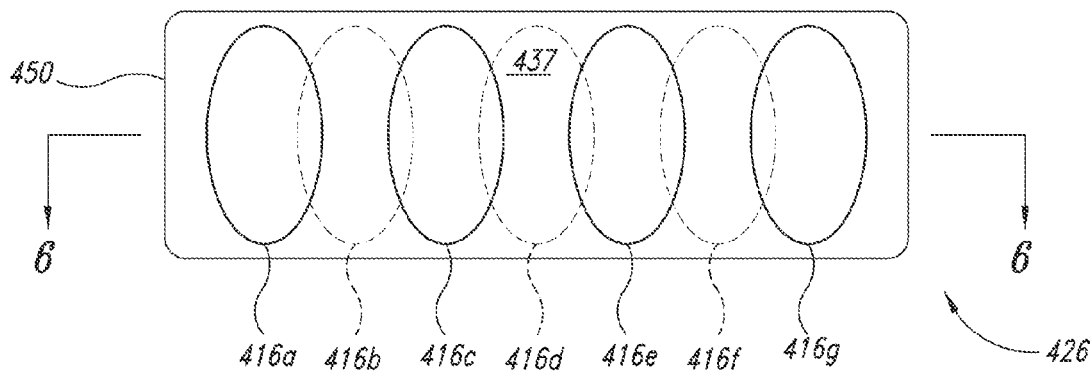
FIG. 4 is a top plan view of a patient support structure showing a number of antennas on a patient support surface and a number of antennas on an opposed surface, according to another illustrated embodiment.
Figure 7:
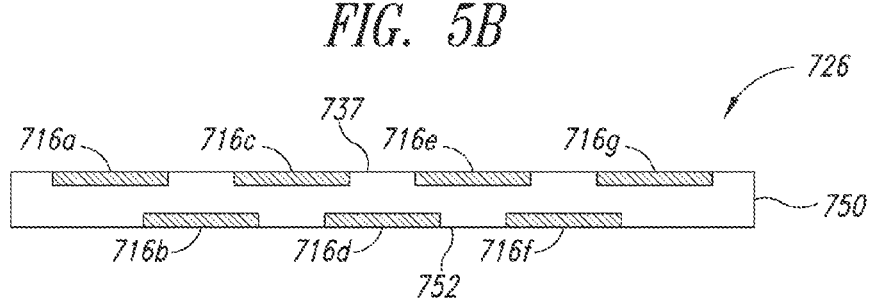
FIG. 7 is a cross-sectional view of a patient support structure having recesses in which the antennas are received, according to another illustrated embodiment.
Figure 9:
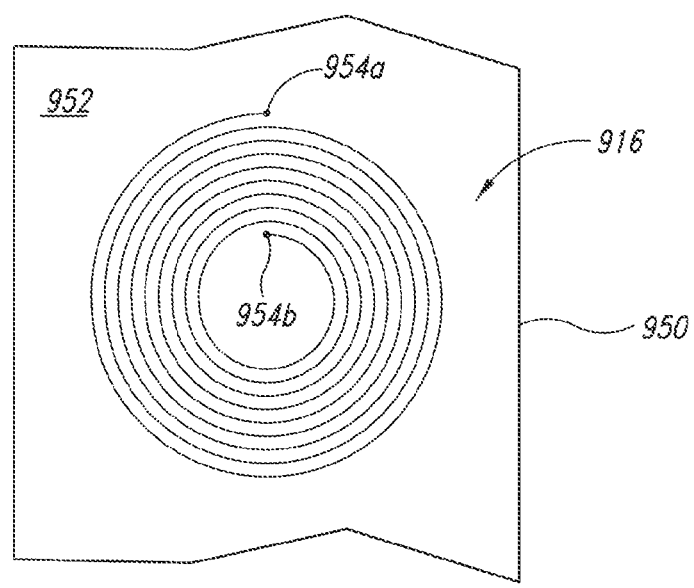
FIG. 9 is an enlarged top plan view of an antenna according to one illustrated embodiment, where the antenna is formed from multiple coils of a conductive material that is radiolucent.

The table, bed or other structure 12 may include a patient support structure 26 and a pedestal or base 28 which supports the patient support structure 26. The patient support structure 26 should have dimensions sufficient to support at least a portion of a patient during a medical procedure, for instance during surgery, child birth, etc. Hence, the patient support structure 26 may have a length of six feet or more and a width of two feet or more. The patient support structure 26 may have two or more articulated sections 26a-26c, as illustrated in FIG. 1 or 2, or may be a unarticulated or unitary structure as illustrated in FIGS. 4, 7 and 9. Hinges 30a, 30b (collectively 30) or other coupling structures may couple the articulated sections 26a-26c. The hinges 30 may, for example, be located along a longitudinal axis 32 of the patient support structure 26 at locations that would approximate the anticipated position of a between a patient's legs and torso and between the patient's torso and head.

The patient support structure 26 is preferably made of a rigid material and is preferably radiolucent. Various radiolucent materials may be employed, for instance carbon fiber or radiolucent plastics. Such advantageously allows radiological technologies to be employed, for example X-ray imaging. For example, the patient support structure 26 may be molded from plastics such as an acrylic or a phenolic resin (e.g., commercially available under the trademark SPAULDITE®). In some embodiments, the patient support structure 26 may include a frame. The frame may be made of a metal which may not be radiolucent. In such embodiments, the frame preferably makes up a small percentage of the total area of the patient support structure 26. The patient support structure 26 may be capable of withstanding multiple cycles of sterilization (e.g., chemical, heat, radiation, etc.). A large variety of surgical tables, patient beds and other structures capable of carrying a patient or a portion of a patient are commercially available. Many of these commercially available structures include electric motors and electronics. Typically, there is no or minimum regulation of non-ionizing electromagnetic radiation generated by such electric motors and electronics. Hence, many environments 10 in which medical procedures are performed tend to be electromagnetically noisy environments.

The table, bed or other structure 12 may include one or more mattresses or pads 34a-34c (collectively 34), and/or may include one or more sheets (not shown in FIG. 1 for sake of clarity of illustration). The mattresses or pads 34 and/or sheets may overlie the antennas 16. The mattresses or pads 34 may take a variety of forms, and may be disposable, or may be capable of withstanding multiple cycles of sterilization (e.g., chemical, heat, radiation, etc.). The mattresses or pads 34 are preferably radiolucent. The mattresses or pads 34 may take a conventional form, for example cotton, open cell or a closed cell foam rubber, with or without an appropriate cover. Alternatively, the mattresses or pads 34 may include one or more bladders (e.g., dual layer urethane envelope) to receive a fluid (e.g., air, water, etc.) to selectively inflate one or more portions of the mattresses or pads 34, and/or to control a temperature of one or more portions of the mattresses or pads 34. In such embodiments, the fluid should be radiolucent. The mattresses or pads 34 may include a cushioning gel or polymer material (e.g., polymer foam). Such may alleviate pressure points, reducing the formation of sores or ulcers, particularly during long medical procedures. In such embodiments, the cushioning gel or polymer material should be radiolucent. The cushioning layer may include recesses or voids formed at locations selected to accommodate a patient's anatomy. The mattresses or pads 34 may be detachably secured to the patient support structure 26 via various fasteners, for instance ties, or hook and loop fastener commonly available under the trademark VELCRO®.

The pedestal or base 28 may be fixed, or may be moveable. The pedestal or base 28 may include one or more actuators (e.g., motors, pumps, hydraulics, etc.) and/or drive mechanisms (e.g., gears, mechanical couplings) or linkages (not shown) that allow a position and/or orientation of the patient support structure 26 to be adjusted. For example, the pedestal or base 28 may telescope to allow the patient support structure 26 to be mechanically raised and lowered. Also for example, the pedestal or base 28 may allow the patient support structure 26 to be mechanically tilted or rotated about an axis that is perpendicular to a patient support surface 37 of the patient support structure 26.

As illustrated, portions of one or more of the antennas 16 may overlap. For example, where the antennas are coil antennas, each formed of one or more coils, a portion of an area enclosed by an outermost coil of each antenna 16 may overlap a portion of an area enclosed by an outermost coil of a neighboring antenna 16. The area enclosed or enclosed area may be an area enclosed by a normal or perpendicular projection of a perimeter defined the outermost coil of the respective antenna 16. In such embodiments, neighboring antennas 16 may be electrically insulated from one another by one or more electrically insulating layers or substrates. For example, successively adjacent antennas 16 may be carried one opposite surfaces (e.g., opposed outer surfaces, or multiple inner surfaces, or one or more outer and inner surfaces) of a single substrate. As discussed in more detail below, the antennas may advantageously be radiolucent, for example being formed of a radiolucent material (e.g., substantially transparent to X-ray or Gamma ray radiation) or a material that at a thickness employed is substantially radiolucent. For example, an electrically conductive trace of aluminum having a thickness of 200 microns or less sufficiently passes X-rays to be considered radiolucent. More preferably, an aluminum trace having a thickness of 30 microns sufficiently passes X-rays such that even a stack or overlapping portions of three coils (combined thickness under 100 microns) to be radiolucent. An antenna may be considered radiolucent if it is not detectable by an radiologist in an X-ray produced via 10 kV to 120 kV X-ray machine, or preferably a 40 KV X-ray machine in conjunction with a standard 12 inch X-ray image intensifier. An antenna may be considered radiolucent if a coil includes thirty turns or windings and is not detectable by an radiologist in an X-ray.

The patient support structure 26 may include one or more film receiving receptacles 29 (only one called out in FIG. 1). The film receiving receptacles 29 may be spaced relatively below a patient support surface 37 of the patient support structure 26. The film receiving receptacles 29 are sized, dimensioned and/or positioned to receive film, for example X-ray film. The film receiving receptacles 29 my be sized and/or dimensioned to receive a film tray or other film holder (not illustrated) which holds the film. Along with the use of radiolucent materials, such advantageously allows a patient X-ray images or other radiological images of the patient to be produced, generated or made, while the patient is supported by the patient support structure 26. As used herein an in the claims, the term radiolucent means substantially transmissive to energy in the X-ray portion of the electromagnetic spectrum, that is passing sufficient X-ray energy to produce an X-ray image at standard power levels and standard conditions employed in conventional medical imaging.

The table (e.g., surgical table), bed or other structure 12 may include an interrogation and detection system interface 36. The interrogation and detection system interface 36 may include one or more communications ports 38 that allow communicative coupling to be selectively or detachably made between the antennas 16 and the controller 18. Such communications ports 38 may, for example, take the form of coaxial connectors, or other communications connectors. Interrogation and detection system interface 36 may include one or more output devices to provide indications to a user. For instance, the interrogation and detection system interface 36 may include one or more visual indicators 40 (only one called out in FIGS. 1 and 2) to provide indications of a presence and/or an absence of an object. Such may also provide a visual indication that is indicative of a status of a scanning operation by the interrogation and detection system 14, for instance scanning started, scanning completed, and/or occurrence of an error condition. The visual indicators 40 may take a variety of forms, for example light sources of one or more colors. Light sources may include incandescent lights, light emitting diodes (LEDs), organic light emitting diodes (OLEDs), and/or liquid crystal displays (LCDs). Also for instance, the interrogation and detection system interface 36 may include one or more aural indicators 42 to provide aural indications of a presence and/or an absence of an object and/or a status of a scan operation or occurrence of an error condition. The aural indicator 42 may, for example, take the form of one or more speakers. The interrogation and detection system interface 36 may include one or more switches 44 that allow input to be provided to the controller 18. Switches 44 may, for example, allow a user to turn ON the interrogation and detection system 14, start a scan operation, stop a scan operation, adjust a sensitivity of the scanning, adjust one or more frequencies, select or adjust an output type (e.g., type of visual alert, type of aural alert) or level (e.g., brightness, sound level or volume, etc.).

The objects 22 may take a variety of forms, for example instruments, accessories and/or disposable objects useful in performing medical procedures, for example surgical procedures, child birth delivery procedures, and/or other medically related procedures. For instance, some objects 16a may take the form of scalpels, scissors, forceps, hemostats, and/or clamps. Also for example, some objects 22b may take the form of sponges (e.g., surgical sponges), gauze and/or padding. The objects 22 are tagged, carrying, attached or otherwise coupled to a respective transponder 24. Some embodiments of the interrogation and detection system 14 disclosed herein are particularly suited to operate with transponders 26 which are not accurately tuned to a chosen or selected resonant frequency. Consequently, the transponders 24 do not require high manufacturing tolerances or expensive materials, and thus may be inexpensive to manufacture.

Transponders 24 may include a miniature ferrite rod with a conductive coil wrapped about an exterior surface thereof to form an inductor (L), and a capacitor (C) coupled to the conductive coil to form a series LC circuit. The conductive coil may, for example, take the form of a spiral wound conductive wire with an electrically insulative sheath or sleeve. The transponder 24 may include an encapsulation that encapsulates the ferrite rod, conductive coil, and capacitor. The encapsulant may be a bio-inert plastic, that protects the ferrite rod, conductive coil and/or capacitor from pressure and/or from fluids, for example bodily fluids. In some embodiments, the ferrite rod may include a passage sized to receive a physical coupler, for example a bonding tie or string. The bonding tie or string may take the form of an elastomeric x-ray opaque flexible elongated member, that may be used to attach the transponder 24 to various types of objects 22, for example surgical sponges. The transponder 24 may have a length of about 8 millimeters and a diameter of about 2 millimeters. Employing such small dimensions ensures that the transponder 24 does not impede deformation of objects 16 such as sponges. The transponder 24 may include an optional diode (not shown), to protect against over-voltage occurrences caused by other electronic instruments. The transponders 24 may be attached to hemostats, scissors, certain forms of forceps, and the like. In some embodiments, the transponders 24 may be coupled to the object 22 by way of a clamp or holder. In some embodiments, the transponders 24 may be retained within a cavity of the holder. In some embodiments, the holder may be fashioned of a durable deformable material, such as surgical grade polymer, which may be deformed to clamp securely onto the finger or thumbhole of an instrument. In other embodiments, the transponders 24 may be attached to objects 22 by way of pouches fashioned of sheet material (e.g., surgical fabric) surrounding the transponder 24. The transponder 24 is retained within the pouch, and in some embodiments the pouch may be sewn or otherwise sealed. Sealing may be done with adhesive, hot glue, clamping, grommeting, or the like. Various embodiments of suitable transponders and retention devices are discussed in U.S. Provisional Patent Application No. 60/811,376 filed Jun. 6, 2006, U.S. Provisional Patent Application No. 61/091,667 filed Aug. 25, 2008, U.S. patent application Ser. No. 11/759,141 filed Jun. 6, 2007, U.S. patent application Ser. No. 12/046,396 filed Mar. 11, 2008, U.S. Pat. No. 6,026,818 issued Feb. 22, 2000, U.S. Design patent application Ser. No. 29/322,539 filed Aug. 6, 2008 and U.S. Design Pat. No. D568,186 issued May 6, 2008, all of which are incorporated herein by reference in their entireties.

In use, the medical provider 12 may use the switches 44 to cause a scan of the patient 18, for instance jut before closing during surgery, in order to detect the presence or absence of the transponder 26, and hence an object 16.

Figure 3:
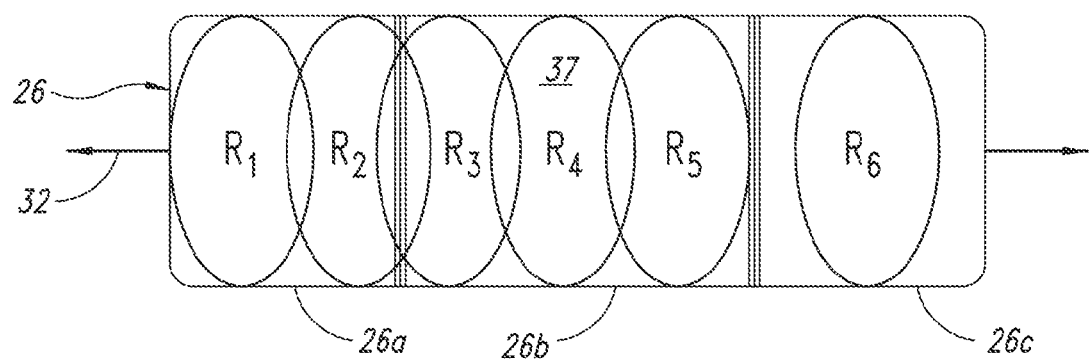
FIG. 3 is a top plan view of the table, bed or other structure of FIG. 1 showing approximate ranges of each of the antennas of FIG. 2.

FIG. 3 shows approximate ranges $R_1$-$R_6$ for the six antennas 16 of the embodiment of FIGS. 1 and 2.

FIG. 3 is illustrative and does not necessarily represent actual ranges. The illustrated ranges $R_1$-$R_6$ (collectively R) show that the ranges $R_1$-$R_6$ are typically larger than the area of the antennas 16. Ranges $R_1$-$R_6$ may be affected by a variety of factors, including the power of the interrogation signal, distance between the transponders 24 and the antennas 16, and/or the sensitivity and/or impedance matching between the transponders 24 and interrogation and detection system 14. Many of the ranges $R_1$-$R_5$ overlap neighboring ranges $R_1$-$R_5$, although in this illustrated embodiment one range R6 does not overlap any other range $R_1$-$R_5$. In other embodiments, all ranges overlap. Alternatively, none of the ranges may overlap. Other arrangements of antennas 16 and/or ranges R, are of course possible.

Figure 5A:
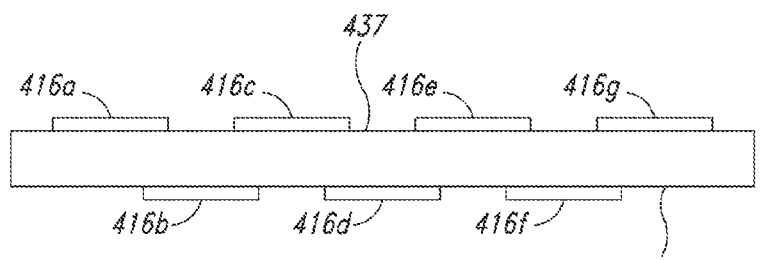
FIG. 5A is a side elevational view of the patient support structure of FIG. 4.
Figure 5B:
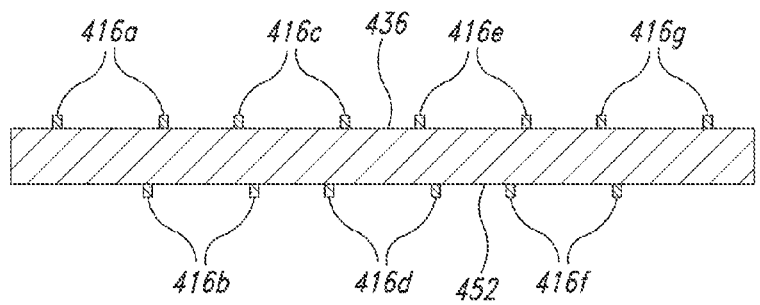
FIG. 5B is a cross-sectional view of the patient support structure of FIG. 4 taken along section line 6 of FIG. 4.

FIGS. 4, 5A and 5B show a patient support structure 626, according to another illustrated embodiment.

The patient support structure 626 may, for example, be part of a table, for instance a surgical table, part of a bed or another structure designed to carry a patient or portion of a patient. The patient support structure 626 is a non-articulated, single piece or unitary structure. While illustrated as a single, unitary construction, the patient support structure 626 may be formed of two or more sections, which may or may not be articulated. The patient support structure 626 is formed as a substrate 650 having a patient support surface 637 and an opposed surface 652 that is opposed from the patient support surface 637. The substrate 650 may be formed of one or more layers. For example, the substrate 650 may be a composite material. The substrate 650 may, for example, be formed as a resin impregnated carbon fiber structure, which may advantageously omit any metal or ferrous metal structural elements. Alternatively, the substrate 650 may minimize the use of any metal or ferrous metal structural elements and locate any metal or ferrous metal structural elements at the peripheries of the substrate 650.

A first set of antennas 616a, 616c, 616e, 616g are positioned on the patient support surface 637, while a second set of antennas 616b, 616d, 616f are positioned on the opposed surface 652. Such allows neighboring ones of the antennas (collectively 616), or portions thereof, to overlap, while electrically insulating each antenna 616 from one another. While illustrated as being carried on outer surfaces of the patient support structure 650 one or more of the antennas 616 could be carried on one or more inner layers of the patient support structure 650 where the patient support structure 650 is formed of two or more layers, for instance as a laminate structure.

Figure 6C:
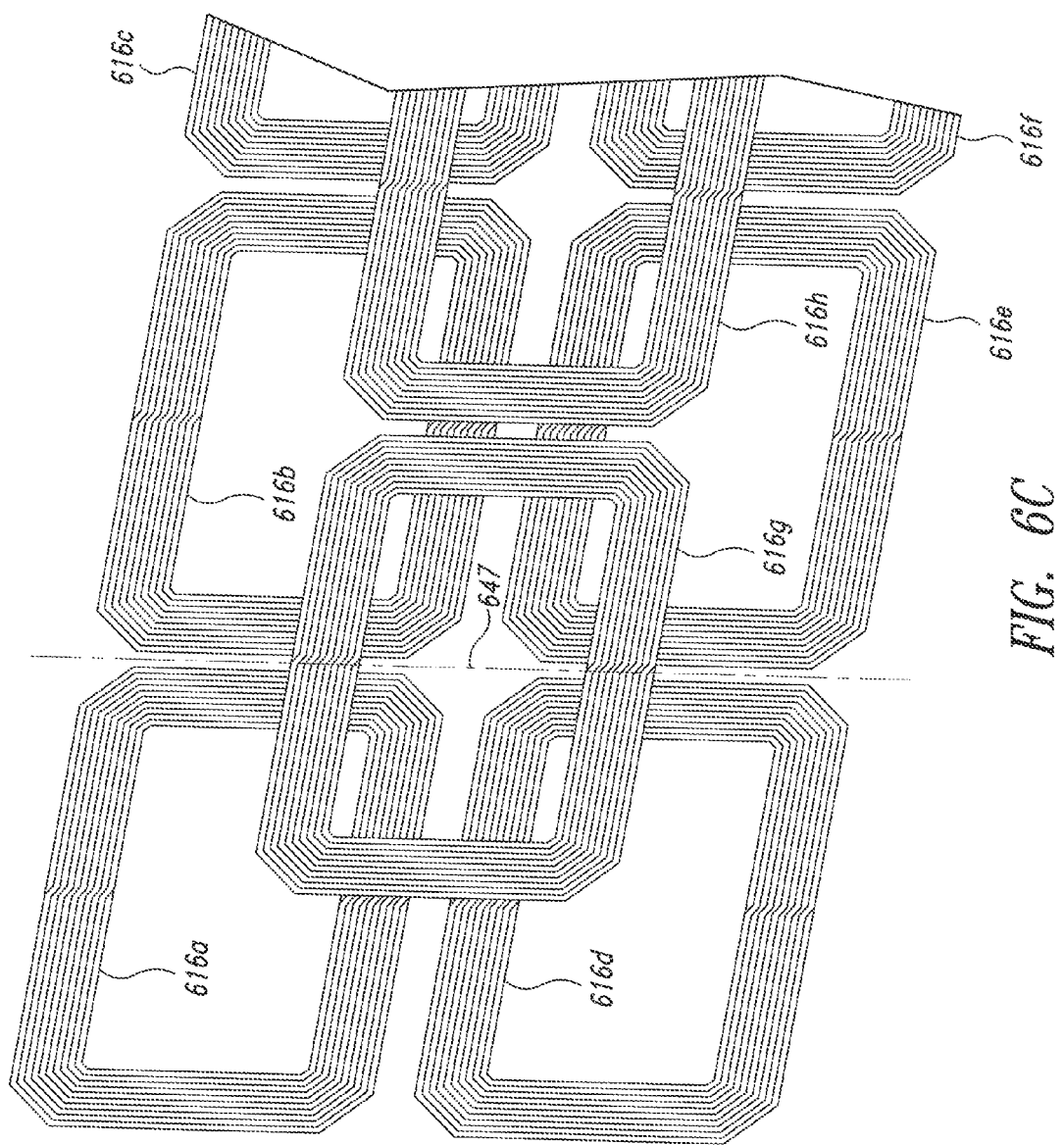
FIG. 6C is a partial isometric view of the patient support structure of FIGS. 6A and 6B, enlarged to illustrated electrically conductive paths or traces of the antennas.

FIGS. 6A-6C show a patient support structure 626 and antennas 616a-616h (collectively 616), according to another illustrated embodiment, wherein individual ones of the electrically conductive paths or traces of the antennas 616 are visible.

The patient support structure 626 may, for example, be part of a table, for instance a surgical table, part of a bed (e.g., patient or hospital bed) or another structure designed to carry a patient or portion of a patient on which a medical procedure may be performed. The patient support structure 626 is a non-articulated, single piece or unitary structure.

While illustrated as a single, unitary construction, the patient support structure 626 may be formed of two or more sections, which may or may not be articulated. The patient support structure 626 is formed as a substrate 650 having a patient support surface 637 and an opposed surface 652 that is opposed from the patient support surface 637. The substrate 650 may be formed of one or more layers. For example, the substrate 650 may be a composite material. The substrate 650 may, for example, be formed as a resin impregnated carbon fiber structure, which may advantageously omit any metal or ferrous metal structural elements. Alternatively, the substrate 650 may minimize the use of any metal or ferrous metal structural elements and locate any metal or ferrous metal structural elements at the peripheries of the substrate 650.

The patient support structure 626 carries antennas 616 thereon and/or therein. As best illustrated in FIGS. 6A and 6B, the antennas can be treated as two sets. A first set of antennas 616a-616f arranged generally adjacent one another in an array of two rows on either side of a longitudinal axis 630 and three columns spaced along the longitudinal axis 630. These antennas 616a-616f do not overlap with one another. These antennas 616a-616f substantially extend the full length and width of the patient support structure 628. Alternatively, these antennas 616a-616f may be spaced inwardly from a perimeter of the patient support structure, for example where the range of the antennas 616a-616f sufficiently covers the area of the patient support structure 626. A second set of antennas 616g, 616h are arranged generally adjacent one another in an array of one row and two columns. These antennas 616g, 616h do not overlap with one another, however these antennas 616g, 616h overlap the antennas 616a-616f of the first set when viewed from above the patient support structure 626. These antennas 616g, 616h enhance the overall coverage of the entire area of the patient support structure 626 and volume spaced generally there above.

While illustrated as being carried an upper outer surface 637 of the patient support structure 626, one or more of the antennas 616 could be carried on a lower outer surface 652 and/or on one or more inner layers of the patient support structure 626, for instance where the patient support structure 626 is a laminate structure.

FIG. 6C shows one embodiment of the antennas 616, which may allow relatively simple and low cost manufacturing, and which prevents the antennas 616 from electrically shorting one another.

In particular, each antenna may be formed as electrically conductive paths or traces on one or more layers of an electrically non-conductive or insulative substrate, for instance a flexible substrate of circuit board material (e.g. FR4, Kapton). The electrically conductive path or trace may form a coil pattern, hence a coil antenna with multiple windings, as illustrated in FIG. 6C. Portions of the electrically conductive path on one end or half of the substrate may be electrically coupled to respective portions of the electrically conductive path on the other end or half of the substrate via electrically conductive material received in a via that extends through a portion or all of the substrate. Thus, while the electrically conductive paths appear to terminate at a centerline 647 of each antenna, the electrically conductive paths are in fact electrically coupled to adjacent portions across the centerline 647 by way of respective vias. Alternatively, the electrically conductive path may have change in direction (e.g., 45 degree turn), such that the electrically conductive path spirals inwardly (or outwardly) with each half turn or half winding. Alternatively, or additionally, an electrically non-conductive or electrically insulative material may overlie the electrically conductive path on a lower surface or side and/or an upper surface or side of the substrate, to provide electrical insulation between overlying substrates.

FIG. 7 shows a patient support structure 726, according to another illustrated embodiment.

The patient support structure 726 is formed as a substrate 750 having a patient support surface 737 and an opposed surface 752 that is opposed from the patient support surface 737. The substrate 750 may be formed of one or more layers. For example, the substrate 750 may be a composite material. The substrate 750 may, for example, be formed as a resin impregnated carbon fiber structure, which may advantageously omit any metal or ferrous metal structural elements. Alternatively, the substrate 750 may minimize the use of any metal or ferrous metal structural elements and locate any metal or ferrous metal structural elements at the peripheries of the substrate 750. While illustrated as a single, unitary construction, the patient support structure 726 may be formed of two or more sections, which may or may not be articulated.

A first set of antennas 716a, 716c, 716e, 716g are positioned in respective recesses formed in the patient support surface 737, while a second set of antennas 716b, 716d, 716f are positioned in respective recesses formed in the opposed surface 752. Such allows neighboring ones of the antennas (collectively 716) to overlap, while electrically insulating each antenna 716 from one another. Such also advantageously spaced the antennas 716 of the first and second sets closer together with respect to one another, which may produce more consistent results or performance between the various antennas 716. While illustrated as being carried on outer surfaces of the patient support structure 750 one or more of the antennas 716 could be carried on one or more inner layers of the patient support structure 750 where the patient support structure 750 is formed of two or more layers, for instance as a laminate structure.

Figure 8A:
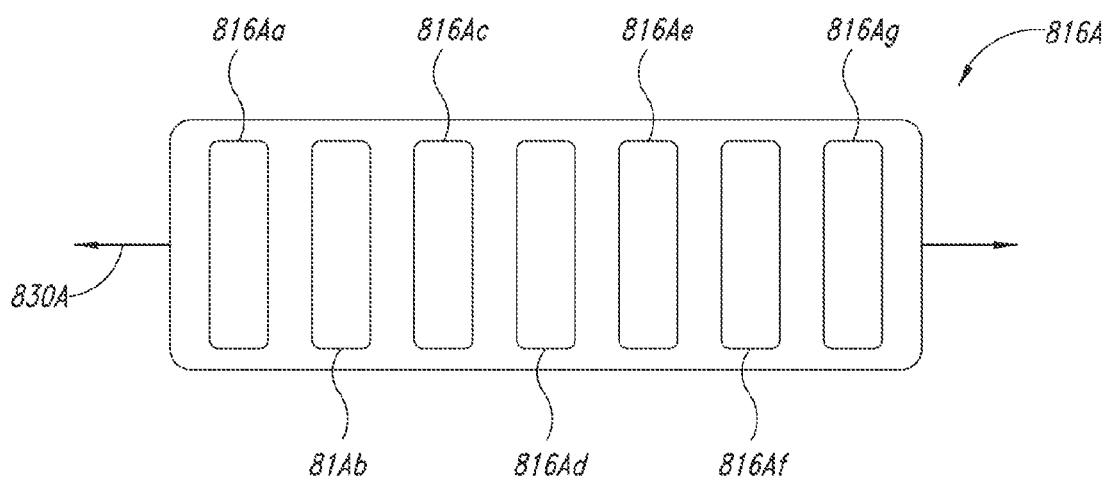
FIG. 8A is a top plan view of a patient support structure in the form of a bed or an operating table showing a number of antennas arranged in a non-overlapping relationship, according to another illustrated embodiment.

FIG. 8A shows a patient support structure 826A, according to another illustrated embodiment.

The patient support structure 826A is a non-articulated, single piece or unitary structure. While illustrated as a single, unitary construction, the patient support structure 826A may be formed of two or more sections, which may or may not be articulated. The patient support structure 826A may be formed of a variety of materials, for example, the materials of the above described embodiments.

Notably, the patient support structure 826A carries a set of antennas 816Aa-816Af (collectively 816A), which are positioned along a longitudinal axis 830 of the patient support structure 826A. While illustrated as positioned in non-overlapping fashioned, in some embodiments the antennas 816A may be positioned in overlapping fashion. While five antennas 816B are illustrated, the patient support structure 826A may include a greater or lesser number of antennas 816A. Consequently, the antennas 816A may all be carried on the same outer surface (e.g., patient support surface) or inner surface or layer. Thus, may advantageously provide more consistent results or performance between the respective antennas 816, and/or may simply manufacturing and/or maintenance.

Figure 8B:
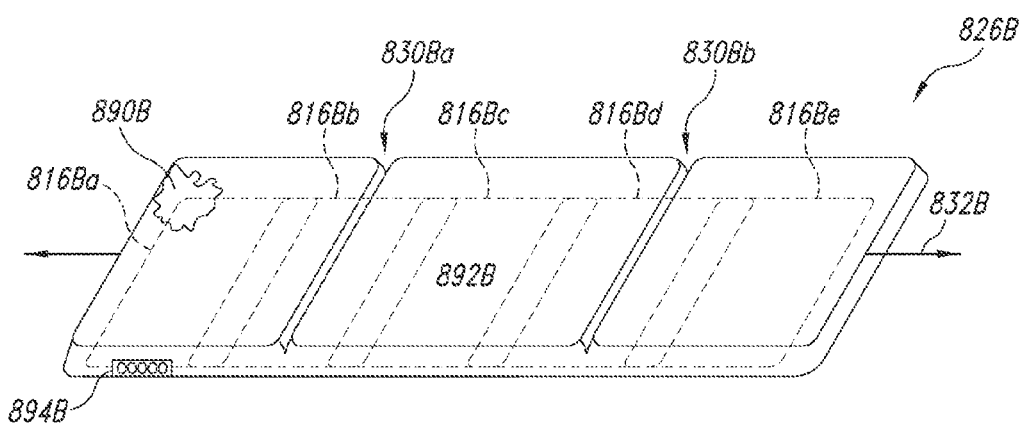
FIG. 8B is a top plan view of a patient support structure in the form of a mattress or pad showing a number of antennas arranged in a non-overlapping relationship, according to another illustrated embodiment.

FIG. 8B shows a patient support structure, according to another illustrated embodiment.

The patient support structure takes the form of a mattress or pad 826B which may, for example, be used on a table or bed when performing a medical procedure. While illustrated as an articulated structure with two joints or hinges 830Ba, 830Bb (collectively 830B), the mattress or pad 826B may be formed of a unitary, single piece non-articulated structure. The mattress or pad 826B may be reusable, and hence should be capable of withstanding repeated sterilization procedures (e.g., heat, chemical, radiation, etc.). Alternatively, the mattress or pad 826B may be disposable after a single use. The mattress or pad 826B may be formed of a variety of materials, for example, the materials of the above described embodiments of mattresses or pads. As previously discussed in reference to mattresses or pads, the mattress or pad 826B may include an outer layer or cover 892B and an interior 890B (visible through broken portion of outer layer 892B). The outer layer or cover 892B provides environmental protection to the interior 890B. The interior 890B may, for example, take the form of a conformable interior, which may be made of any variety of materials. Suitable material may, for example, include cotton or a foam material such as a closed or an open cell foam rubber or LATEX®. Alternatively, the conformable interior may take the form of a fluid (e.g., a liquid or a gas). The outer layer or cover 892B may be made of cotton, nylon, rayon or other natural or synthetic materials. The outer layer or cover 892B may, for example, be impervious to liquids. For example, the outer layer or cover 892B may include one or more layers of a rubber, LATEX®, polyvinyl chloride, plastic or other material that is impervious to fluids, for example bodily fluids.

Notably, the mattress or pad 826B carries a set of antennas 816Ba-816Be (collectively 816B), which are positioned along a longitudinal axis 832B of the mattress or pad 826B. While illustrated as positioned in overlapping fashioned, in some embodiments the antennas 816B may be positioned in non-overlapping fashion. While five antennas 816B are illustrated, the mattress or pad 826B may include a greater or lesser number of antennas 816B. For example, the mattress or pad 826B may have antennas 816 arranged in a similar fashion to that illustrated in FIGS. 6A-6C. The antennas 816B may on opposite sides of a layer on or in the mattress or pad 826B, or on two or more different layers on or in the mattress or pad 826B. The layer or layers may be an outer surface (e.g., patient support surface) or an inner surface or layer. The mattress or pad 826B includes an interface, such as a connector 894B, to allow the antennas 816B to be communicatively coupled to the controller 18 (FIG. 1).

Figure 8C:
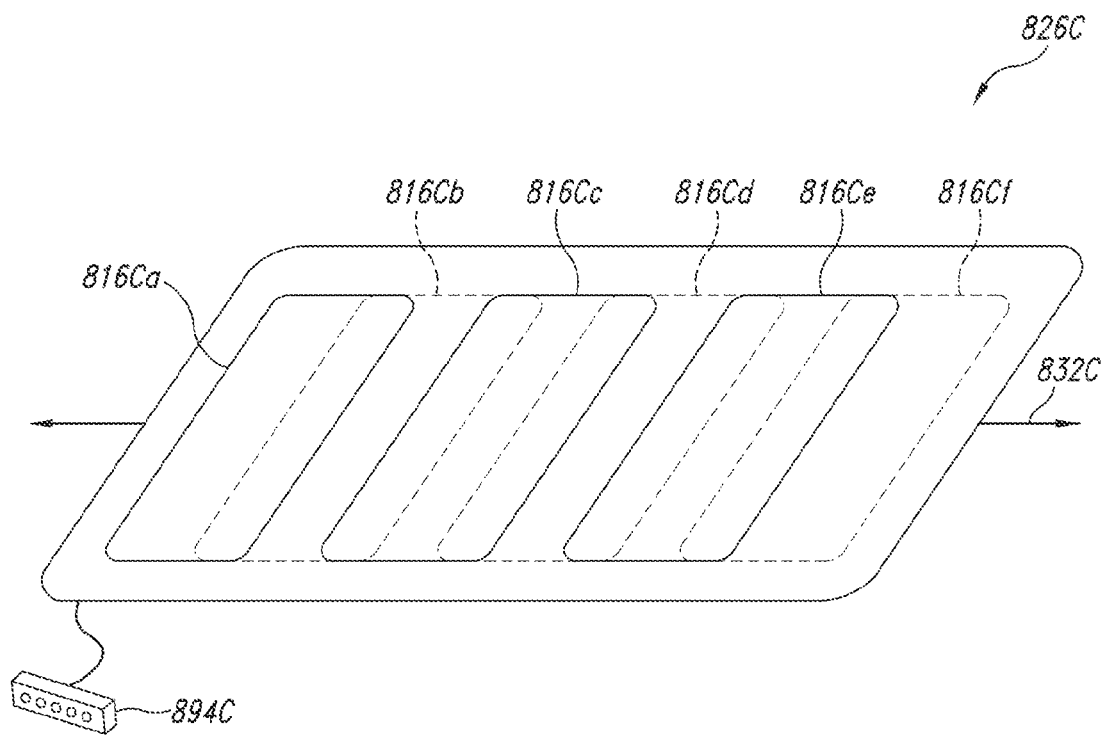
FIG. 8C is a top plan view of a patient support structure in the form of a sheet showing a number of antennas arranged in a non-overlapping relationship, according to another illustrated embodiment.

FIG. 8C shows a patient support structure, according to another illustrated embodiment.

The patient support structure takes the form of a sheet 826C. The sheet 826C may, for example, be used on, over, or in conjunction with a table, bed, frame or other structure during a medical procedure. The sheet 826C may be formed of a unitary, single piece of material or a cloth, for example a fabric. The cloth may, for example, be woven, knitted, felted, pressed, etc. The sheet 826C may be reusable, and hence should be capable of withstanding repeated sterilization procedures (e.g., heat, chemical, radiation, etc.). Alternatively, the sheet 826C may be disposable after a single use. The sheet 826C may be absorbent or may be impermeable to fluids, for example bodily fluids. The sheet 826C may be formed of a variety of materials, for example, cotton, nylon, rayon, or other natural or synthetic fibers. For example, the sheet 826C may include one or more layers of a rubber, LATEX®, polyvinyl chloride, plastic or other material that is impervious to fluids, for example bodily fluids.

Notably, the sheet 826C carries a set of antennas 816Ca-816Ce (collectively 816C), which are positioned along a longitudinal axis 832C of the sheet 826C. While illustrated as positioned in overlapping fashioned, in some embodiments the antennas 816C may be positioned in non-overlapping fashion. While six antennas 816C are illustrated, the sheet 826C may include a greater or lesser number of antennas 816C. For example, the antennas 816 may be arranged on the sheet 826 in an identical or similar fashion as illustrated in FIGS. 6A-6C. The antennas 816C may be on opposite sides of the sheet 826C, or on two or more different layers of the sheet 826C. The layer or layers may be an outer surface (e.g., patient support surface) or an inner surface or layer. The sheet 826C includes an interface, such as a connector 894C, to allow the antennas 816C to be communicatively coupled to the controller 18 (FIG. 1).

FIG. 9 shows an antenna 916, according to one illustrated embodiment. The antenna 916 may, for example, be suitable for use in any of the previously described embodiments.

The antenna 916 may, for example, take the form of an annulus or air-coil formed of coils of conductive material. The conductive material may, for example, take the form of wire or may take the form of a conductive trace printed or otherwise deposited on an inner layer or an outer surface 952 of a substrate 950. In one embodiment, the antenna 916 includes ten turns evenly spaced between an inner diameter of about 11 inches and an outer diameter of about 14 inches. The antenna 916 acts as an inductor. While being formed of a conductive material, the antenna 916 is preferably formed of a radiolucent material. For example, the antenna 916 may be formed as a thin (e.g., thickness, width) strip line aluminum antenna.

The antenna 816 includes a pair of terminals 854a, 854b that provide electrical coupling to the controller 18 (FIG. 1), for example via the ports 38 of interrogation and detection system interface 36 (FIGS. 1 and 2) and the coaxial cable 20.

Figure 10A:
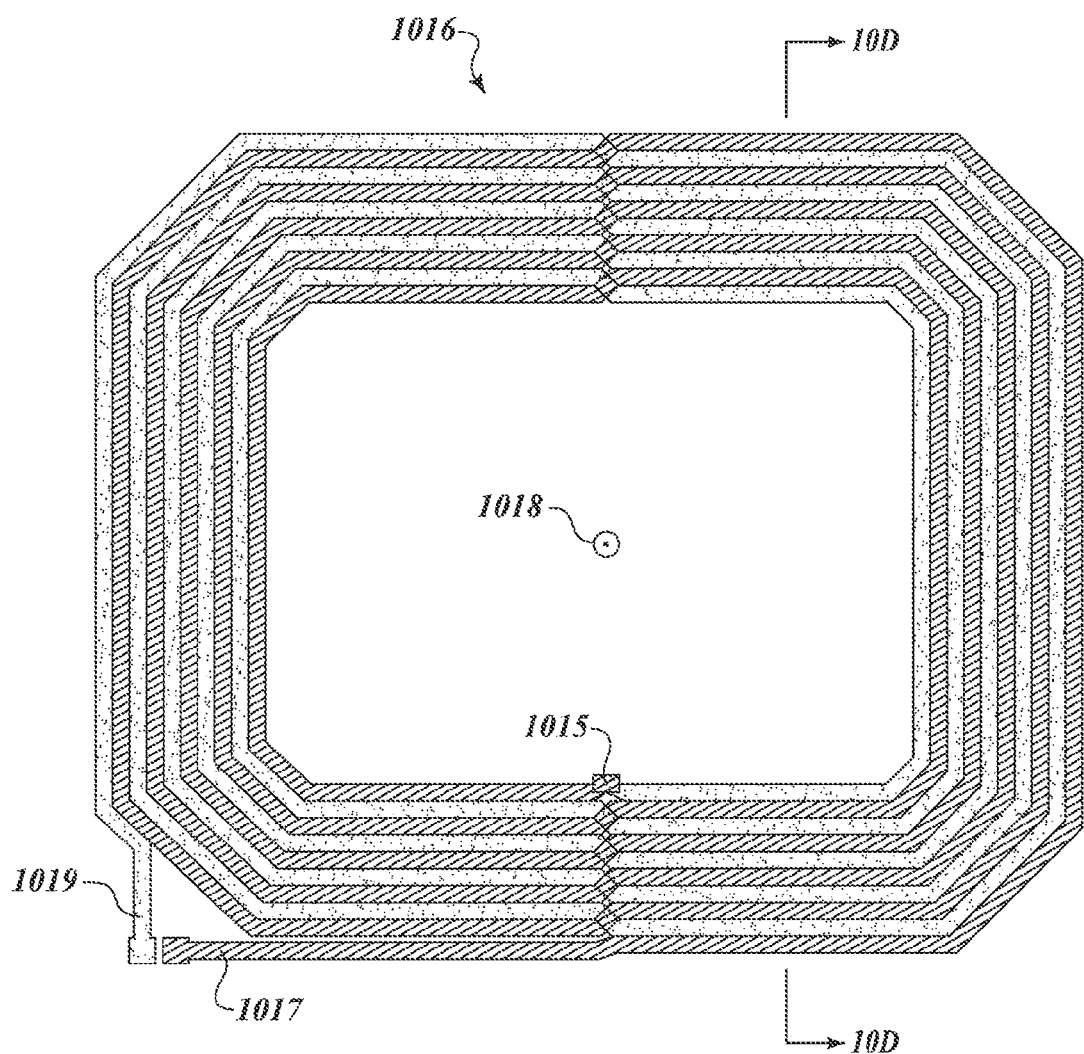
FIG. 10A is an enlarged top plan view of an antenna according to one illustrated embodiment, wherein the antenna is formed of a top coil of conductive material and a bottom coil of conductive material.
Figure 10B:
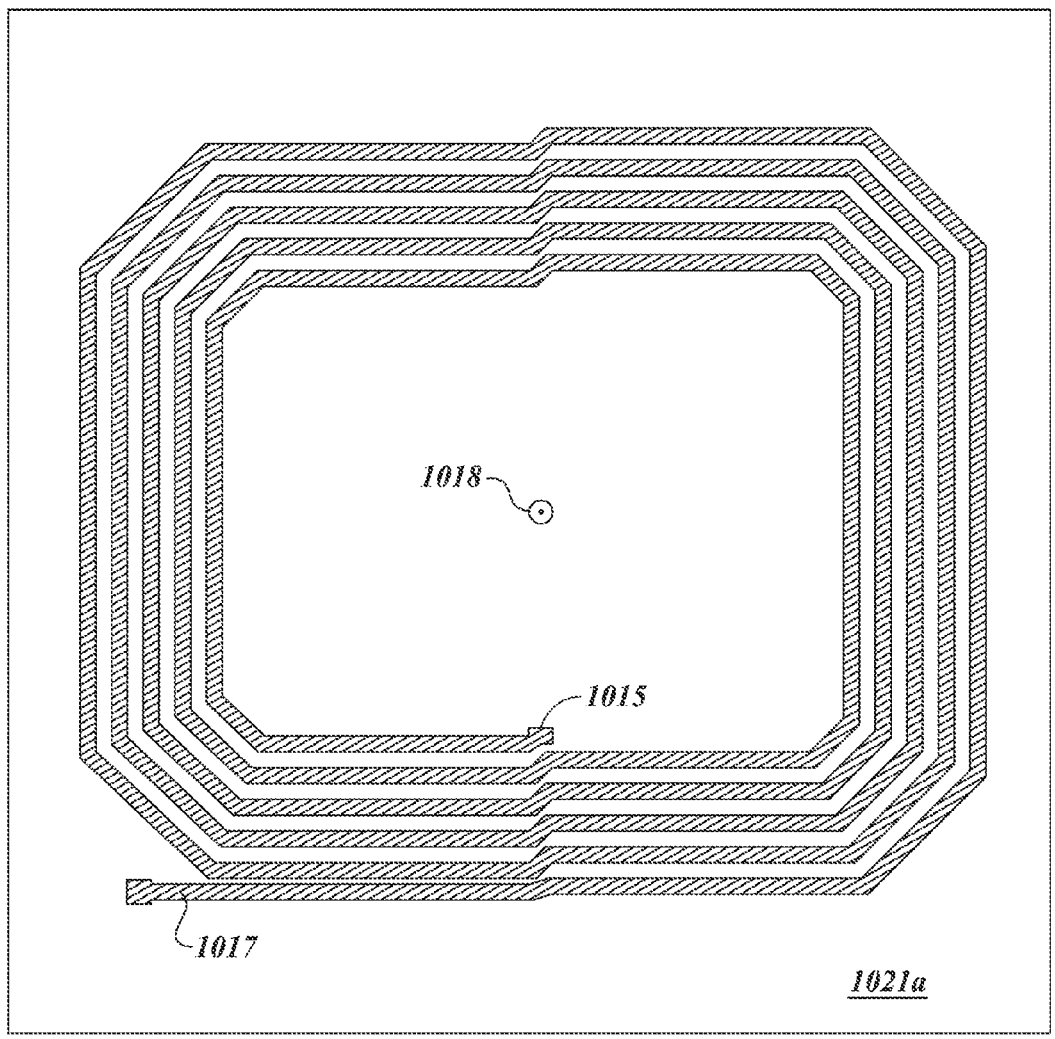
FIG. 10B is an enlarged top plan view of the top coil of the antenna FIG. 10A.
Figure 10C:
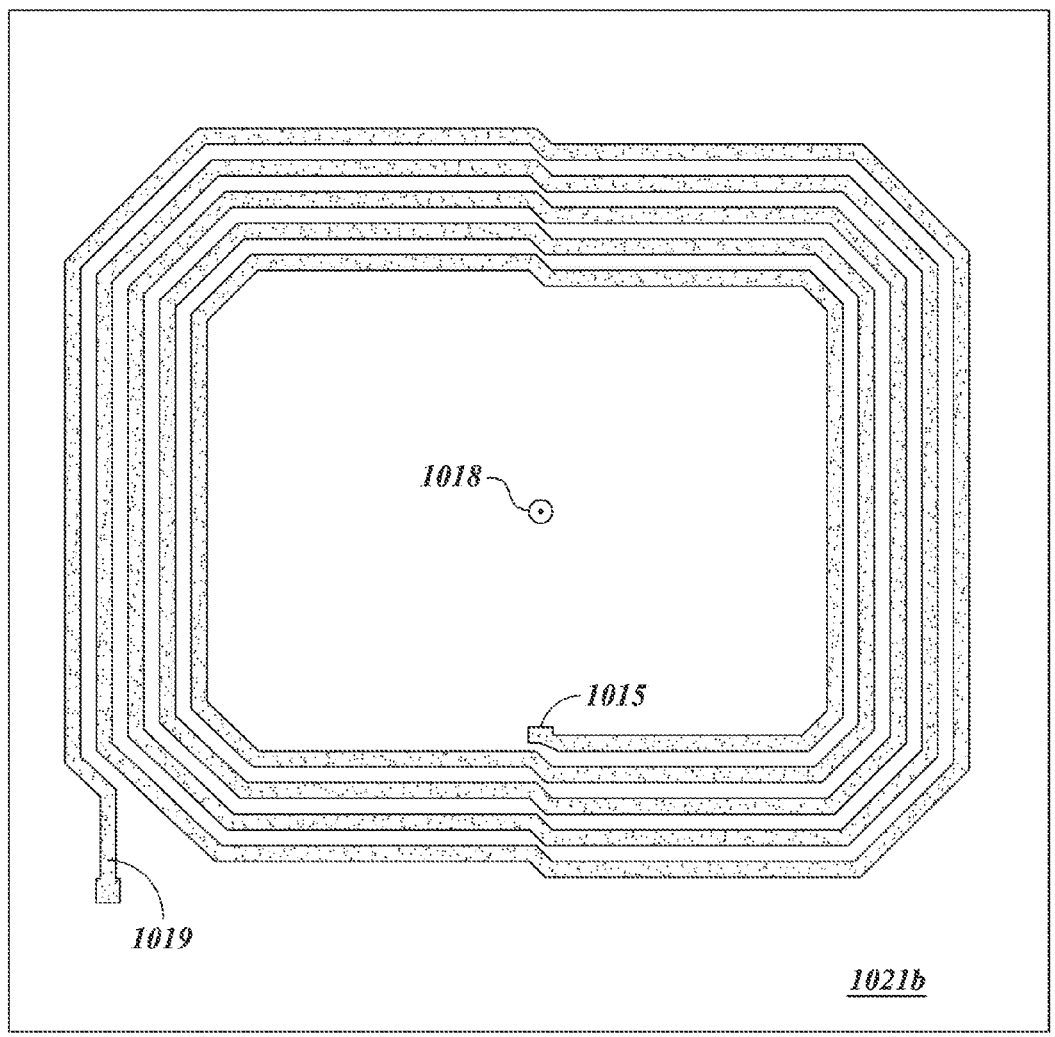
FIG. 10C is an enlarged top plan view of the bottom coil of the antenna FIG. 10A.

FIGS. 10A-10C illustrate a coil antenna 1016 according to one embodiment.

The coil antenna 1016 comprises a top coil 1017 (illustrated in isolation in FIG. 10B) and a bottom coil 1019 (illustrated in isolation in FIG. 10C). The top and bottom coils 1017, 1019 are carried by the patient support surface 26, the top coil 1017 carried on one layer 1021a and positioned relatively above the bottom coil 1019 carried on another layer 1021b. The top coil 1017 is electrically coupled to the bottom coil 1019, for example, by a plug of electrically conductive material 1015 in a via. In practice the via connecting the top coil 1017 to the bottom coil 1019 may comprise a vertical connector of the same material as the coils 1017, 1019. Any suitable conductor may be used to connect the top coil to the bottom coil at the via point. In addition to being offset from each other vertically along a longitudinal axis 1018 of the coils (see FIG. 10D), the individual windings of the two coils are also offset from each other laterally along two perpendicular axes in a horizontal plane (La, the plane of the drawing sheet FIG. 10A) that is perpendicular to the longitudinal axis. The layers 1021a, 1021b may be opposed outer surfaces of an electrically insulative substrate, one or more inner surfaces of the electrically insulative substrate, or a combination thereof. The electrically insulative substrate may be a unitary part of the patient support surface, integral part of the patient support surface or attach or carried by the patient support surface.

Figure 10D:
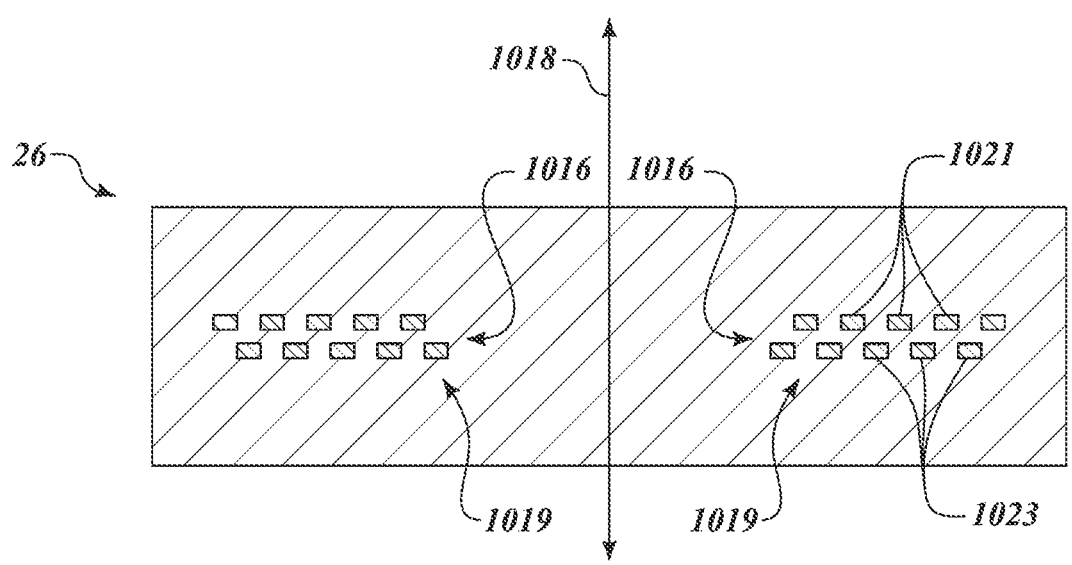
FIG. 10D is a cross-sectional view of a portion of a patient support structure carrying the top and bottom coils of the antenna of FIG. 10A, according to one illustrated embodiment.

FIG. 10D shows the coil antenna 1016 carried by a patient support structure 26, according to one illustrated embodiment.

Top coil 1017 is positioned relatively above the bottom coil 1019 in an interior of the patient support structure 26. As noted above, the bottom coil 1019 is offset from the top coil 1017 vertically along a longitudinal axis 1018 as well as laterally in a horizontal plane which is perpendicular to the longitudinal axis 1018. The individual windings 1021 of the top coil 1017 are spaced apart leaving gaps between each winding 1021. The individual windings 1023 of the bottom coil 1019 are spaced directly below the gaps between the windings 1021 of the top coil 1017. The windings 1021, 1023 are thus spread in such a way to provide a more even distribution of radiolucence. This distribution of the windings 1021, 1023 may smooth the contrast that could appear in a radiological image (e.g., X-ray image). FIG. 10D illustrates an embodiment in which the windings 1023 are spaced directly below the gaps between windings 1021 without overlapping the windings 1021 in a lateral direction in the horizontal plane. In other embodiments the windings 1023 may instead slightly overlap the windings 1021. In some embodiments the windings 1021, 1023 may cross over each other although such crossings may have an adverse effect on radio transparency. Many other configurations of the coils 1017, 1019 and the windings 1021, 1023 will be apparent to those of skill in the art and fall within the scope of this disclosure. The configuration of windings illustrated in FIG. 10D are given only by way of example and do not limit the scope of the disclosure. The patient support structure 26 and antenna 1016 are not drawn to scale. Relative heights, widths, and separations of the patient support structure 26 and antenna coils 1017, 1019 may be different in practice than what is shown in FIG. 10D.

This design may minimize interference with radiological imagery sources (e.g., X-rays, CAT scans, MRIs) which may be employed while a patient is on the patient support structure 26. Radiological imaging is commonly employed while patients are on the patient support structure 26, for example during surgery. This may, for example, be performed by positioning an X-ray machine above the patient support structure 26 and positioning an X-ray sensitive film below the patient support structure 26. An X-ray image is formed by exposing the film to the X-rays through the patient and patient support structure 26. Any object or material that absorbs or reflects X-rays more than its surroundings will cause an area of contrast in the developed X-ray image. Thus, portions of the patient support 26 structure that absorb more or less than other portions of the patient support structure 26 will appear as a high level of contrast in the developed X-ray image. This can make it difficult to interpret the X-ray image. For this reason it may be beneficial to spread the coils of an antenna, even where nominally radio transparent to reduce the contrast which the antenna may otherwise cause in an X-ray image. A coil antenna with many windings which are stacked or layered are above others may produce a relatively high contrast and appear in an X-ray image even if a single layer of coil is nominally radio transparent. A coil whose windings are spread apart, spread laterally from one another, may also produce relatively large changes in contrast, even where nominally radio transparent. As disclosed herein, the windings of the coils are positioned to be in adjacent non-overlapping relationship to one another when viewed along the longitudinal axis 1018. Such creates an area having a very uniform distribution of antenna material, and hence a very uniform radiological attenuation distribution across that area. Such advantageously may cause any attenuation to be uniform, reducing the antenna's effect on the radiological image.

Figure 10E:
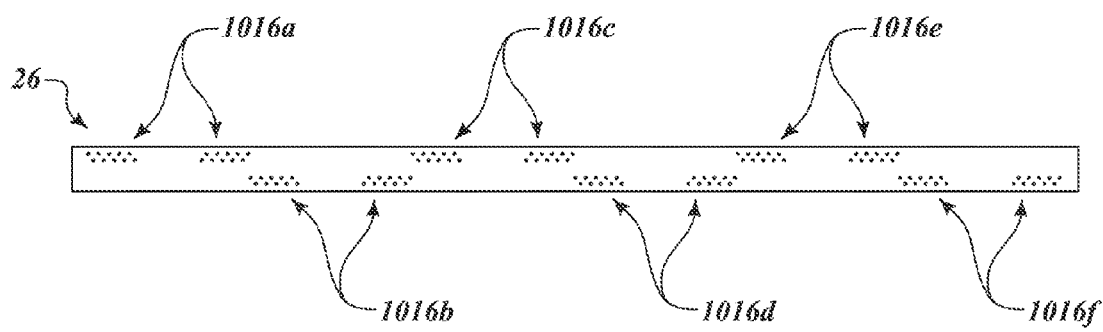
FIG. 10E is a cross-sectional view of a patient support structure with a plurality of antennas, according to another illustrated embodiment.
Figure 10F:
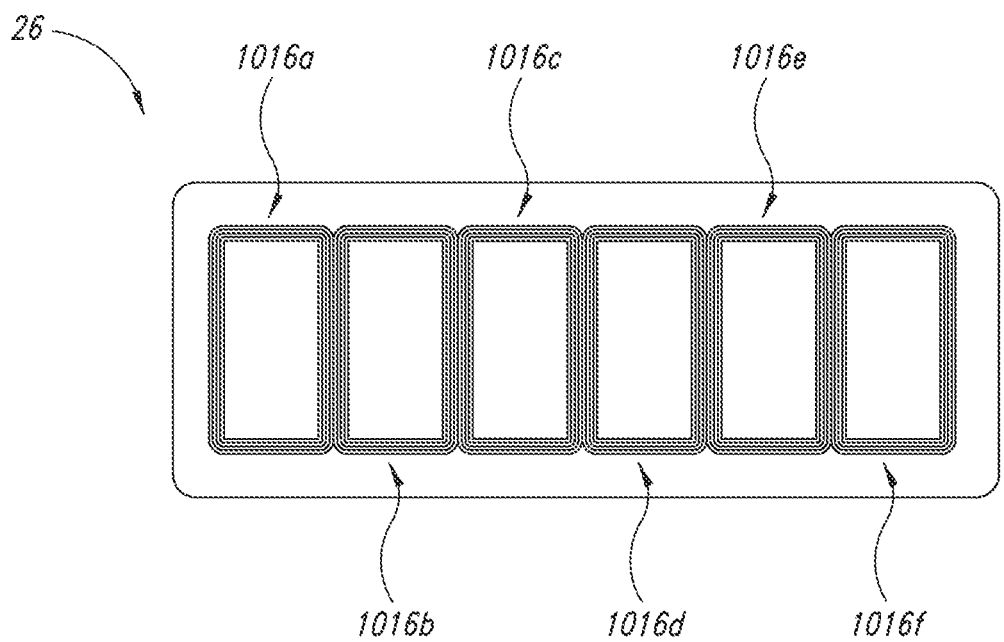
FIG. 10F is a top plan view of a patient support structure comprising a plurality of antennas, according to still another illustrated embodiment.

FIGS. 10E and 10F show a patient support structure 26 according to one embodiment.

The patient support structure carries six antennas 1016a-1016f. Each of the antennas 1016a-1016f may be similar or identical in form to the antenna 1016 illustrated in FIG. 10A-10D. The antennas 1016a-1016f are positioned to provide little or no gap between antennas in the lateral directions of the horizontal plane of the patient support surface 26, while not overlapping. As described above, this configuration may help to reduce areas of sharp contrast in radiological images. FIG. 10E shows the antennas 1016a-1016f embedded within the patient support structure 26. Of course the antennas 1016a-1016f may not actually be visible from a top view of the support structure 26. However, FIG. 10F shows the antennas 1016a-1016f from the top view to illustrate the relative positions of the antennas 1016a-1016f. The number and configuration of coils, as well as the number and configuration of the winding forming those coils, shown in FIG. 10F is not meant to be limiting. In practice there may be a greater or lesser number of coils and/or a greater or lesser number of windings. In practice, the windings are typically not independent loops, but are illustrated as such in FIG. 10F for ease of illustration.

Figure 11:
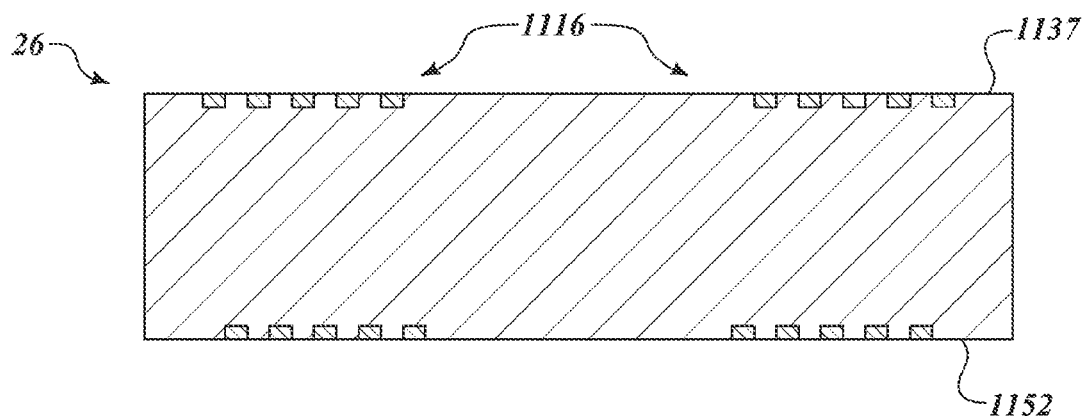
FIG. 11 is a cross-sectional view of a portion of a patient support structure with an antenna carried in opposed surfaces thereof, according to yet still another illustrated embodiment.

FIG. 11 shows a patient support structure carrying an antenna 1116, according to another illustrated embodiment.

The antenna 1116 comprises a top coil 1117 and a bottom coil 1119 as previously described. The top coil 1117 comprises windings 1121, while the bottom coil comprises windings 1123. The windings 1121, 1123 are laterally offset from each other in two perpendicular directions in a horizontal plane that is perpendicular to a longitudinal axis of the antenna 1116. The top coil 1117 is formed adjacent to and below a top surface 1137 of the support structure 26, for example in a channel or recess formed in the top section 1137. The bottom coil 1119 is formed above and adjacent to a bottom surface 1152 of the support structure 26, for example, in a channel or recess formed in the bottom section 1152.

Figure 12:
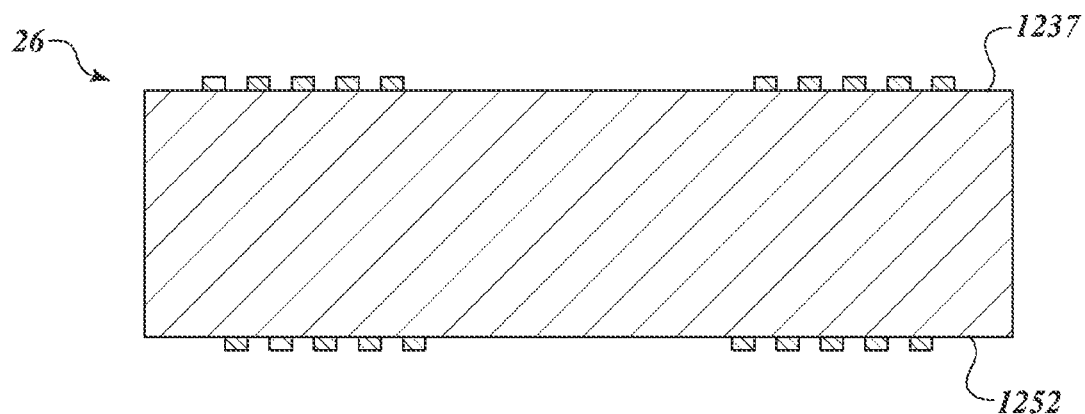
FIG. 12 is a cross-sectional view of a portion of a patient support structure an antenna of FIG. 10A carried on opposed surfaced thereof, according to even another illustrated embodiment.

FIG. 12 illustrates a patient support structure that carries an antenna 1126, according to yet another illustrated embodiment. The antenna 1216 comprises a top coil 1217 and a bottom coil 1219. The top coil 1217 comprises windings 1221, while the bottom coil comprises windings 1223. The windings 1221, 1223 are laterally offset from each other in a horizontal plane that is perpendicular to a longitudinal axis of the antenna 1216. The top coil 1217 is carried directly on a top surface 1237 of the support structure 26. The bottom coil 1219 is carried directly on a bottom surface 1252 of the support structure 26. The top and/or bottom coils 1217, 1219 may be adhered or otherwise physically coupled to the respective surfaces 1237, 1252. The relative dimensions of the features shown in FIG. 12 may not be accurate. For instance, the antenna windings 1221, 1223 may not, in practice, protrude from the surfaces 1237, 1252 to the same extent as illustrated. Many other configurations for the antennas are possible and the preceding embodiments are given only by way of non-limiting example.

Figure 13A:
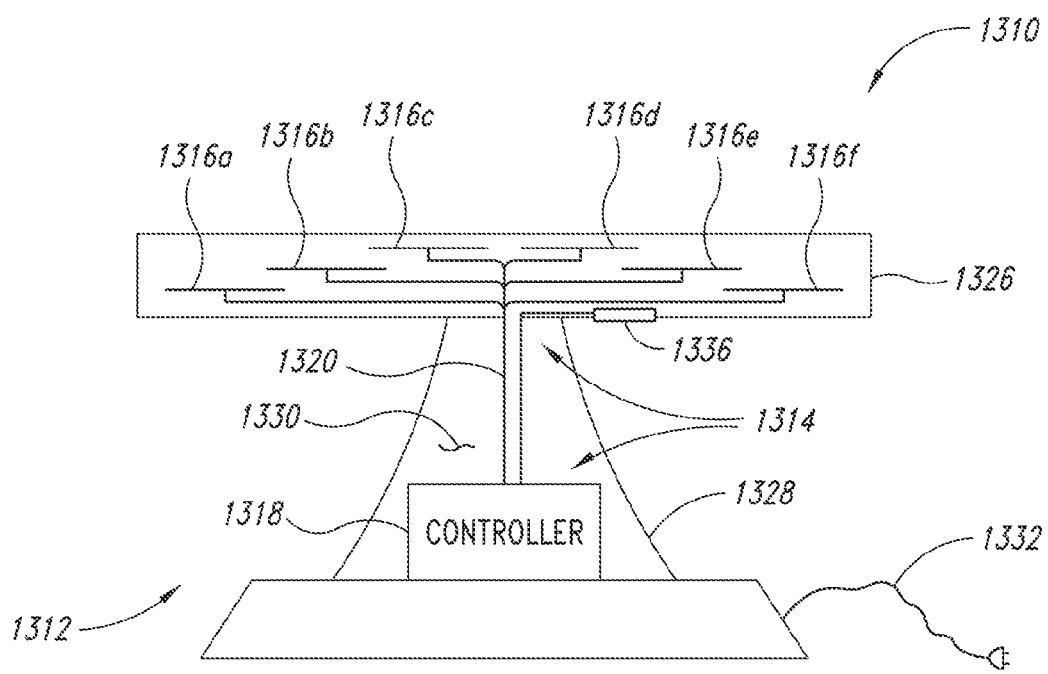
FIG. 13A is a schematic diagram showing a surgical table with a plurality of antennas and a controller positioned in a pedestal of the surgical table, according to another illustrated embodiment.

FIG. 13A shows a surgical environment 1310 that includes a surgical table 1312 and an interrogation and detection system 1314, according to another illustrated embodiment. The embodiment of FIG. 13A is similar in some respects to one or more of the previously described embodiments, hence only significant differences in structure and operation will be discussed.

The surgical table 1310 may include a patient support structure 1326 and a pedestal or base 1328. The patient support structure 1326 may be a laminate structure having multiple layers. Alternatively, the patient support structure 1326 may be a shell type structure or housing having an open interior. Alternatively, the patient support structure 1326 may be a solid structure, for example a roto-molded structure.

The plurality of antennas 1316a-1316f (collectively 1316) of the interrogation and detection system 1314 are carried by the surgical table 1312, for example carried by inner layers of the patient support structure 1326 or positioned in an interior of a shell or housing forming the patient support structure 1326. While illustrated as being in overlapping relationship, in some embodiments the antennas 1316 may not overlap. The controller 1318 of the interrogation and detection system 1314 may be positioned in the pedestal or base 1328, for example in an interior 1330 of the pedestal or base 1328. One or more wired or wireless communication paths may communicatively couple the controller 1318 to the antennas 1316 and/or to an interrogation and detection system interface 1336, for example coaxial cable 1320.

The interrogation and detection system 1314 may receive power for a variety of sources, for example from a wall outlet or receptacle via a conventional power cord and plug 1332.

The antennas of the interrogation and detection system 14 are not limited to being implemented in a patient support structure 26. Previous embodiments have, by way of example, described various ways of implementing antennas within a patient support structure. These embodiments have been given purely by way of example and are not intended to be limiting. Those of skill in the art will recognize that the antennas may be implemented in many configurations throughout the environment in which medical procedures are performed.

Figure 13B:
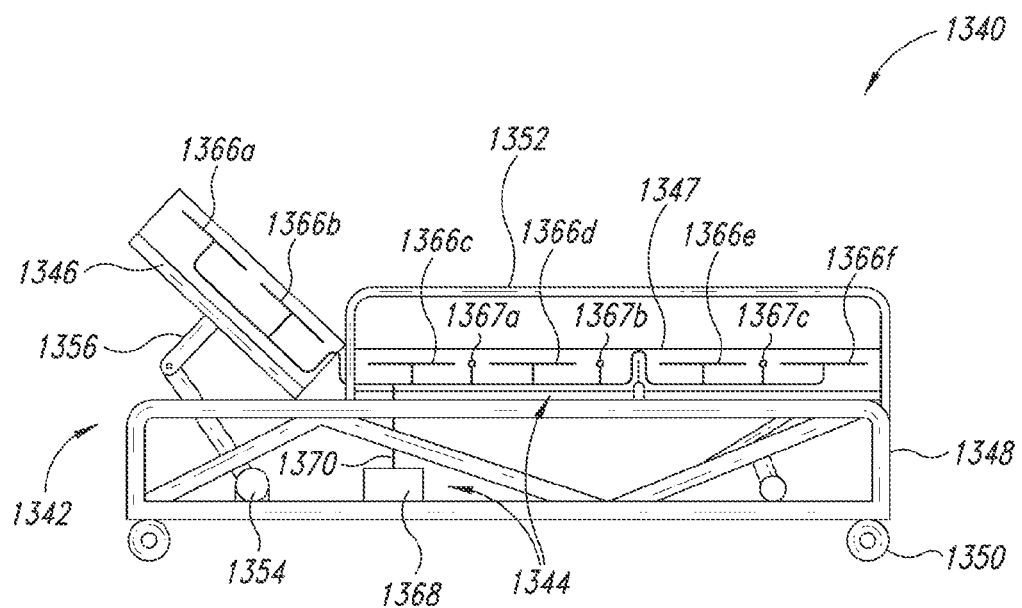
FIG. 13B is a schematic diagram showing a bed such as a patient bed used in an environment where medical procedures are preformed, the bed including a plurality of antennas and a controller positioned on a frame of the bed, according to another illustrated embodiment.

FIG. 13B shows an environment in which medical procedures are performed 1340 that includes a bed (e.g., patient bed) 1342 and an interrogation and detection system 1344, according to another illustrated embodiment. The embodiment of FIG. 13B is similar in some respects to one or more of the previously described embodiments, hence only significant differences in structure and operation will be discussed.

The environment 1310, may for example, take the form of a hospital room, clinic room, or examination room of a medical practitioner's office.

The bed 1342 may include a patient support structure 1346 and a frame or base 1348. The patient support structure 1346 may support one or more mattresses, for example a segmented mattress 1347. The frame 1348 may be made of plastic, metal, composite, reinforced composited, and/or roto-molded materials. Various commercially available designs of frames for patient beds are suitable. The frame 1348 may include a set of wheels 1350 (only one called out in FIG. 13B) allowing the bed 1342 to be easily moved. The frame 1348 may include one or more rails 1352, which may, or may not, be removable or which may, or may not, fold down.

The bed 1342 may include one or more electric motors 1354 (only one called out in FIG. 13B) and linkages 1356 (only one called out in FIG. 13B) which are selectively actuated to move or articulate portions of the bed 1342 or mattress 1346. Other mechanisms may be used to move portions of the mattress 1346. Commercially available patient or hospital beds 1342 typically include one or more pieces of electrical or electronic equipment (e.g., electric motors 1354) which are sources of radio noise which may interfere with the interrogation and detection system 1344. Such equipment typically produce very consistent or periodic (i.e., non-random) noise. Some embodiments of the interrogation and detection system 1344 discussed herein employ various techniques to address such non-random noise.

The interrogation and detection system 1344 includes a plurality of antennas 1366a-1366f (collectively 1366) of the interrogation and detection system 1344 are carried by the patient support structure 1346, mattress 1347 or frame 1348. For example, the antennas 1366 may be carried by inner layers of the mattress 1347 or positioned in an interior of a shell or housing forming the patient support structure 1346. While illustrated as being in non-overlapping relationship, in some embodiments the antennas 1366 may overlap. A controller 1368 of the interrogation and detection system 1344 may be carried by the frame or base 1348. One or more wired or wireless communication paths may communicatively couple the controller 1368 to the antennas 1366 and/or to an interrogation and detection system interface, for example coaxial cable 1370.

The interrogation and detection system 1314 may receive power for a variety of sources, for example from a wall outlet or receptacle via a conventional power cord and plug (not shown in FIG. 13B).

In some embodiments, antennas, for instance antennas 1316, 1366 (FIGS. 13A, 13B, respectively) may form strain sensors as part of a strain gauge. For example, the antennas may be carried by flexible substrate, for instance a flexible printed circuit board such as a polyimide (Kapton®) or polyester (Mylar®) printed circuit board. The resistance of the antenna varies as the substrate flexes. The change in resistance may be measured to determine strain, and hence force applied. The antennas may be configured and coupled in groups of fours to form full Wheatstone bridges. The antennas may additionally, or alternatively, be oriented along various axes or dimensions to detect strain in different directions. Multiple layers of antennas may be employed to detect flex in two opposite directions, normal to the plane of the substrate. Alternatively, dedicated strain sensors or gauges may be employed, which do not function as antennas. Sensing strain may be useful in detecting excessive and/or prolonged pressure asserted between a patient and the patient support surface. Excess and/or prolonged pressure may cause the patient to develop "bed sores" or ulcers. Tracking or monitoring pressure may allow the medical care provider to intervene before the "bed sores" or ulcers occur. Thus, the control system may be configured to provide an warning or alert (e.g., visual, aural and/or tactile) when pressure or strain exceeds some threshold in amplitude and/or time. The control system may additionally, or alternatively, provide an indication of a position or location on the patient support surface or patient where the excessive pressure is occurring.

Additionally, or alternatively, one or more dedicated force sensors (e.g., strain or pressure sensors) 1367a-1367c (collectively 1367) may be carried by the bed 1342. The sensors 1367 may be located at defined locations where portions of a patient typically experience a high pressure or force. Bed sores or ulcers commonly develop at these areas. While, the precise locations may vary dependent on the size of a patient and/or specific position of a patient in the bed, one or more sensors 1367 may be distributed about areas where specific portions (e.g., hips, buttocks) of a patient would typically be located when on the patient support structure.

Figure 14A:
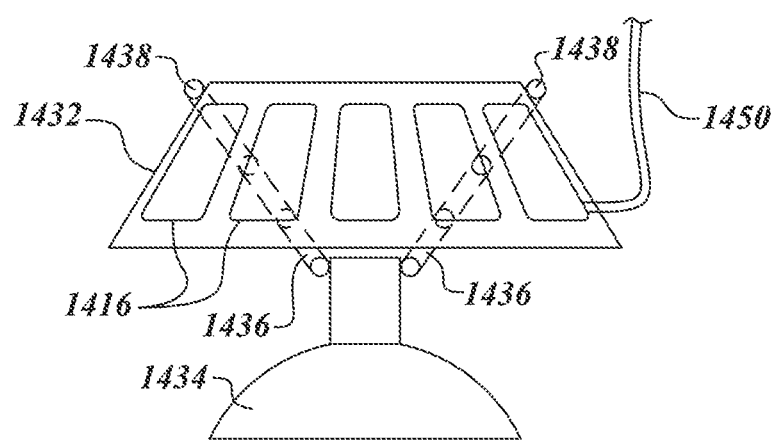
FIG. 14A is a side elevational view of an overhead light fixture for use in a medical procedure and a light shade with several antennas supported by the light fixture, according to one embodiment in which the light shade is shown in a retracted position or configuration of FIG. 10A.

FIG. 14A shows a number of antennas 1416 carried by a lightshade 1432 of a light fixture 1434 used in medical procedures, according to one illustrated embodiment, in which the lightshade is shown in a retracted or undeployed position or configuration. The light fixture 1434 may house one or more lights to be used during surgery, birth delivery or other medical procedure, including dental procedures. During a medical procedures such as surgery, the patient laying on a patient support structure is typically illuminated brightly by an overhead light fixture 1434. The light fixture 1434 may be situated directly above the operating table or slightly offset as desired. The light fixture 1434 is also generally positioned as close to the patient as possible without impeding the medical services providers (e.g., surgeons and staff) during the medical procedure (e.g., surgery, birth delivery). The proximal overhead position allows the light fixture 1434 to brightly illuminate the patient. The light fixture 1434 is positioned so as to reduce or eliminate any shadows on the patient's body during the surgery.

The proximal overhead position of the light fixture 1434 provides an excellent location for the antennas 1416 of an interrogation and detection system. There are five loop antennas 1416 visible in the lightshade 1432 illustrated in FIG. 14A. However, there may be more antennas 1416 on a far side of the lightshade 1432, not visible in FIG. 14A. The number of antennas 1416 located on the lightshade 1432 may be any number suitable for the interrogation process.

Figure 14B:
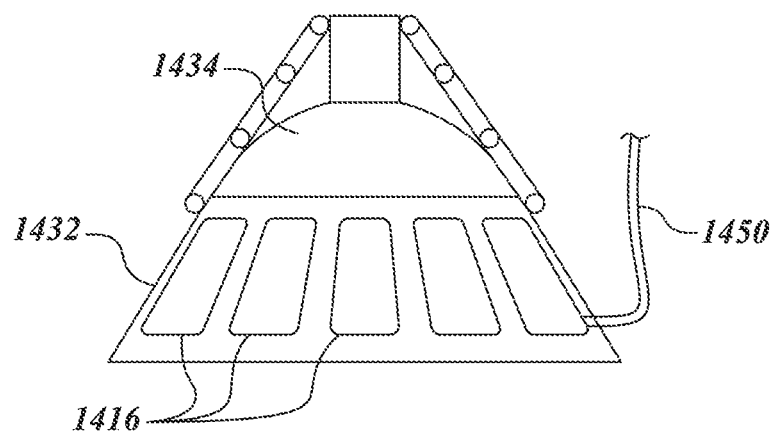
FIG. 14B is a side elevational view of the light fixture and a light shade in which the light shade is shown in an extended position or configuration.

The lightshade 1432 may be attached to the light fixture 1434 by extendable and retractable support arms 1436. As noted, FIG. 14A illustrates the lightshade 1432 in a retracted or undeployed position or configuration, raised relative to the light fixture 1434. The support arms 1436 may include hinges 1438 or other linkages. The hinges 1436 or other linkages enable the lightshade 1432 to be moved to an extended or deployed position or configuration, lowered relative to the light fixture 1434 and the patient support surface, for example, as illustrated in FIG. 14B. In one embodiment the antennas 1416 of the lightshade 1432 may be operable in the raised position. In one embodiment the antennas 1416 may be attached to the light fixture 1434 in a form other than that of a lightshade 1432.

Figure 14C:
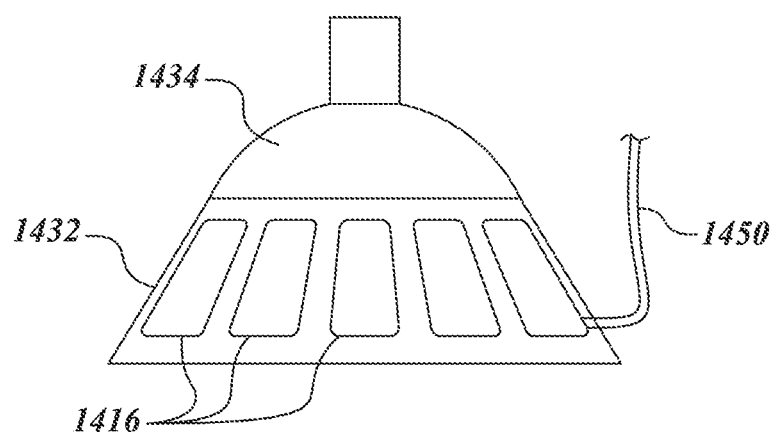
FIG. 14C is a side elevational view of a light fixture for use in a medical procedure and a light shade with several antennas according to another illustrated embodiment.

FIG. 14C shows a lightshade 1432 is coupled to the light fixture 1434 without the use of supporting arms 1436, according to yet another illustrated embodiment.

The lightshade 1432 may be a flexible sheet carrying a number of antennas 1416. The flexible sheet is coupleable to the light fixture 1434 by wrapping the flexible sheet around the light fixture 1434 and securing the flexible sheet thereto. The lightshade 1432 may be attached to the light fixture 1434 by hooks, hook and loop fastener (Velcro®), clips, or any other suitable fasteners or adhesives. Two ends of the lightshade 1432 may be attached to each other to create an opening sized to securely receive a portion of the light fixture 1434 therein. In this configuration the lightshade 1432 remains on the light fixture by virtue of having a smaller diameter opening than a diameter of the portion of the light fixture. The lightshade 1432 may alternatively be an integral part of the light.

In one embodiment, the antennas 1416 of the lightshade 1432 are communicatively coupled to an interrogation and detection system interface 36. The interrogation and detection system interface 36 may be located at any suitable position in the room or in another room. The antennas 1416 may be connected to the system interface 36 by a wired connection (e.g., wire bundle 1450) or a wireless connection. The wire bundle 1450 may run along a ceiling, wall and/or floor of the operating room to communicatively couple with a controller 18. In one embodiment the light fixture 1434 is attached to a mobile support which can be moved about the room or even from one room to another. In one embodiment the system interface 36 is also attached to the light fixture 1434. In one embodiment the controller 18 may be attached to the mobile support of the light fixture 1434 with the antennas 16 directly connected to the controller by 1450.

The function and operation of the interrogation and detection system 14 in embodiments in which the antennas 1416 are coupled to a light fixture 1434 may be substantially the same as those embodiments in which the antennas 1416 are coupled to the patient support structure 26.

While FIGS. 14A, 14B, illustrate the antennas 1416 in a particular non-overlapping configuration, the antennas 1416 may be carried by the lampshade 1432 in any suitable configuration. In contrast to the previously described embodiments in which the patient support structure carried the structures, the lightshade 1432 are unlikely to interfere with radiological imaging. Hence, the antennas 1416 may overlap each other, or may be in a non-overlapping configuration. The antennas 1416 may be attached to one or both exterior surfaces of the lightshade 1432. Alternatively the antennas 1416 may be formed within the lightshade 1432, for example, via lamination or weaving. The lightshade 1432 may be made of any material suitable to not interfere with the function of the antennas 1416.

Figure 15A:
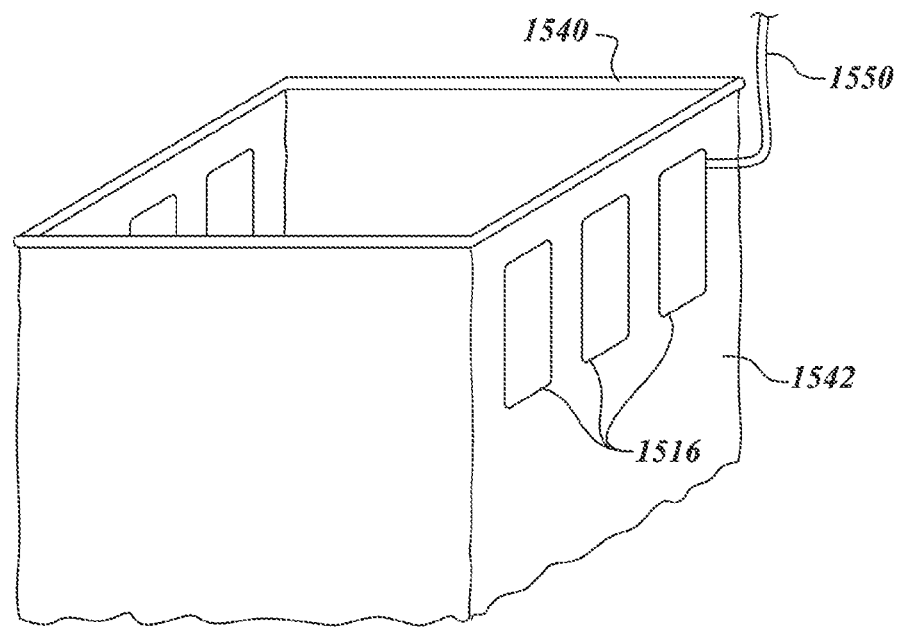
FIG. 15A is an isometric view of a track and a curtain or drape containing several antennas, according to one illustrated embodiment.

FIG. 15A shows a drape or curtain 1542 that carries a number of antennas 1516 according to one illustrated embodiment.

The terms drape and curtain are used interchangeably herein and in the claims. The drape or curtain 1542 may, for example, be used on, over, or in conjunction with a table, bed, frame or other structure during a medical procedure. The drape or curtain 1542 may be coupled to a track 1540 which surrounds a patient support structure 26. The track 1540 is typically in close proximity to the patient support structure and affords a suitable location for the antennas 1516 of the interrogation and detection system 14. In one embodiment, the track may be fastened to a ceiling of a room, for example an operating room, patient room or physician's office or examination room. In such an embodiment, a wire bundle 1550 may also be attached to the ceiling as the wire bundle runs to the system interface 36 or controller 18 situated elsewhere in the surgical environment. The system interface 36 and controller 18 may be attached to a wall of the environment or may be in any other suitable location within the environment in which medical procedures are performed. In another embodiment, the track 1540 may be supported by a freestanding structure or structure fixed or coupled to a floor of the room such as a frame.

The antennas 1516 may be carried on either exterior surface of the drape or curtain 1542 or be situated (e.g., laminated) within the drape or curtain 1542. While FIG. 15A shows the antennas 1516 on two opposing sides of the patient support structure 26, the antennas 1516 may be positioned on a few or greater number sides of the patient support structure 26 while in use. The drape or curtain 1542 may be selectively deployed and retracted along the track 1540 during use. For example, the drape or curtain 1542 may be retained in a retracted, undeployed position or configuration during times or periods when scanning or interrogation is not being performed. The drape or curtain 1542 may be moved to an extended, deployed position or configuration in preparation for scanning or interrogation, for example, just prior to completing the medical procedures (e.g., surgery) and, for example closing the patient. In other embodiments, the drape or curtain 1542 may be retained in the extended or deployed position or configuration throughout the surgical procedure. The antennas 1516 may be connected to system interface 36 by means of the wire bundle 1550 extending from the curtain 1540.

Figure 15B:
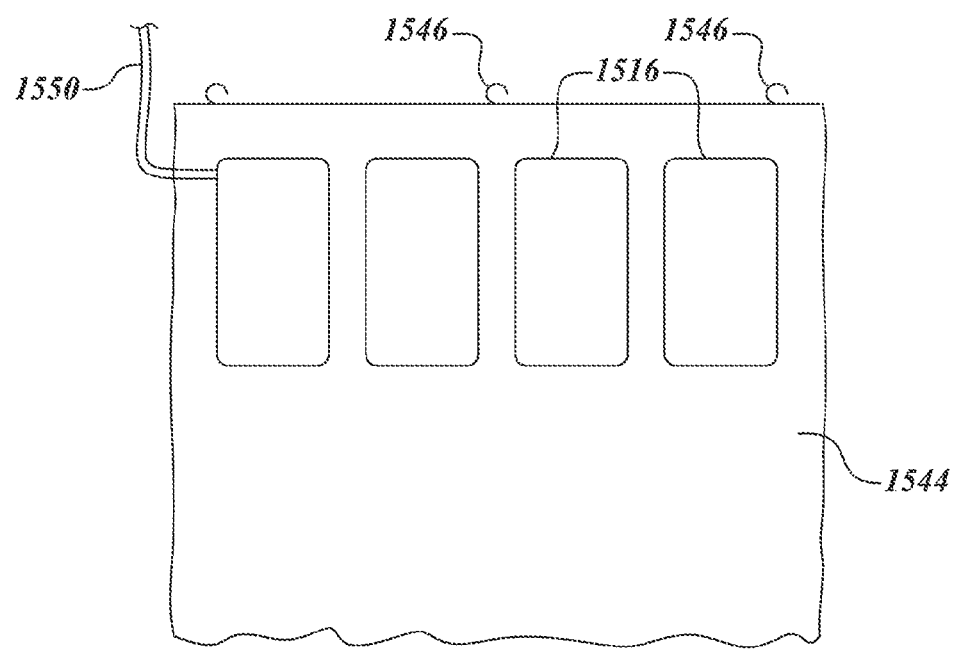
FIG. 15B is a side elevational view of a sheet containing several antennas and configured to be hung from a support according to one embodiment.

FIG. 15B shows a sheet 1544 carrying a number of antennas 1516 which sheet 1544 may be quickly hung on a rack or frame 1540. The term sheet is used interchangeably herein and in the claims the terms drape or curtain. The term rack is used herein and in the claims interchangeably with the term frame. The sheet 1544 can be hung from the rack 1540 by connectors 1546. More than one sheet 1544 may be hung from the rack 1540 on one or more sides of the patient support structure 26. The antennas 1516 may be attached on either exterior surface of the sheet 1544 or be situated (e.g., laminated or woven) within the sheet 1544. While the sheet 1544 is illustrated as having four antennas 1516, there may be as few or as many antennas 1516 on the sheet as desired. Connectors 1546 may include hooks, clamps, or any other fastener suitable to attach the sheet 1544 to the rack 1540. The antennas 1516 may be connected to the system interface 36 by means of a wire bundle 1550 extending from the sheet 1544.

Figure 16:
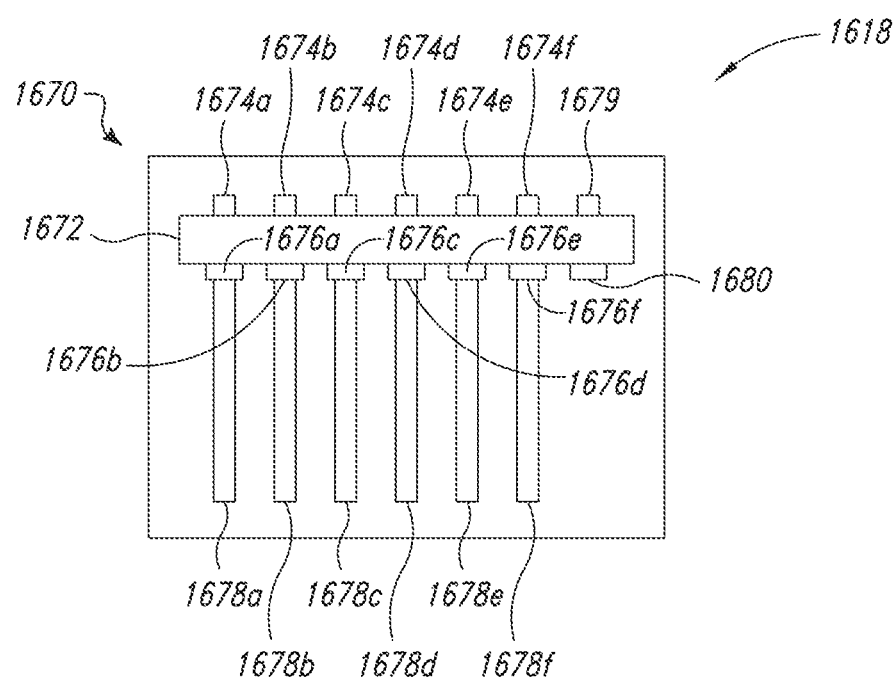
FIG. 16 is a schematic diagram of a controller, according to one illustrated embodiment, including a motherboard and a plurality of plug-in boards, one for each of the antennas.

FIG. 16 shows a controller 1618, according to one illustrated embodiment.

The controller 1618 may include a housing 1670. The housing 1670 may contain a motherboard 1672 with a number of ports or connectors 1674a-1674f (collectively 1674) to communicatively couple the motherboard 1672 to respective ones of the antennas (e.g., antennas 16). The motherboard 1672 may also include a number of slot connectors 1676a-1676f (collectively 1676) to physically receive respective plug-in boards 1678a-1678f (collectively 1678) and communicatively couple the plug-in boards 1678 to the motherboard 1672. There may, for example be one plug-in board 1678 for each antenna, each of the antennas 16 and plug-in boards 1678 constituting a separate channel. The motherboard 1672 may include additional slot connectors, allowing expansion or use with different antenna configurations or different patient support structures (e.g., surgical tables, patient beds). The plug-in boards 1678 may each carry one or more circuits (e.g., analog and/or digital circuit components) configured to transmit interrogation signals from the respective antenna and to monitor the antenna for responses to the interrogation signals. For example, the plug-in boards 1678 may implement or carry the circuits disclosed in U.S. patent application Ser. No. 11/759,141 filed Jun. 6, 2007, U.S. Provisional Patent Application Ser. No. 61/056,787 filed May 28, 2008, and U.S. Provisional Patent Application Ser. No. 61/091,667 filed Aug. 25, 2008, with or without change, which patent applications are incorporated herein by reference in its entirety.

The motherboard 1672 may also include one or more ports 1679 to receive control signals, for example from the interrogation and detection system interface 36, 1336 (FIG. 1, FIG. 13A). The motherboard 1672 may also include one or more synchronization circuits 1680 configured to control and synchronize the operation of the various plug-in boards 1678. The synchronization circuit 1680 may be configured to cause one of the plug-in boards 1678 to transmit an interrogation signal from a first antenna, and cause one or more of the other plug-in boards to monitor for a response by a transponder to the interrogation signal. For instance, the synchronization circuit 1680 may cause the plug-in boards 1678 to have all of the antennas monitor for a response to the interrogation signal. Alternatively, the synchronization circuit 1680 may cause the plug-in boards 1678 to have all of the antennas other than the antenna that transmitted a most recent interrogation signal monitor for a response. Such may advantageously allow monitoring sooner than would otherwise be possible since such can avoid the need to allow the transmitting antenna to return to a quiescent state after transmitting before monitoring for a response. The synchronization circuit 1680 may synchronize the plug-in boards 1678 to successively cause the various antennas to transmit, for example starting with an antenna at one end, and successively transmitting from each of the antennas in order along the longitudinal axis 30 (FIGS. 1 and 2). Alternatively, the synchronization circuit may synchronize the plug-in boards 1678 to cause the various antennas to transmit, but not in order along the longitudinal axis 30. As a further alternative, the synchronization circuit 1680 may synchronize the plug-in boards 1678 to cause the transmission of interrogations signals from a subset of the total set of antennas.

While illustrated as a motherboard 1672 and plug-in boards 1678, other embodiments are possible. For example, the various antennas may be controlled by respective circuits integrated into a signal circuit board. Alternatively, the various antennas may be controlled by a single circuit.

Figure 17:
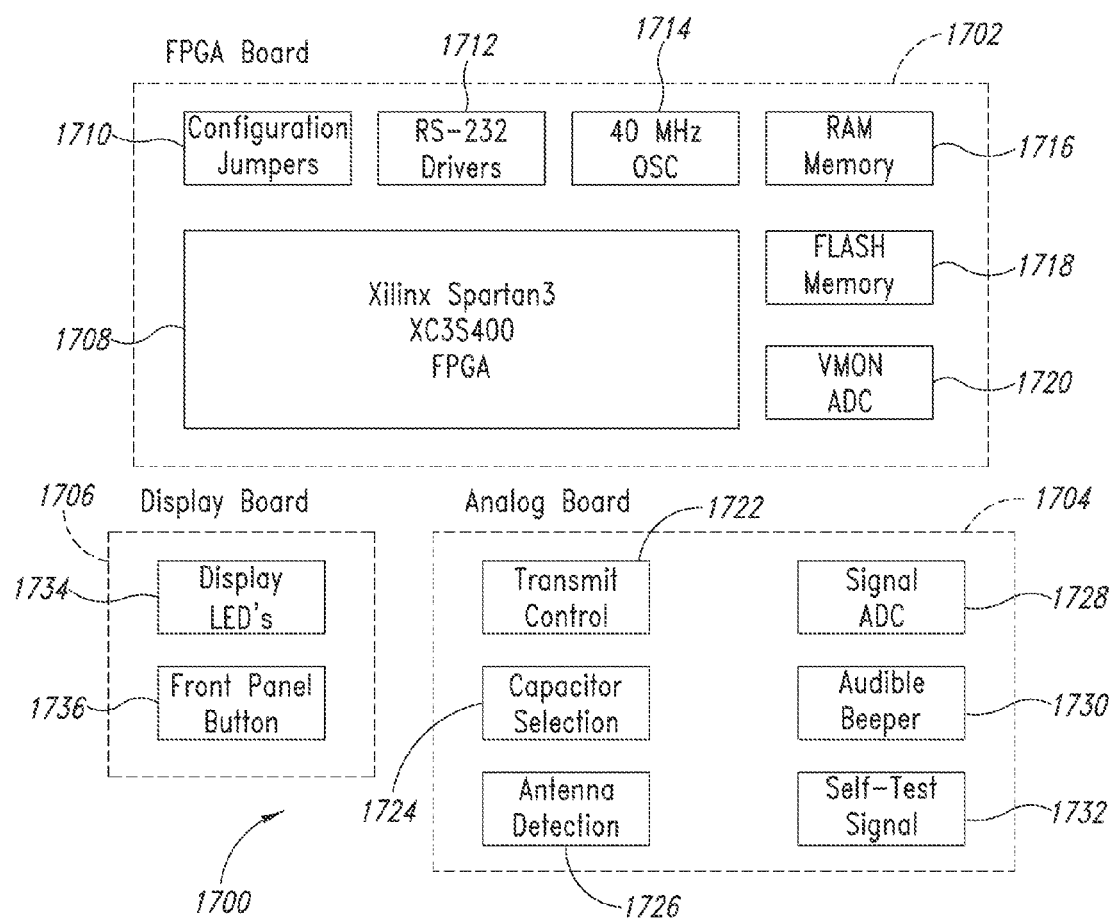
FIG. 17 is a schematic diagram of a portion of a control system of the interrogation and detection system, according to one illustrated embodiment.

FIG. 17 shows a control system 1700 of a controller of an interrogation and detection system, according to one illustrated embodiment.

The control system 1700 includes a field programmable gate array (FPGA) board 1702, one or more analog boards 1704, and a display board 1706, communicatively coupled to one another. The analog board(s) 1704 may take the form of one or more plug-in boards 1678, as discussed in reference to FIG. 16. Hence, there may be a respective analog board 1704 for each of the antennas 16 (FIGS. 1 and 2).

The FPGA board includes an FPGA 1708, configuration jumpers 1710, RS-232 drivers 1712, oscillator 1714, random access memory (RAM) 1716, flash memory 1718, and voltage monitoring (VMON) analog-to-digital converter (ADC) 1720.

The FPGA 108 may take the form of a Xilinx Spartan 3 FPGA, which runs FPGA and application software. As explained below, on power up, the FPGA reads the configuration information and application software program from the flash memory 1718.

The configuration jumpers 1710 are used to select the application software configuration.

The RS-232 drivers 1712 are used to allow the application software to communicate using serial RS-232 data for factory test and diagnostics.

The oscillator 1714 sets the clock frequency for the operation of the FPGA 1708. The oscillator 1714 may, for example, take the form of 40 MHz oscillator, although other frequencies are possible.

The RAM 1716 is connected to the FPGA 1708 and is available for use by the application software. The application software uses this memory space for storage of both the executable program and program data. The RAM 1716 may, for example, have a capacity of 1 MB.

The flash memory 1718 contains both the FPGA configuration data and the binary application program. On power up the FPGA 1708 reads the flash memory to configure the FPGA 1708 and to copy the application program binary data from the flash memory 1718 to the RAM 1702.

The voltage monitor ADC 1720 is connected to the FPGA 1708 and controlled by the application software to monitor a power supply and regulated voltage forms in controller electronics.

The analog board 1704 includes transmit control circuits 1722, capacitor selection circuits 1724, an antenna detection circuit 1726, signal ADC 1728, audible beeper 1730 and self-test signal 1732.

The transmit control circuits 1722 on the analog board 1704 are controlled by signals from the FPGA 1708 to generate a transmit waveform. These signals are denominated as LO_FET_ON and HI_FET_ON, which control the transmit or drive transistors Q1, Q2 (FIG. 18A) along with a signal denominated as DUMP_ON which controls a dump TRIAC (FIG. 18A).

Optional capacitor selection circuits 1724 on the analog board 1704 are controlled by the signals from the FPGA 1708 to tune the drive circuit to match an inductance of the antenna 16 (FIGS. 1 and 2).

The antenna detection circuit 1726 detects when an antenna 16 (FIGS. 1 and 2) is connected to the controller 20. The output of the antenna detection circuit 1726 drives a signal denominated as the LOOP_LEVEL_OUT signal, which is an input to the FPGA 1708.

The signal ADC 1728 is used to sample the signals received at the antenna 16 from the transponders 24 (FIG. 1). The signal ADC 1728 may, for example, operate at a 1 MHz sample rate and may have 12-bits of resolution. The FPGA board 1702 generates the timing and control signals for the signal ADC 1728, which signal are denominated as ADC_CTRL, CS1, SCLK, SD0.

The aural indicator (e.g., speaker or beeper) 42 (FIGS. 1 and 2) can be controlled by the FPGA 1708 to emit sounds to indicate various states, modes or operating conditions to the medical provider.

The FPGA 1708 can cause the generation of the self test signal 1732 on the analog board 1704 at the signal ADC 1728. Self-testing may be performed at start up, and/or at other times, for example periodically or in response to the occurrence of certain conditions or exceptions.

The display board 1706 includes user interface elements, for example a number of visual indicators (e.g., LEDs, LCDs, etc.) 40 (FIGS. 1 and 2). The FPGA board 1702 can control the visual indicators 40 on the display board 1706. The display board 1706 also includes a user selectable activation switch 44, denominated as front panel button 1736. The front panel button 1736 is connected to the display board 1706 which allow the FPGA 1708 to monitor when the front panel button 1736 is activated (e.g., pressed).

Figure 18:
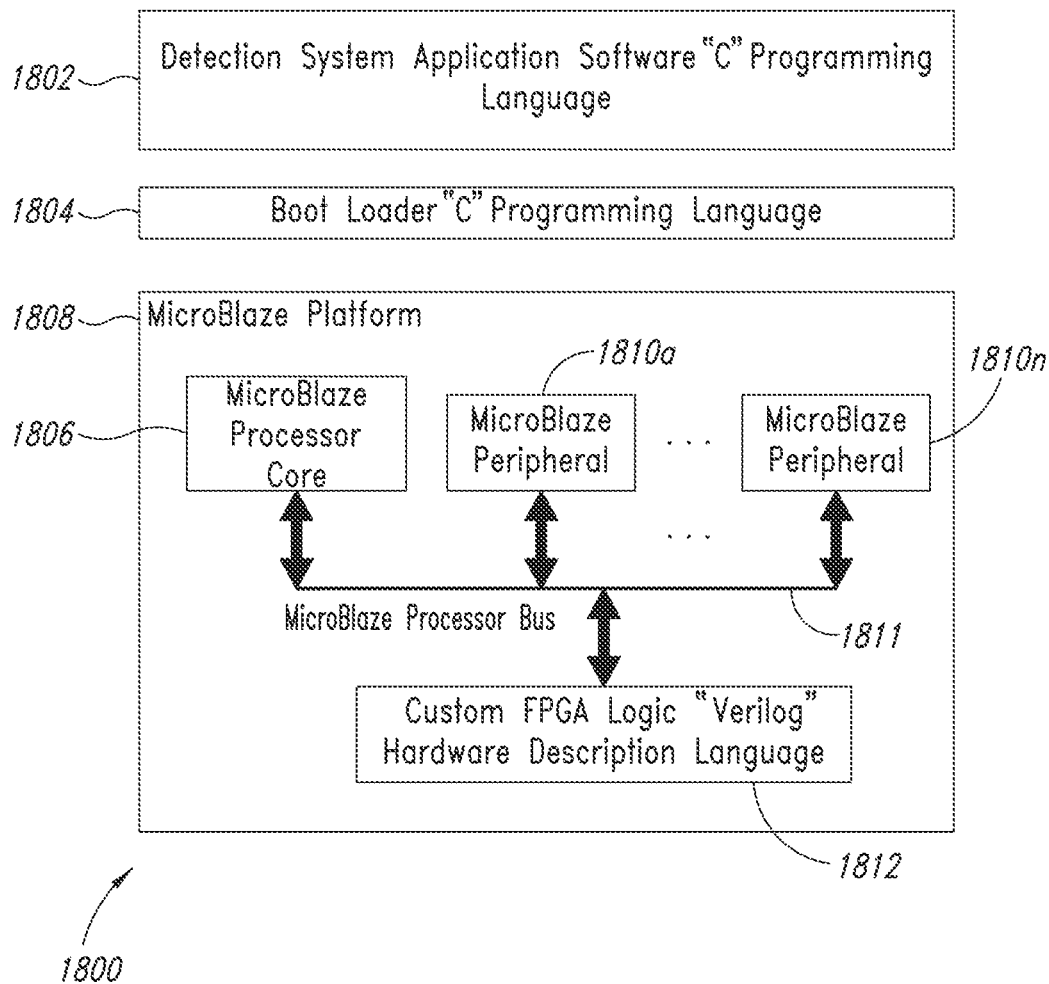
FIG. 18 is a schematic diagram of a software configuration of the interrogation and detection system, according to one illustrated embodiment.
Figure 19A:
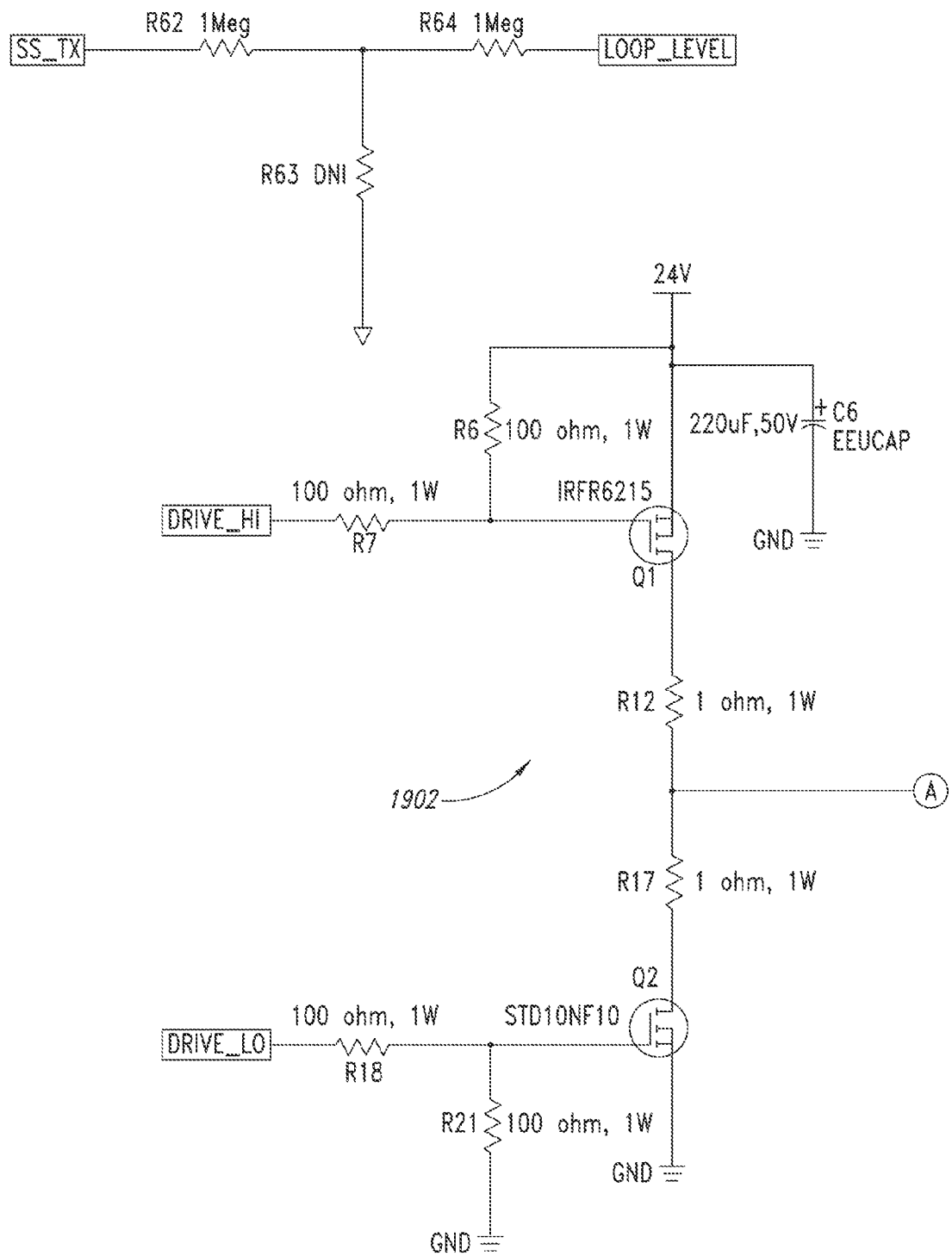
FIGS. 19A-19I are an electrical schematic diagram of the interrogation and detection system including a control circuit and antenna, according to one illustrated embodiment.
Figure 19B:
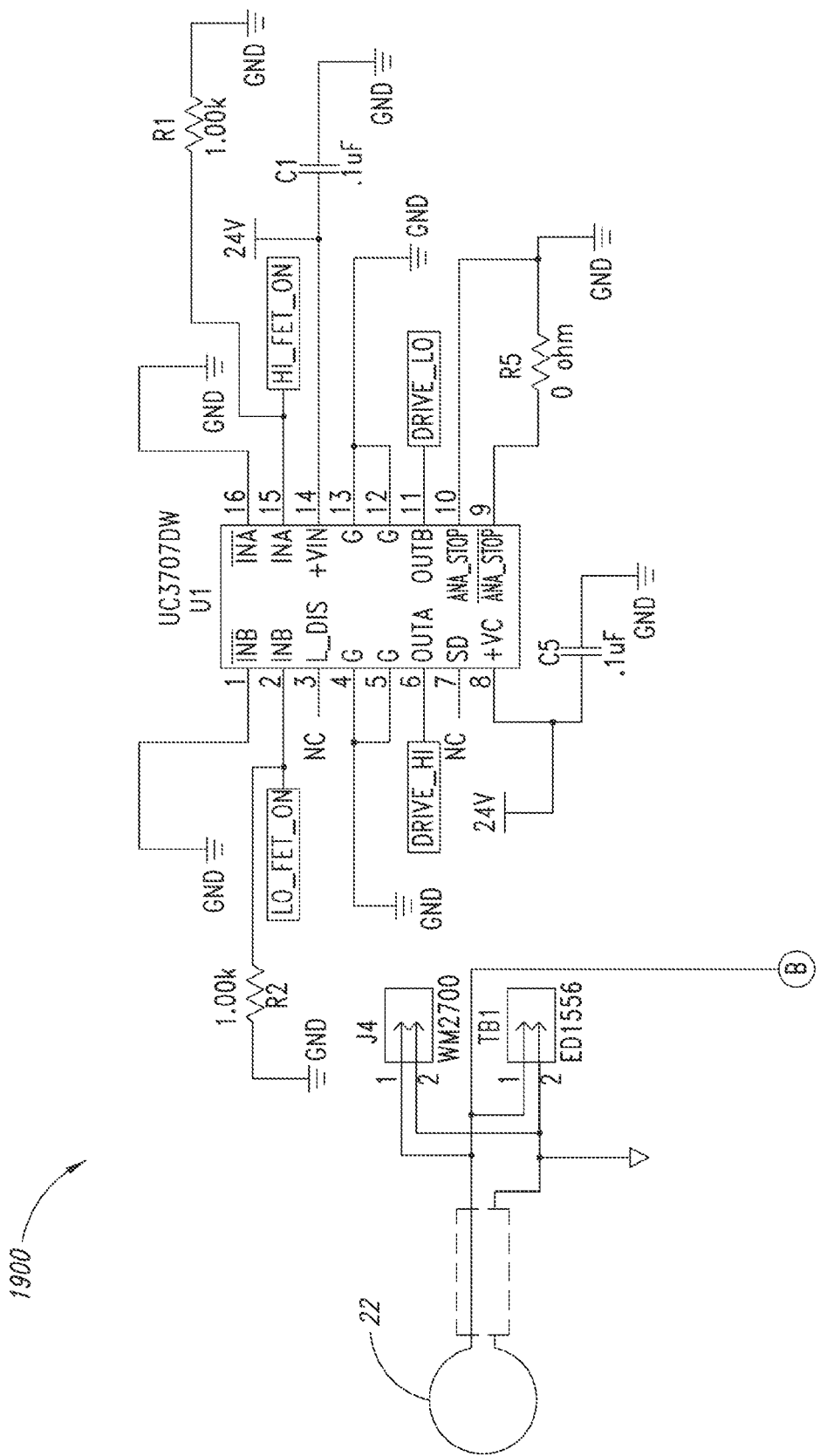
Figure 19C:
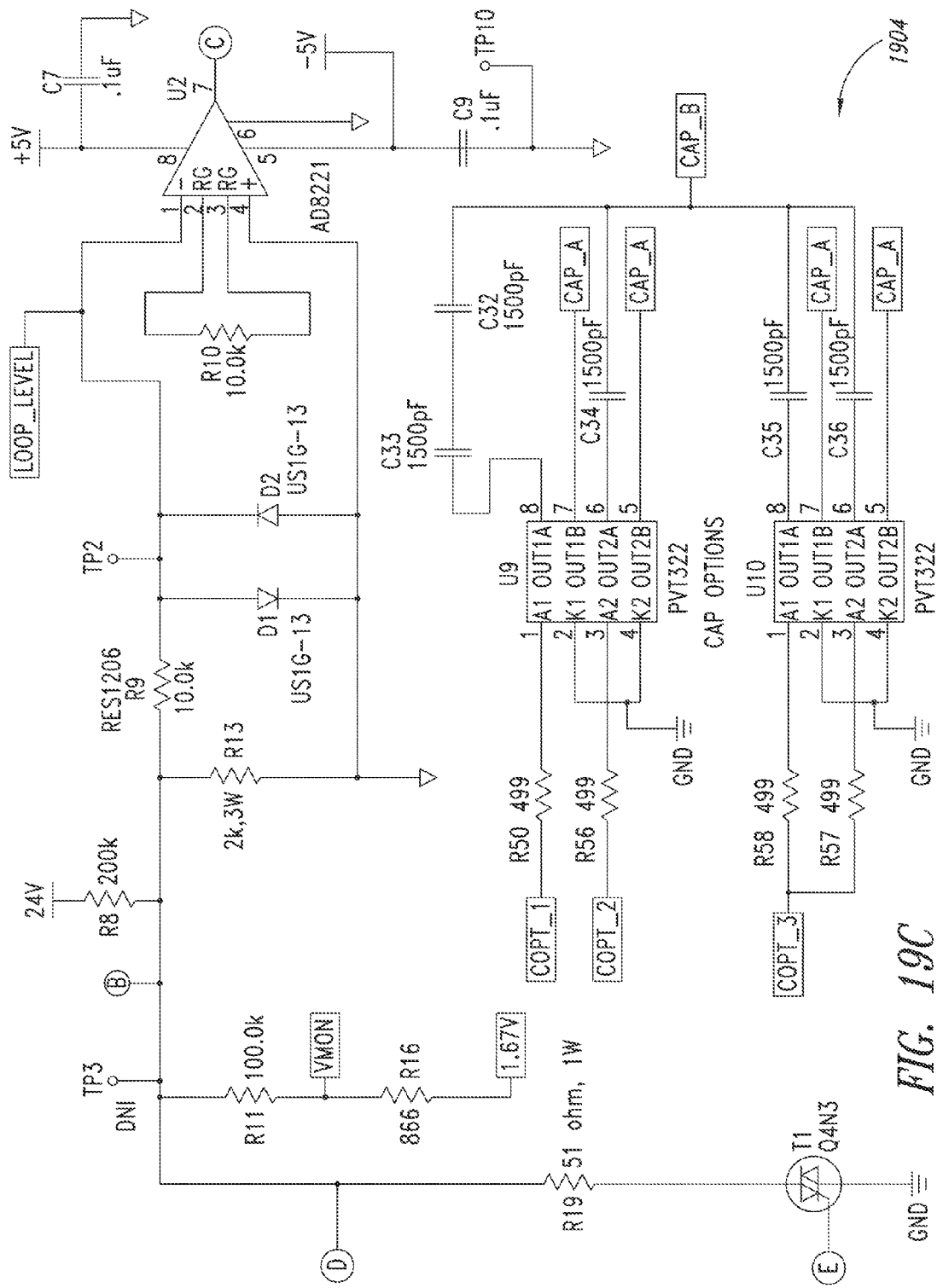
Figure 19D:
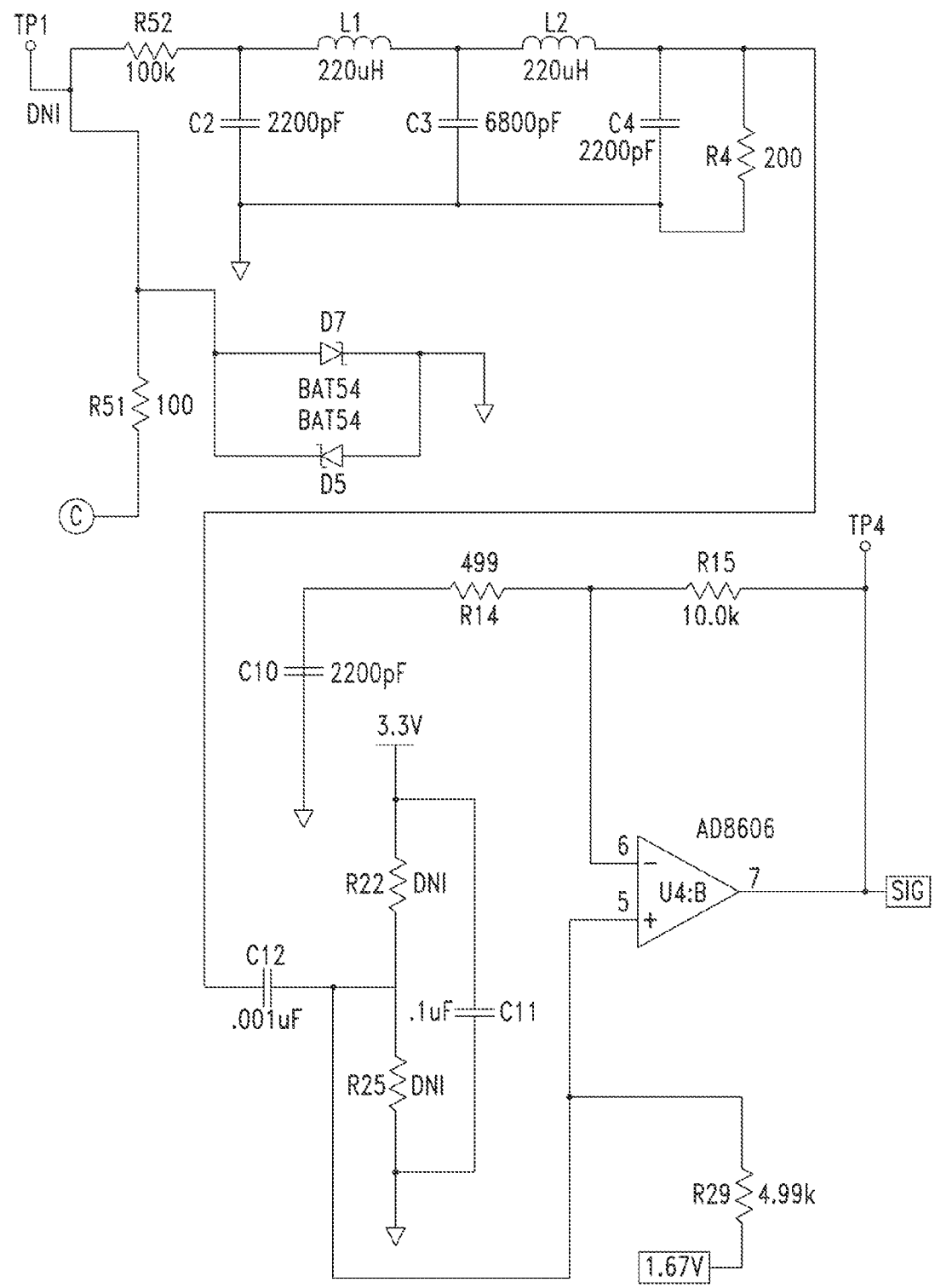
Figure 19E:
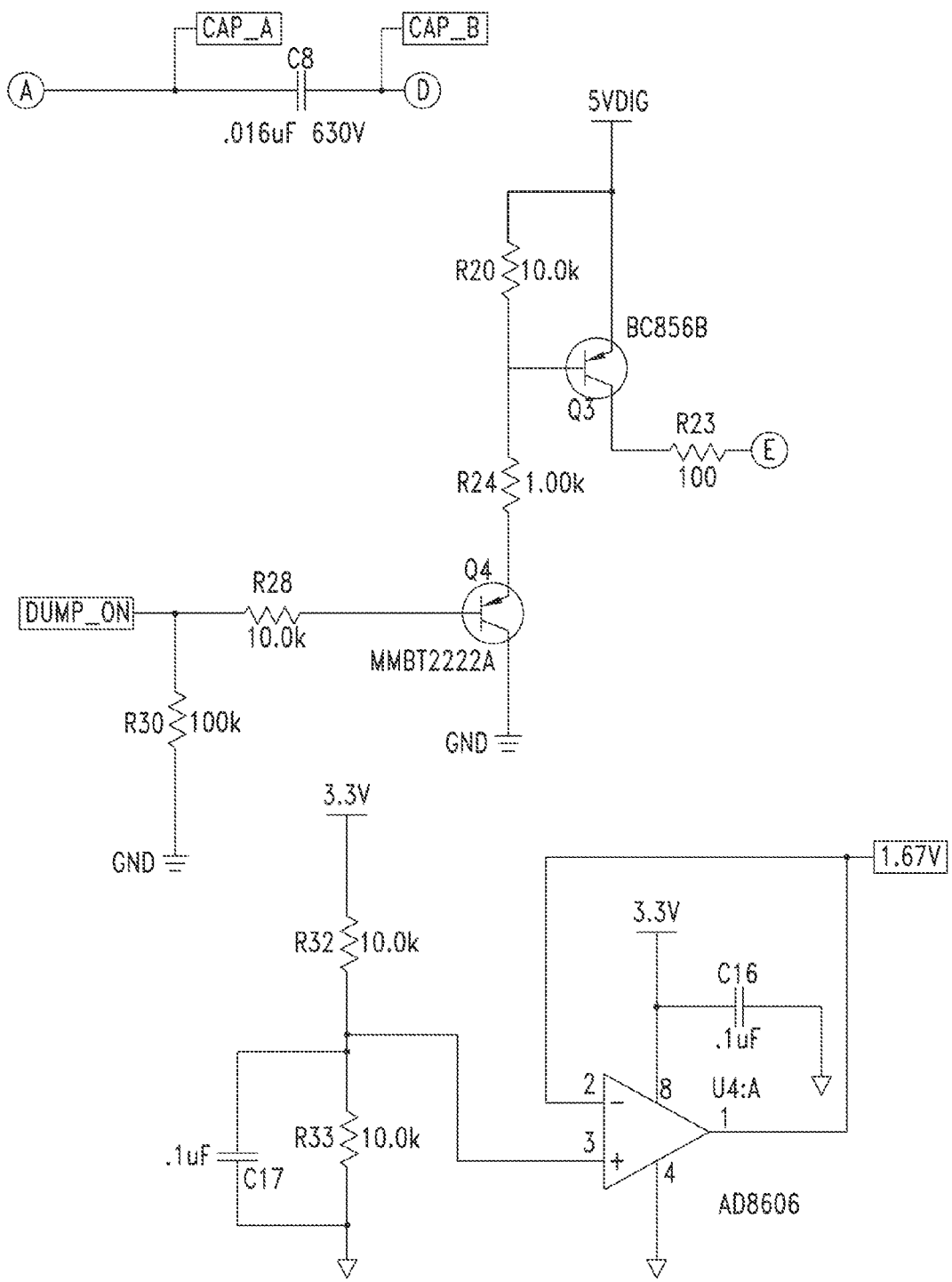
Figure 19F:
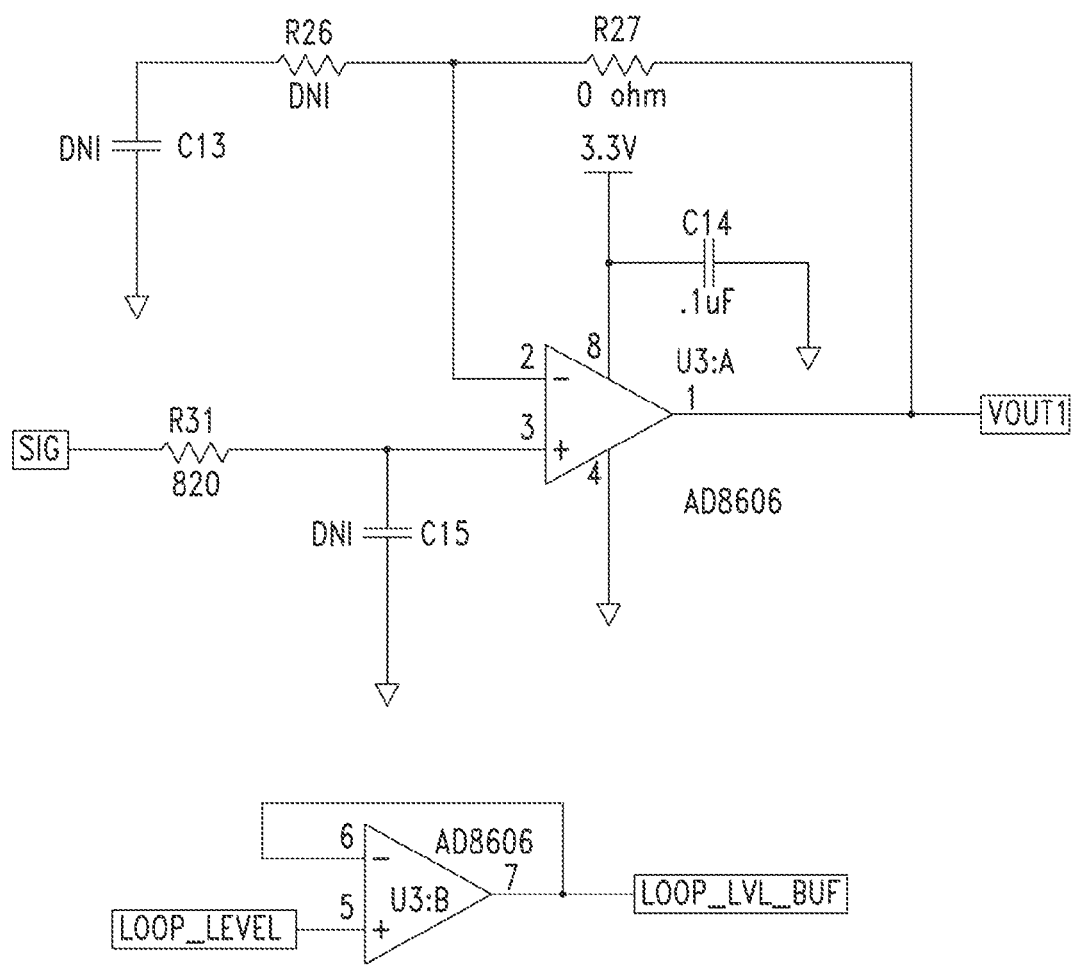
Figure 19G:
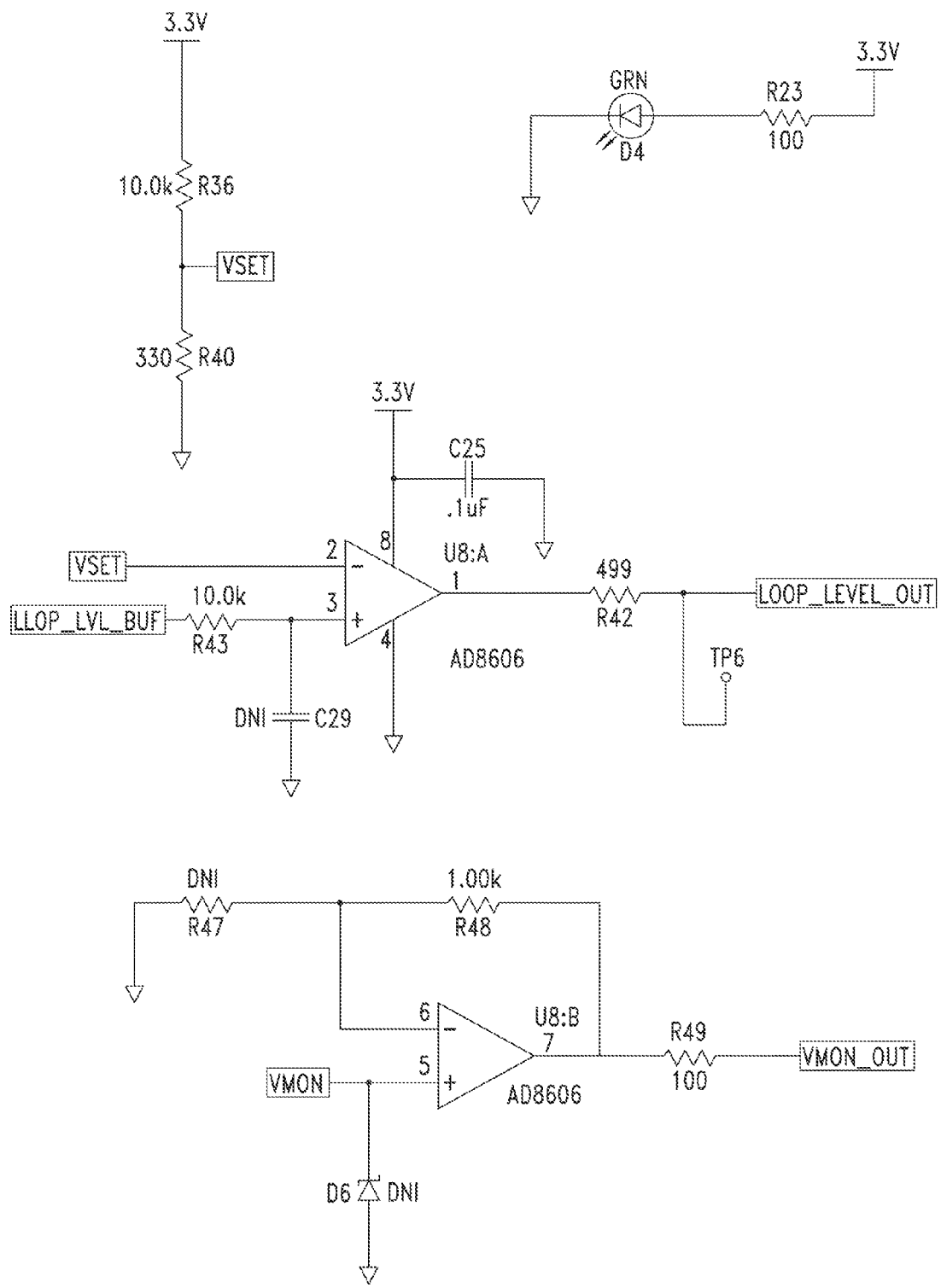
Figure 19H:
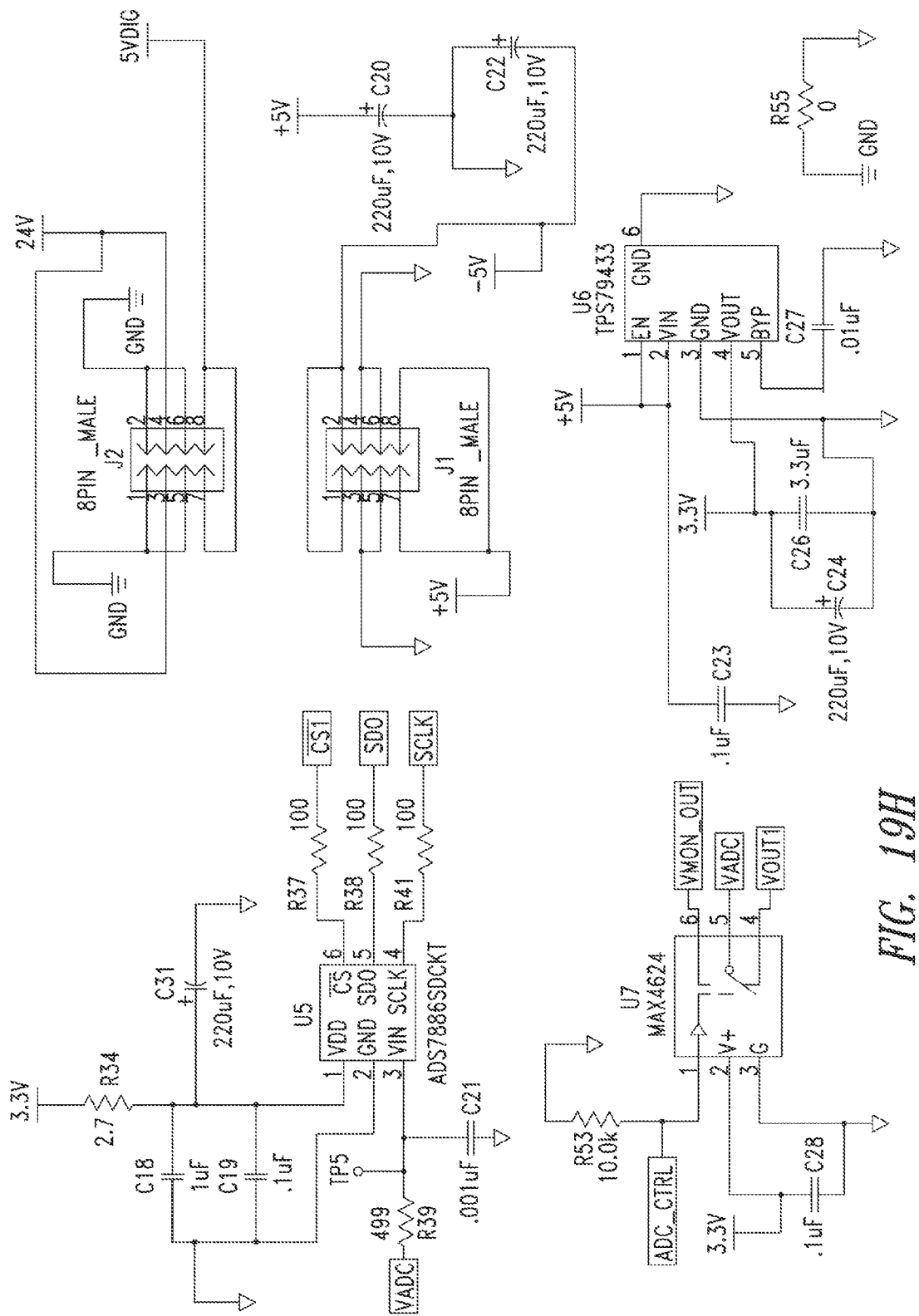
Figure 19I:
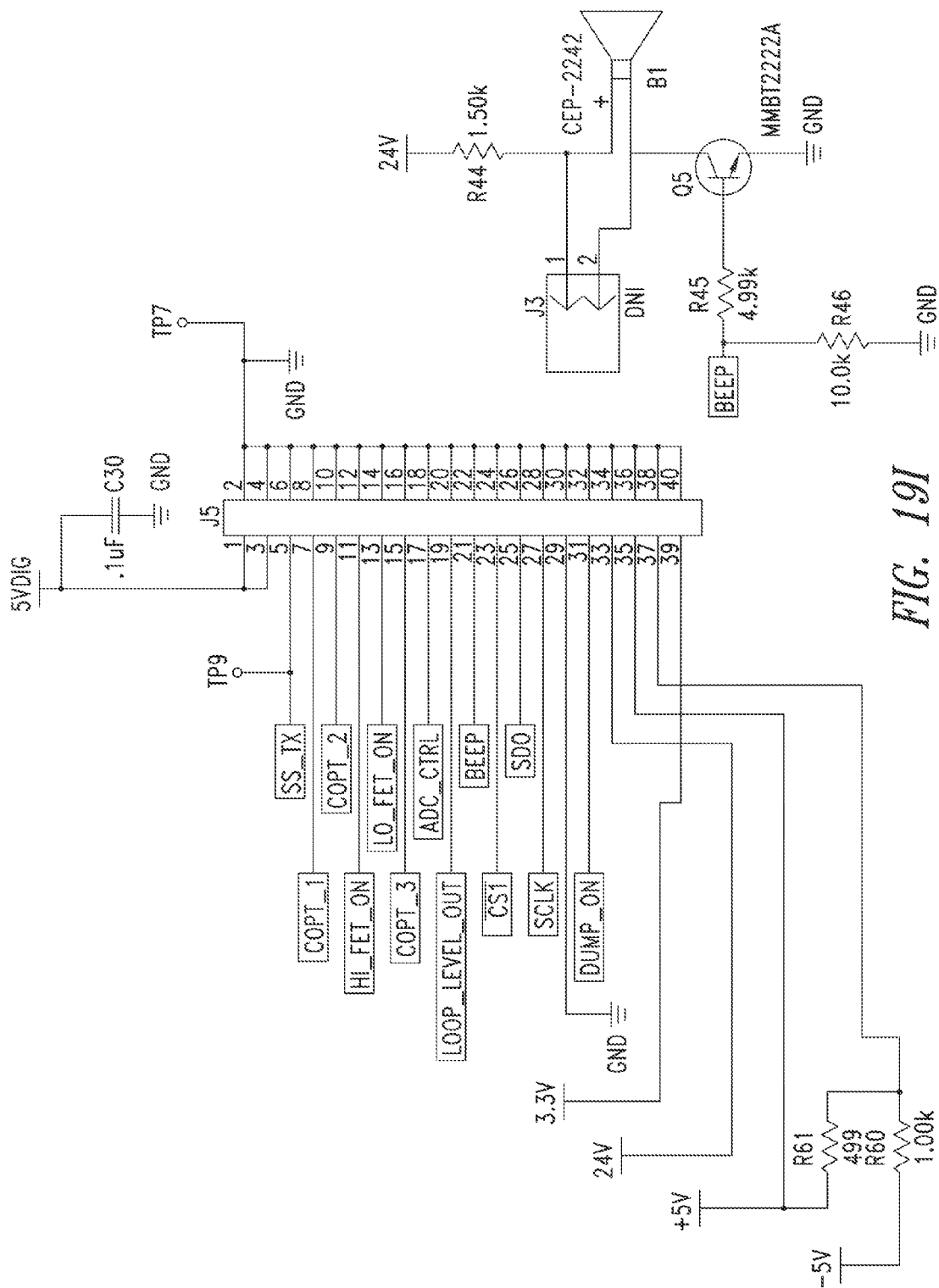

FIG. 18 shows a software configuration 1800 of the interrogation and detection system 14, according to one illustrated embodiment.

The software may include application software 1802 that is responsible for operating the controller 18 (FIGS. 1 and 2). The application software 1802 controls the timing for generating transmit pulses, processes sampled data to detect transponders 24 (FIGS. 1 and 2), and indicates status to the user with the visual indicators 40 (FIGS. 1 and 2) on the display board 1706 (FIG. 17) and/or via the aural indicator 42 on the analog board 1704 (FIG. 17). The application software 1802 is stored in the flash memory 1718 (FIG. 17) and transferred into the RAM 1716 by a boot loader 1804.

The boot loader 1904 is automatically loaded when the FPGA 1708 is configured, and starts execution after a processor core 1806 is reset. The boot loader 1804 is responsible for transferring the application software 1802 from the flash memory 1718 to the external RAM 1716.

The processor platform 1808 is configured into the FPGA 1708 (FIG. 17) on power up from the configuration information stored in the flash memory 1718. The processor platform 1808 implements a custom microprocessor with a processor core 1806, peripherals 1810*a*-1810*n*, and custom logic 1812.

The processor core 1806 may take the form of a soft processor core supplied by XILINX under the name MICROBLAZE™, that implements a 32-bit processor including memory cashes and a floating point unit. A soft core processor is one that is implemented by interconnected FPGA logic cells instead of by a traditional processor logic. The processor core 1806 is connected to the internal FPGA peripherals 1810*a*-1810*n* using a 32-bit processor bus 1811 called the On-Chip Peripheral Bus. The XILINX supplied peripherals for the MICROBLAZE™ processor core 1806 include external memory interfaces, timers, and general purpose I/O.

The custom logic 1812 to create the transmit signals, sample the ADC, and accumulate the transponder return signals is designed as a peripheral to the processor core 1806. The custom logic 1812 is the part of the design of the FPGA 1708.

Some embodiments may substitute a full microprocessor for the soft processor core. Thus, for example, a microprocessor such as the ATOM™ processor, commercially available from Intel Corporation, may be employed in place of the MICROBLAZE™ processor core. The full microprocessor may be communicatively coupled to multiple analog antenna channels via one or more FPGAs and one or more suitable buses. The FPGA may, for example, act as a co-processor and/or cache. Additionally, or alternatively, a higher bandwidth bus architecture may be employed. For example, a PCI Express™ or PCIe™ bus architecture may be employed, rather than an ISA bus architecture. Suitable FPGAs may include those from ATMEL Corporation. Such FPGAs may advantageously have built in PCIe bus architecture, allowing easy integration. This approach may enable more I/O ports, such as USB ports, may provide more or better video options, and may provide faster data rates from the analog antenna channels that otherwise possible using the ISA bus architecture and soft processor core approach.

FIGS. 19A-19I show a control circuit 1900 according to one illustrated embodiment. The control circuit 1900 is used to drive the antenna 16 (FIGS. 1 and 2) to excite or interrogate transponders 24 (FIGS. 1 and 2), and to detect and process signals received by the antenna 16 from the transponders 24. As previously noted, there may be a respective control circuit 1900 for each of the antennas 16, or a single control circuit may be configured to control multiple antennas.

The control circuit 1900 includes a transmitter circuit 1902 formed by a pair of drive transistors (e.g., field effect transistors) Q1, Q2 operated in a push-pull configuration between a high voltage rail (e.g., 24 V) and a low voltage rail (e.g., GND). The drive transistors Q1, Q2 are responsive to respective drive signals DRIVE_HI, DRIVE_LO, which are applied to the gates of the respective drive transistors Q1, Q2. The drive transistors Q1, Q2 are coupled to the antenna 16 by a non-switched capacitor C8 and the coaxial cable 20. The antenna 16 and capacitor C8, as well as capacitance provided by the coaxial cable 20, form an LC circuit.

Optionally, the control circuit 1900 may also include a dynamic tuning circuit 1904. The dynamic tuning circuit 1904 selectively adjusts the capacitance of the LC circuit. In the illustrated embodiment, the dynamic tuning circuit 1904 includes a number of switched capacitors C33-C36 and relays U9, U10. The relays U9, U10 are operated to selectively couple the switched capacitors C33-C36 in series with the non-switched capacitor C8, thereby adjusting the LC characteristics of the LC circuit, and allowing fine tuning of the LC circuit around center frequencies or center channels of a number of wide band frequency bands, as described in more detail below.

Figure 20:
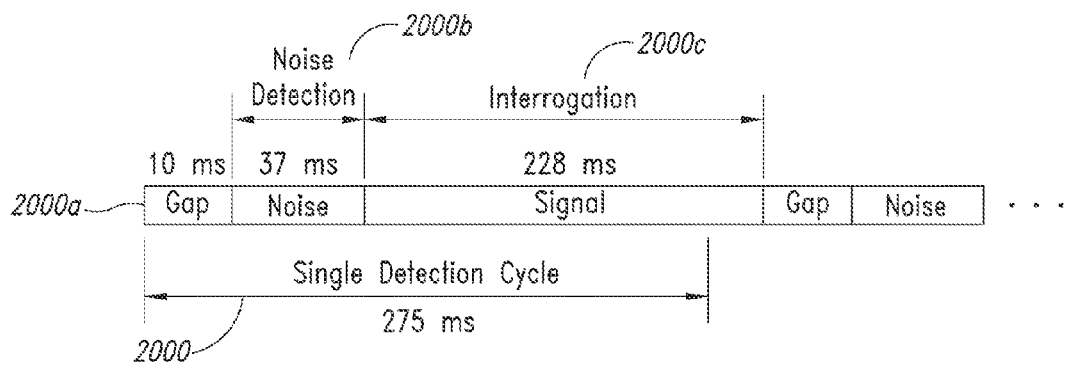
FIG. 20 is a timing diagram illustrating a method of frequency hopping, according to one illustrated embodiment.

FIG. 20 illustrates a detection cycle 2000 that employs an approach that optimizes signal to noise ratio (SNR), according to one illustrated embodiment. Such may, for example, advantageously increase range or increase sensitivity at a given range.

One embodiment is optimized based on having an overall detection cycle that performs well for transponders with resonant frequencies from approximately 136 KHz to approximately 154 KHz, and which has a pulse timing that is consistent with hardware limitations. An optimal SNR may be achieved by, for example, transmitting a single wideband frequency pulse.

The application software 1802 (FIG. 18) implements the detection cycle 2000 using transmission or interrogation in a frequency band centered around a center channel or frequency. In the illustrated embodiment, the application software 1802 sequences through a non-measurement portion (i.e., gap) 2000*a*, and two distinct measurement portions, denominated as a noise detection portion 2000*b* and an interrogation or signal detection portion 2000*c*, each detection cycle 2000. In at least one embodiment, the detection cycle 2000 may, for example, be approximately 275 milliseconds, the gap portion may be approximately 10 milliseconds, the noise portion approximately 37 milliseconds and the interrogation or signal portion approximately 228 milliseconds.

During the noise detection portion 2000*b*, which may, for example be a first measurement portion of each detection cycle 2000, ambient or background noise is measured or sampled, providing a value indicative of a level of ambient or background noise for the particular environment. The noise measurements or samples are taken or captured at a time sufficiently after excitement of the transponders 24 (FIG. 1) by the interrogation signal emitted by the transmitter such that the transponders 24 are substantially not resonating or responding to any previous excitation by interrogation signals. In particular, a number N of measurements or samples are taken during the noise detection or first measurement portion 2000*b*.

During the interrogation portion 2000*c*, which may, for example take the form of the second measurement portion of each detection cycle 2000, responses by transponders 24 are measured or sampled. The response measurements or samples are taken with the transmitter transmitting or at a time sufficiently close to excitement of the transponders 24 by the interrogation signal emitted by the transmitter such that the transponders 24 are still substantially resonating or responding to the interrogation signal. In particular, a number M of measurements or samples are taken during the interrogation or second measurement portion 2000*c*.

While the interrogation portion 2000*c* is illustrated as one contiguous or continuous portion 2000*c*, in some embodiments the interrogation portion 2000*c* may take the form of two or more separate portions or intervals. Each of the portions 2000*c* may employ the same transmit frequency band, for example centered around 145 KHz. Other center channels or frequencies may for example be 136 KHz, 139 KHz, 142 KHz, 145 KHz, 148 KHz, 151 KHZ and/or 154 KHz, or any other frequency suitable for exciting the transponder to resonate. Some embodiments may employ frequency hopping, for example transmitting a different center channel or frequency for each of a plurality of interrogation portions 2000*c* of each detection cycle 2000. Such is discussed further in U.S. provisional patent application Ser. No. 60/892,208, filed Feb. 28, 2007 and U.S. non-provisional application Ser. No. 11/743,104, filed May 1, 2007.

The gap portion 2000*a* may provide time for the response of the transponders 24 to the interrogation signal to decay sufficiently to allow measurement of noise.

Some embodiments may arrange the gap 2000*a*, the noise detection portion 2000*b* and/or the interrogation portion 2000*c*, or parts thereof, in a different order.

In one embodiment, the time to accumulate the noise sample or value indicative of a noise level may, for example, be approximately 37 milliseconds, and the time to accumulate the transponder signal measurement approximately 228 milliseconds. Along with a gap 2000*a* of approximately 10 milliseconds between the signal and noise portions, the time for a single detection cycle 2000 would be approximately 275 milliseconds. As noted above, the transmitter is OFF during the noise measurement portion 2010*b* of each detection cycle to measure ambient noise, and the signal measurement portion 2010*c* is taken with the transmitter transmitting a wideband interrogation signal about the particular center channel or frequency.

The noise samples may be accumulated and a highest one or more of multiple samples or measurements over one or more detection cycles selected or used to prevent unwarranted fluctuations. The response signals from the transponder 26 may be accumulated and/or averaged or integrated over one detection cycle or over multiple detection cycles.

The number N of noise measurements or samples and/or the number M of response measurements or samples may be selected to achieve a desired ratio of N to M, in order to achieve or maintain a desired signal to noise ratio. For example, obtaining 200 noise measurements or samples and 800 response measurements or samples each detection cycle results in an SNR of approximately 2 (e.g., the square root of the 800 divided by 200). While an SNR as low as 1.1:1 may be sufficient in some embodiments, an SNR approaching 2:1 ensures sufficient differentiation to eliminate or reduce the possibility of false positives to an acceptable level for the particular applications envisioned herein. Any known hardware and software accumulators, summer, integrators and/or other hardware or software may be suitable.

Figure 21A:
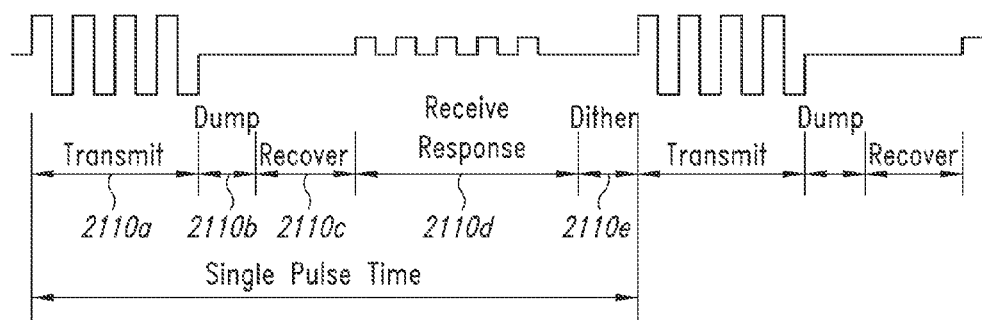
FIG. 21A is a timing diagram illustrating pulsed timing, according to one illustrated embodiment.

FIG. 21A illustrates pulse timing, according to one illustrated embodiment.

The custom logic in the FPGA 1708 (FIG. 17) generates the timing and control signals for each pulse 2110. During a transmit portion 2110*a* of the pulse 2110, the logic of the FPGA 1708 drives the drive transistor control lines to generate the transmit signal. The FPGA logic controls the frequency of the transmit signal. During a dump portion 2110*b* of the pulse 2110, the logic of the FPGA 1708 drives the gate of the dump TRIAC T1 to quickly drain the transmit energy from the antenna 21 in order to allow detection of the response signal form the transponder 24, if any. A recovery portion 2110*c* of the pulse 2110 allows receiver filters and amplifiers to recover from the transmitted pulse before detecting the response signal from the transponder 24, if any. During the receive response portion 2110*d* of the pulse 2110, the FPGA 1708 controls the signal ADC 1728 to sample the response signal from the transponder 24, if any. The signal ADC 1728 may, for example, sample at a 1 MHz sample rate with a 12-bit resolution. A dither portion 2110*e* of the pulse 2110 has a random variable length of time, and may, for example be generated by a pseudo-noise (PN) sequence generator. Adding a random length of time between pulses de-correlates the response signal received from the transponder 24 from constant frequency sources of interference, if any.

For example, within each of 228 millisecond signal measurement intervals 400*c* discussed above, the custom logic of the FPGA 1708 (FIG. 17) accumulates the received signals from, for example 800 pulses.

Figure 21B:
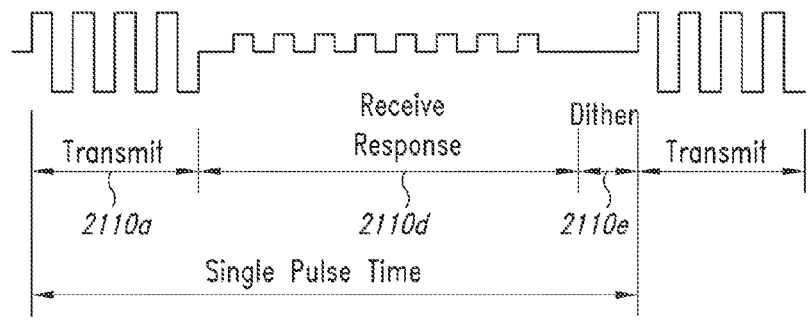
FIG. 21B is a timing diagram illustrating pulsed timing, according to another illustrated embodiment.

FIG. 21B illustrates pulse timing, according to one illustrated embodiment. The pulse timing is similar in some respects to that illustrated in FIG. 21A, hence similar or identical structures, acts or features are identified using the same reference numbers. Only significant differences between the two are discussed below.

In contrast to the embodiment of FIG. 21A, the embodiment of FIG. 21B may advantageously eliminate the dump portion 2110b of the pulse 2110. Such may be omitted, for example, where the antenna 21 that transmitted the most recent interrogation signal is not being used to monitor for a response to the interrogation signal. Such may advantageously allow monitoring for the response to occur sooner than would otherwise be possible if the dump portion 2110b were needed.

Also in contrast to the embodiment of FIG. 21A, the embodiment of FIG. 21B may advantageously eliminate the recovery portion 2110c of the pulse 2110. Such may be omitted, for example, where the antenna 16 that transmitted the most recent interrogation signal is not being used to monitor for a response to the interrogation signal. Such may advantageously allow monitoring for the response to occur sooner than would otherwise be possible if the recovery portion 2110c were needed.

Removal of the dump portion 2110b and/or recovery portion 2110c may allow for a more favorable sampling rate or better resolution or may allow a longer noise detection portion, which may significantly enhance performance.

Figure 22:
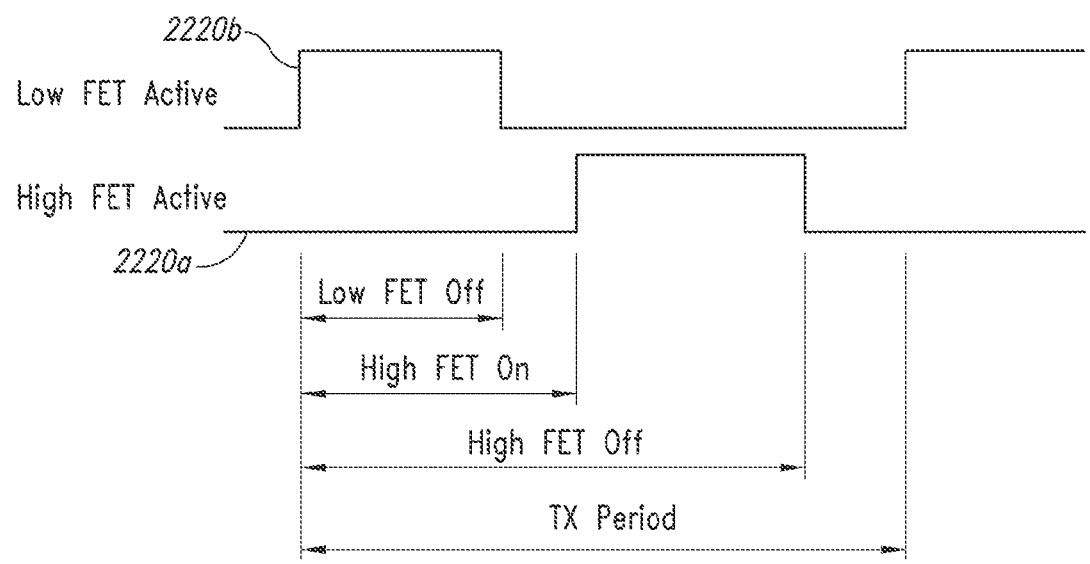
FIG. 22 is a timing diagram showing activation of a pair of transistors of the control circuit in a push-pull configuration to drive the antenna, according to one illustrated embodiment.

FIG. 22 shows signal timing for driving the drive transistors Q1, Q2 (FIG. 19A), according to one illustrated embodiment.

The custom logic in the FPGA 1708 (FIG. 17) generates the signals 2220a, 2220b to drive the drive transistors Q1, Q2 (FIG. 19A) during the transmit portion 2110a (FIG. 21) of the pulse 2110. A transmit (TX) period value is used by the logic of the FPGA 1708 to set the transmit frequency. The low transistor (e.g., Low FET) Q2 turns ON at the beginning of the transmit period. The Low FET off value controls when the low transistor (e.g., Low FET) Q2 is turned OFF. The low transistor Q2 is turned OFF before the high transistor (e.g., High FET) Q1 is turned ON to avoid a short circuit through the transistors Q1, Q2. The High FET on value controls when the high transistor (e.g., High FET) Q1 is turned ON. The High FET Off value controls when the high transistor Q1 is turned OFF. The high transistor is turned OFF before the low transistor Q2 is turned ON to avoid a short circuit through the transistors Q1, Q2. For example, to achieve a transmit frequency of 144.9 KHz, the transmit period should be set to 6.9 µsec. Also for example, a suitable duration that both the low and high transistors Q1, Q2 are OFF may be set to 400 nsec.

The ADC converts the signal received from the transponder 24, if any, from analog to digital. Such conversion may, for example, be performed at a sampling rate of 1 MHz with a 12-bit data resolution. The sampled ADC data is then accumulated together or integrated, for example over 800 measurements or samples, to compute the total summed response signal received from the transponder 24, if any.

The accumulated or integrated received signal may be match filtered with both in-phase and quadrature reference signals to determine the signal magnitude. The received receive signal is matched filtered with a plurality of reference signals, for example with the seven reference signals, for instance as shown in Table 1 below. Some embodiments, may employ match filtering before accumulating or integrating the received signal.

TABLE 1

| Match Frequency |
| --- |
| 136 KHz |
| 139 KHz |
| 142 KHz |
| 145 KHz |
| 148 KHz |
| 151 KHz |
| 154 KHz |

The maximum value for the matched filters (e.g., seven matched filters) with active transmit is compared with an adjusted detection threshold. If the maximum value is greater than the detection threshold, then a response signal from a transponder 26 is considered as having been detected, and appropriate action is taken.

Noise faults may be detected as well as antenna transmit voltage faults. Noise faults may be detected when the matched filter output during the noise detection portion is greater than a noise fault threshold (e.g., a threshold magnitude 2.7 mV over a threshold time, e.g., 7 seconds or threshold magnitude 7 mV over a time threshold of 7 seconds). Antenna transmit voltage faults may be detected when the antenna transmit voltage drops below an antenna voltage fault threshold (e.g., 270 $V_{Peak-to-Peak}$). Two environmental faults in a row such as the above, may trigger an Environmental Error Mode, while two normal measurements in a row may return to a normal Scan Mode. Faults in general are discussed in more detail below. Alternatively, the interrogation and detection system may employ a fast Fourier transform approach in lieu of match filtering.

Figures 23A, 23B, 23C:
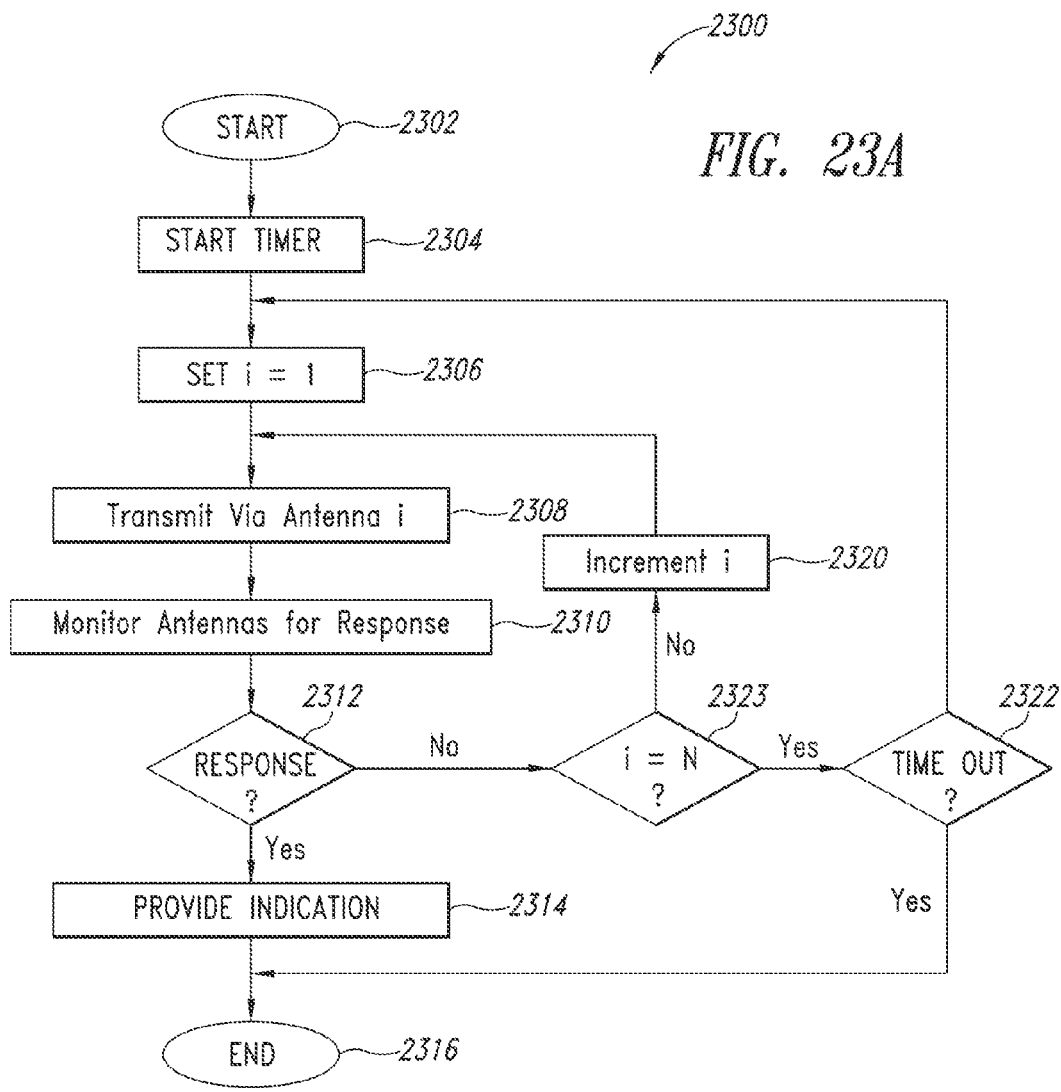
FIG. 23A is a flow diagram of a method of operating an interrogation and detection system, according to one illustrated embodiment.
FIG. 23B is a flow diagram of a method of monitoring all antennas for a response to an interrogation signal, according to one illustrated embodiment.
FIG. 23C is a flow diagram of a method of monitoring all antennas except a transmitting antenna for a response to an interrogation signal, according to one illustrated embodiment.

FIG. 23A shows a method 2300 of operating the interrogation and detection system 14, according to one illustrated embodiment.

The method 2300 starts at 2302. For example, the method 2300 may start on application of power to the interrogation and detection system 12 or in response to activation of a switch by a user such as a clinician, surgeon In response to detecting an application of power, the interrogation and detection system 14 may enter a Power-Up mode. The Power UP mode 502 may, for example, in response to the application of power to the controller 18 and turning ON the switch on the controller 18. In the Power-Up mode, a Power indicator (e.g., LED) may be turned ON or illuminated, and may remain ON or illuminated as long as the power is applied and the switch is in the ON state. In response to entering the Power UP mode, the software 1800 may perform software initialization, built in tests, and an audio/visual test. If a fault is detected, the software 1800 may progress to a System Fault Mode. If no faults are detected, the software 1800 may turn a System Ready indicator (e.g., LED green), and enter an antenna Detection Mode. In the System Fault mode, the software 1800 may cause an indication of the detection of a system fault by blinking a System Ready indicator (e.g., LED) yellow, and/or issuing a sequence of rapid beeps or other sounds. The corrective action for the System Fault Mode may be to cycle power to reinitiate the Power Up mode. Continued failure indicates a failed controller 18.

In the Antenna Detection Mode, the software 1800 checks for antennas 16 connected to the controller 18. The Antenna Detection Mode may be indicated by turning the System Ready indicator (e.g., LED) green and turning the Antenna Ready indicator (e.g., LED) OFF. If no antenna 16 is detected, the software 1800 remains in the Antenna Detection Mode. If one or more antennas 16 are detected, the software 1800 makes note of the total number of antennas and progresses to the Antenna Initialization Mode.

At the start of the Antenna Initialization Mode, after the detection of the antennas 16, the software 1800 may turn the Antenna Ready indicator (e.g., LED) yellow and optionally check for the presence of a respective fuse coupled to antennas 16. If a fuse is found, the software 1800 may attempt to blow the fuse and verify that the fuse was correctly blown. After the fuse is blown the software 1800 may verify that respective antenna 16 is operating within tolerances. The software 1800 may indicate that the antenna 16 is ready by turning the Antenna Ready indicator green. The software 1800 may also start a timer which will allow the antenna 16 to be disconnected and reconnected to the controller for a period to time (e.g., 5 hours) after the fuse is blown. The controller 18 may determine the adjustments or fine tuning to be made about the center frequencies or channels during Antenna Initialization Mode. In particular, the controller 18 may determine the particular frequency in each of the frequency bands that elicits the response with the highest voltage. The controller 18 may determine such be varying the capacitance of the LC circuit using the switched capacitors C33-C36 during the Antenna Initialization Mode. The particular combination of switched capacitors C33-C36 which achieved the response with the highest voltage may then be automatically employed during the Scan Mode (discussed below) to adjust or fine tune about the center frequency or channel in each broad band of transmission. Other approaches to determining the fine tuning may be employed.

If the software 1800 does not successfully complete the Antenna Initialization Mode, the software 1800 enters an Invalid Antenna Mode. If the software 1800 successfully completes the Antenna Initialization Mode, the software 1800 progresses to the Scan Mode to automatically start scanning. In the Invalid Antenna Mode, the software 1800 may blink the Antenna Ready indicator yellow and issues a slow beep pattern. The Invalid Antenna Mode may be entered in response to any of the following conditions: 1) the antenna 16 connected to the controller 18 is out of tolerance; 2) the controller 18 is unable to blow the fuse of the antenna 16; 3) the antenna 16 does not have a fuse and more than the set time period has past (e.g., 5 hours) since a fuse was blown; 4) the antenna 16 does not have a fuse and the controller 18 has been restarted; 5) the antenna 16 has been connected to the controller 18 for more than the set time period (e.g., 5 hours); 6) the antenna 16 is detuned due to close proximity to metal. The corrective action for the Invalid Antenna Mode is to remove the invalid antenna 16 and attach a new antenna 16 to the controller 18 that contains a fuse or to reconnect the antenna 16 while holding it in the air at least 2 feet away from large metallic objects. The software 1800 enters the Scan Mode when the antennas 16 are ready and the operator presses a Start/Stop button. The software 1800 may issue a short three beep pattern via the speaker or beeper when entering the Scan Mode to identify the entry to the user.

In the Scan Mode, the software 1800 may continuously or periodically perform the following functions: 1) look for response signals from transponders 24; 2) monitor the noise level; 3) insure the antennas 16 are connected and operating correctly; and 4) blink the appropriate indicator in a circular pattern. The interrogation and monitoring for response may be performed using a detection cycle, such as that set out in FIGS. 21A, 21B and the description related to those Figures. While, not specifically set out in FIG. 18, such may also include optimization of signal to noise ratio, such as set out in FIG. 20 and the description related thereto.

At 2304, a timer starts. The timer allows a limit to be set on the amount of time spent scanning for a transponder 24 (i.e., scan maximum time interval). Alternatively, a counter could be employed to set a limit of the number of iterations that the antennas 16 are successively employed to transmit interrogation signals.

At 2306, an antenna counter i is set, for example set to 1. The antenna counter allows the method 2300 to successively iterate through each of a number N of antennas 16 to transmit the interrogation signal. The number N of antennas 16 may have been determined during the Antenna Detection Mode.

At 2308, an interrogation signal is transmitted from an $i^{th}$ antenna 16. In particular, the FPGA 1708 (FIG. 17) may cause one of the plug-in boards to cause the antenna 16 coupled thereto to transmit an interrogation signal. The interrogation signal may advantageously take the form of an unmodulated interrogation signal, for example in the radio or microwave portions of the electromagnetic spectrum.

At 2310, one or more antennas 16 are monitored for a response to the interrogation signal. In particular, a number of the plug-in boards may monitor the respective antenna 16 coupled thereto for the response to the interrogation signal. For example, all of the antennas 16 may be monitored to a response to the interrogation signal. Alternatively, all except the antenna 16 that transmitted the most recent interrogation signal (i.e., $i^{th}$ antenna) may be monitored for a response to the interrogation signal. As another alternative, some subset of all of the antennas 16 may be monitored for a response to the interrogation signal. The response may advantageously take the form of an unmodulated response signal, for example in the radio or microwave portions of the electromagnetic spectrum.

At 2312, it is determined if a response to the interrogation signal was received. For example, the FPGA 1708 (FIG. 17) may poll or otherwise monitor each of a number of plug-in or analog boards to determine if a response signal was detected via any of the antennas coupled to those plug-in or analog boards. If a response to the interrogation signal was received, a suitable indication is provided at 2314, and the method 2300 terminates at 2316. For example, when an appropriate response signal from a transponder 24 is detected while in Scan Mode, the software 1800 may turn ON an amber DETECT indicator (e.g., LEDs) and/or provide an audible alarm. The alarm may, for example, beep a continuous solid tone as long as the transponder is detected, with a minimum of beep duration of, for instance 0.5 second. If a response to the interrogation signal was not received, it is determined whether there are additional antennas to transmit the interrogation signal from at 2318.

If there are additional antennas to transmit from, the counter is incremented at 2320 and control returns to 2308 to transmit via the next $i+1^{th}$ antenna 16. This can allow iteration through a number of antennas 16 as the antenna that transmits the interrogation signal. As previously explained, antennas 16 may be operated to transmit an interrogation signal in an order of appearance along a longitudinal axis of the patient support surface or may be operated in any other order. Also as previously noted, all or some lesser number of antennas may be employed to transmit the interrogation signal in any single pass or iteration through the set or subset of antennas 16.

If there are not further antennas to transmit the interrogation signal from, it is determined if a time limit (i.e., scan maximum time interval) has been exceeded at 2322. If the time limit has been exceeded the method 2300 terminates at 2316. If the time limit has not been exceeded, the counter is reset at 2306. This allows multiple passes through the use of each antenna in a set or subset of antennas 16 as the interrogating antenna 16. When the operator or user pushes the Start/Stop button or the a scan maximum time interval (e.g., 4 minute) has been reached, the software 1800 may issue a short three beep pattern and return to the Antenna Ready Mode.

If the software 1800 detects that one of the antennas 16 is disconnected while in the Scan Mode, the software 1800 enters the Scan Fault Mode. In the Scan Fault Mode, the software 1800 may issue a sequence of rapid beeps and blink ON and OFF the amber DETECT indicator. The Scan Fault Mode can be cleared by pushing the Start/Stop button. The software 1800 will automatically clear the scan fault mode after 10 beeps.

While in the Scan Mode, if excess noise or loss of transmit signal is detected, the software 1800 may progress to the Environment Error Mode. In the Environment Error Mode, the software 1800 may issue or produce an appropriate indication. For example, the software 1800 may cause the production of a sequence of slow beeps and the blinking ON and OFF the green circle indicator. The corrective action for the Environment Error Mode is to reposition the antenna with respect to any large metal objects or sources of electrical interference. The software 1800 may automatically stop the scan if the environment error condition lasts for more than a set time or number of beeps (e.g., 5 beeps).

FIG. 23B shows a method 2310*b* of monitoring all antennas for a response to an interrogation signal, according to one illustrated embodiment.

At 2318, an interrogation and detection system monitors all antennas 16 for a response to the interrogation signal.

FIG. 23C shows a method 2310*c* of monitoring all antennas except a transmitting antenna for a response to an interrogation signal, according to one illustrated embodiment.

At 2320, an interrogation and detection system monitors all antennas 16 for a response to the interrogation signal, except the antenna 16 the transmitted the most recent interrogation signal.

Figure 24A:
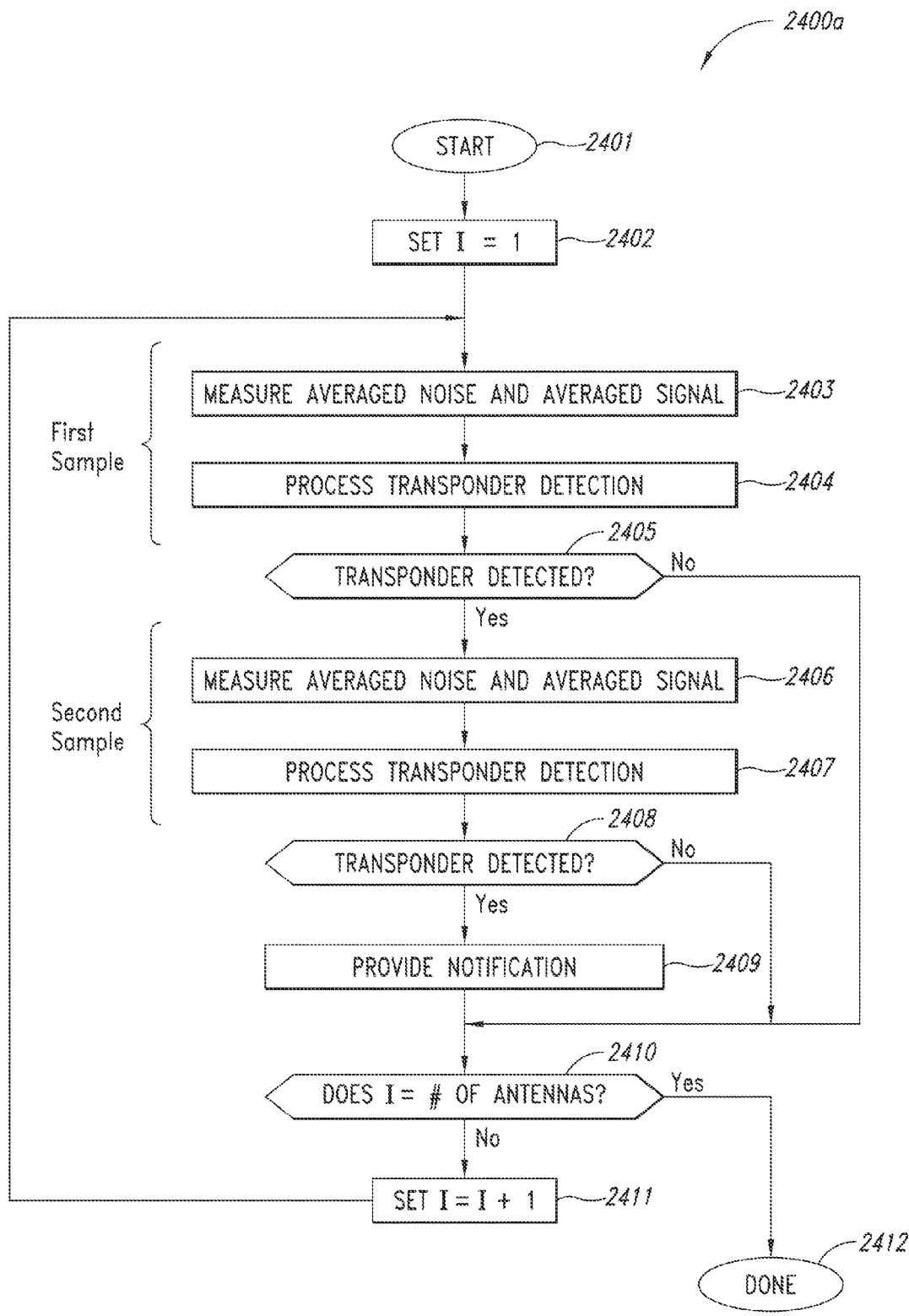
FIG. 24A is a high level flow diagram of a method of operating an interrogation and detection system to detect transponders, according to one illustrated embodiment.

FIG. 24A shows a method of operating an interrogation and detection system to detect transponders 2400*a*, according to one illustrated embodiment.

The method 2400*a* starts at 2401. For example, the method 2400*a* may start when the interrogation of detection system is turned ON, or when power is supplied, or in response to a call from a procedure or function.

At 2402, an antenna counter I is set, allowing the method 2400*a* to iterate through one or more antennas (n) of the interrogation and detection system. The interrogation and detection system iterates through the antennas by transmitting interrogations signals successively from each of a number of the antennas, typically one antenna at a time, and monitoring or listening for response signals on one or more of the antennas.

At 2403, the interrogation and detection system measures averaged noise and averaged signals. At 2404, the interrogation and detection system processes the averaged noise and averaged signal, and at 2405 determines whether a transponder (i.e., return or response signal from transponder) has been detected.

In the embodiment illustrated in FIG. 24A, the interrogation and detection system requires more than one (e.g., two) successive detections of the transponder to conclude that the signal detected indicates the presence of a transponder. Such prevents against false positive determinations. Hence, at 2406, the interrogation and detection system again measures averaged noise and averaged signals. At 2407, the interrogation and detection system again processes the averaged noise and averaged signal and at 2408 determines whether a transponder (i.e., return or response signal from transponder) has been detected.

If a transponder has been detected an adequate number of times (e.g., twice), the interrogation and detection system provides notification at 2409. Notification may, for example, include sending an electrical or optical signal and/or producing a visual, aural or tactile alert to a user (e.g., medical service provider). If the interrogation and detection system determines that a transponder has not be detected at either 2405, 2407, control passes to 2410.

At 2410, the interrogation and detection system determines whether there are further antennas to iterate through. If so, the antenna counter is iterated, and control returns to 2403. If not, the method 2400*a*, may terminate at 2412. Alternatively, the method 2400*a* may return to 2402 and continuously repeat as long as power is supplied to the interrogation and detection system.

Figure 24B:
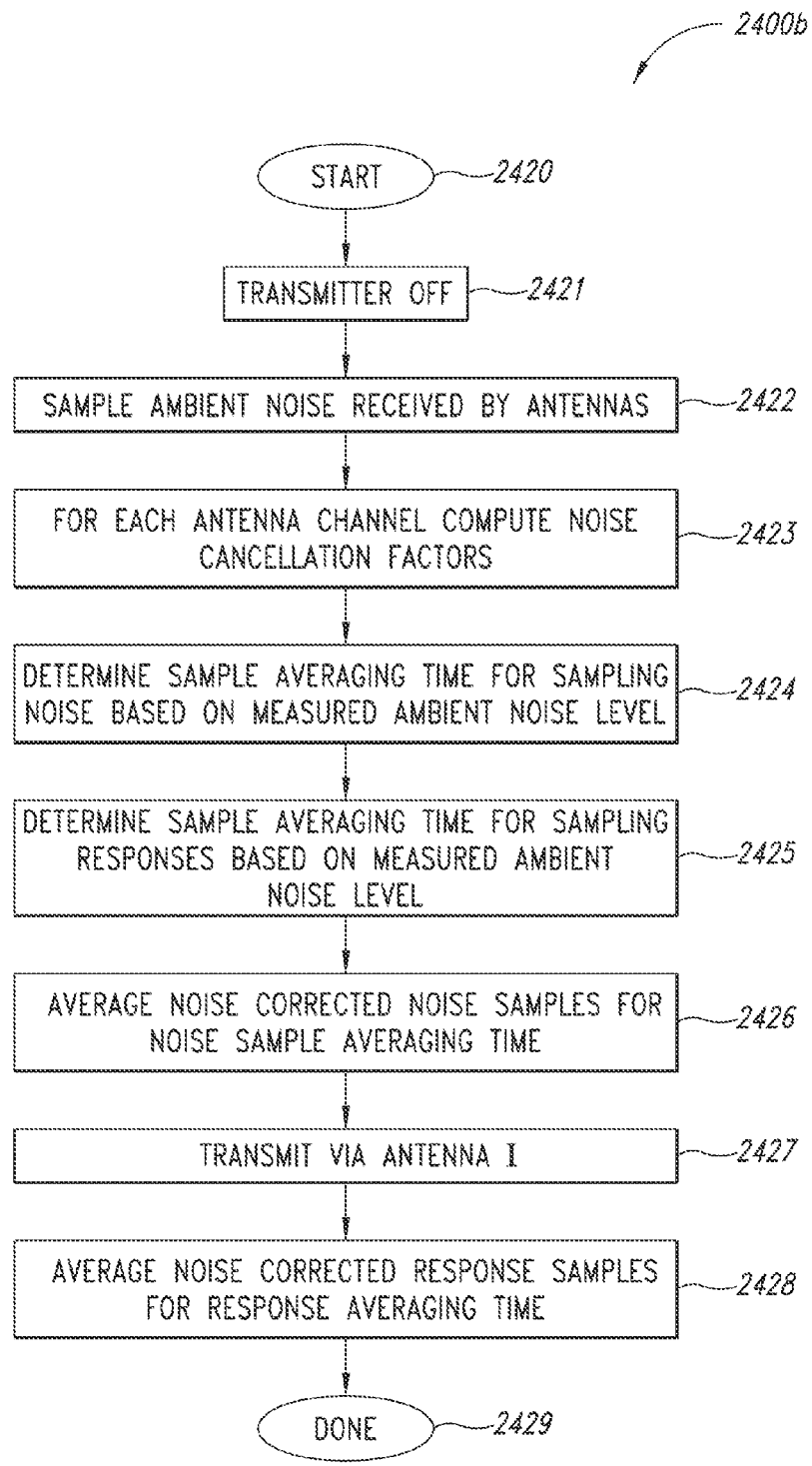
FIG. 24B is a low level flow diagram of a method of operating an interrogation and detection system to sample noise and responses and to adjust sampling times and perform noise correction, according to one illustrated embodiment, the method useful with the method of FIG. 24A.

FIG. 24B shows a method of operating an interrogation and detection system to sample noise and responses and to adjust sampling times and perform noise correction 2400*b*, according to one illustrated embodiment, the method useful with the method of FIG. 24A.

The method 2400*b* starts at 2420. For example, the method 2400*b* may start in response to a call from a procedure that implements the method 2400*a*. The method 2400*b* may, for example, be employed in measuring averaged noise and averaged signal 2403 (FIG. 24A).

At 2421 a transmitter of the interrogation and detection system is OFF (i.e., not transmitting interrogation signals) or is turned OFF if not already OFF. This starts a noise detection portion of a transponder detection cycle. At 2422 ambient noise received by the antennas is sampled. For example, ambient noise detected by all of the antennas may be sampled by the interrogation and detection system.

At 2423, the interrogation and detection system determines noise cancellation factors for each antenna. The interrogation and detection system may employ a variety of approaches for determining the noise cancellation factors, for example computing a noise cancellation factor for each antenna based on ambient noise detected on all of the other antennas except the antenna for which the respective noise cancellation factor is being computed.

At 2424, the interrogation and detection system determines a sample averaging time for sampling nose based on the measured ambient noise level. At 2425, the interrogation and detection system determines a sample response averaging time based on the measured ambient noise level. The sample averaging times determine how long samples of noise or response will be averaged in determining noise or response measurements or levels. Such dynamic determination of sample averaging times allows the interrogation and detection system to accommodate a changing noise environment. For example when a piece of equipment is introduced or removed from the environment or a piece of equipment turns ON or OFF, or otherwise changes amount or frequency distribution of noise it generates in the environment. Thus, the interrogation and detection system may obtain adjust the noise floor to increase range in real time or almost real time in response to the actual noise in the environment.

At 2426, the interrogation and detection system averages noise corrected noise samples for the noise sample averaging time. As noted above, the noise sample averaging time may be determined dynamically. The noise samples may be corrected, for example, using the determined nose cancellation factors.

At 2427, the interrogation and detection system transmits interrogation signal(s) from one of the antennas. As previously noted, the interrogation and detection system my iterate through the antennas one at a time, for example using an antenna counter I. At 2428, the interrogation and detection system averages noise corrected responses for the response averaging time. As noted above, the response sample averaging time may be determined dynamically. The response samples may be corrected, for example, using the determined nose cancellation factors. It is noted that as received, the response signals typically contain a mix of signal and noise, hence is generally referred to herein as responses. After noise correction, the result is theoretically pure signal. In practice there may be some still be some amount of noise remaining, however the signal will typically dominate the noise after noise correction.

The method 2400b may terminate at 2429, for example until called again by the procedure that implements 2400a (FIG. 24A) to transmit interrogation signals from a next antenna.

Figure 24C:
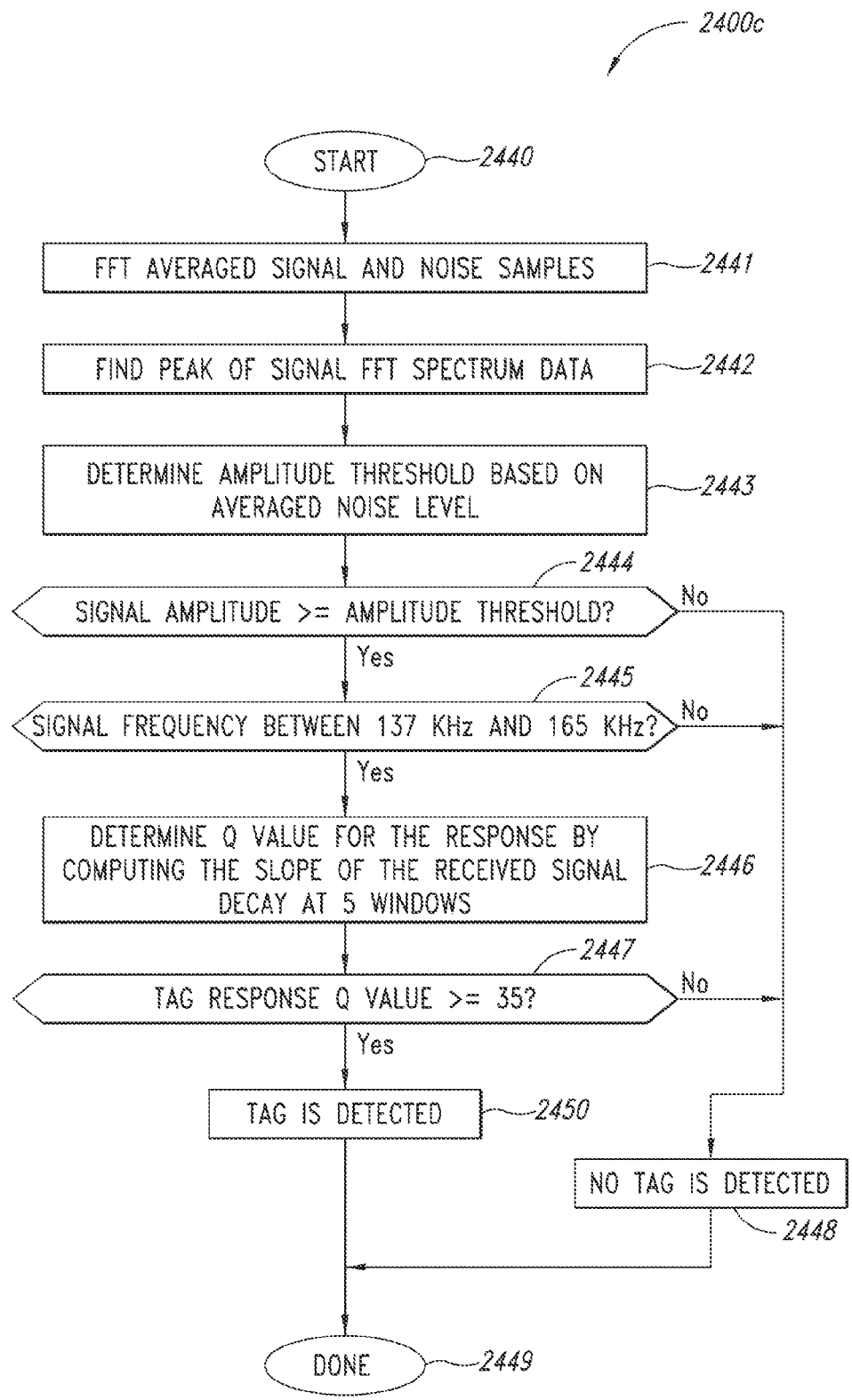
FIG. 24C is a flow diagram of a method of operating an interrogation and detection system to determine whether a transponder has been detected, according to one illustrated embodiment, the method useful with the method of FIG. 24A.

FIG. 24C shows a method of operating an interrogation and detection system to determine whether a transponder has been detected 2400c, according to one illustrated embodiment, the method useful with the method of FIG. 24A.

The method 2400c starts at 2440. For example the method 2400c may start in response to a call from a procedure that implement the method 2400a (FIG. 24A). The method 2400c may, for example, be employed in processing transponder detection 2404 (FIG. 24A).

FIGS. 25A-25E are flow diagrams of methods of operating an interrogation and detection system by measuring and/or compensating for noise, according to various illustrated embodiments, the methods useful with the method of FIG. 24A.

At 2441, the interrogation and detection system transforms the averaged noise and response samples from a time domain to a frequency domain. The interrogation and detection system may, for example, perform fast Fourier transforms on the averaged samples. At 2442, the interrogation and detection system may find a peak of response fast Fourier transformed spectrum data.

At 2443, the interrogation and detection system determines an amplitude threshold based on the averaged noise level. At 2444, the interrogation and detection system determines whether the response amplitude is equal or exceeds the determined amplitude threshold. If so, control passes to 2445. If not, control passes to 2448 where a signal may optionally be produced indicative of no tag being detected.

At 2445, the interrogation and detection system determines whether the signal is in appropriate frequency range. While the frequency range is illustrated as being between 137 KHz and 165 KHz, inclusive, other frequency ranges may be employed depending on the specific structure and frequency of the transponders. The disclosed embodiments are particular suited for use with low Q transponders in which the response frequencies of various transponders are not closely controlled, advantageously allowing large manufacturing tolerances to reduce cost. If the signal is in the appropriate frequency range, control passes to 2446, otherwise control goes to 2448.

At 2446, the interrogation and detection system determines the Q value of the response. For example, the interrogation and detection system may compute the slope of the received signal decay at a number of windows (e.g., 5 windows). At 2450, the interrogation and detection system determines if the determined Q value is greater than or equal to a threshold Q value (e.g., 35). While the threshold Q value is illustrated as being 35, other Q values may be employed depending on the Q value(s) of the specific transponders. If the tag response Q value below the Q value threshold, the interrogation and detection system determines that a transponder has been detected at 2450. If the tag response Q value is equal or above the Q value threshold, the interrogation and detection system determines that a tag has not been detected 2448.

The method 2400c may terminate at 2449, for example until called again by the procedure that implements the method 2400a (FIG. 24A).

Figure 25A:
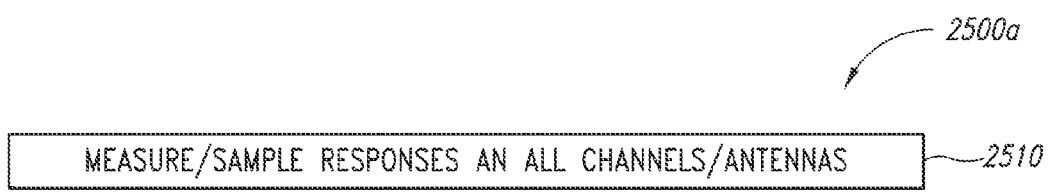
FIGS. 25A-25F are flow diagrams of methods of operating an interrogation and detection system by measuring and/or compensating for noise, according to various illustrated embodiments, the methods useful with the method of FIG. 24A.

FIG. 25A shows a method 2500a of measuring or sampling responses, according to one illustrated embodiment.

In particular, at 2510, the interrogation and detection system measures or samples response on all antennas or antenna channels.

Figure 25B:
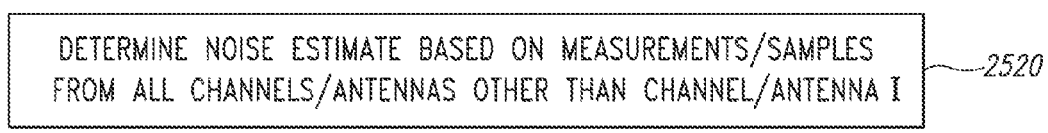

FIG. 25B shows a method 2500b of determining noise estimates, according to one illustrated embodiment.

In particular, at 2520, the interrogation and detection system determines noise estimates based on measures or samples from all antennas or antenna channels other than the respective antenna or antenna channel for which the noise estimate will provide the compensation factors.

Figure 25C:
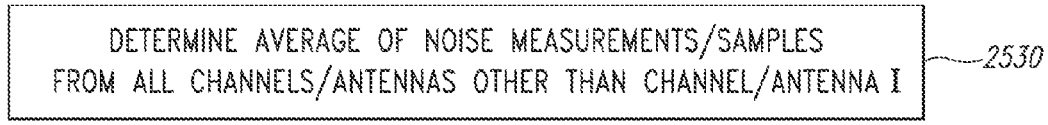

FIG. 25C shows a method 2500c of determining noise estimates, according to one illustrated embodiment.

In particular, at 2530, the interrogation and detection system determines an average noise estimate based on averaging of measures or samples from all antennas or antenna channels other than the respective antenna or antenna channel for which the noise estimate will provide the compensation factors.

Figure 25D:
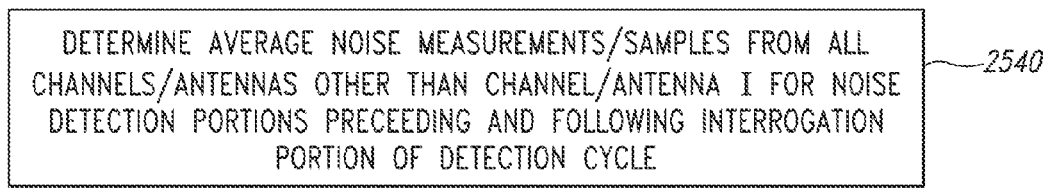

FIG. 25D shows a method 2500d of determining noise estimates, according to one illustrated embodiment.

In particular, at 2540, the interrogation and detection system determines an average noise estimate based on averaging of measures or samples from all antennas or antenna channels other than the respective antenna or antenna channel for which the noise estimate will provide the compensation factors. The averaging includes averaging of noise detection portions which occur both before and after an interrogation portion of a transponder detection cycle. Such allows the interrogation and detection system to essentially determine whether the noise is consistent, periodic, or non-random.

Figure 25E:
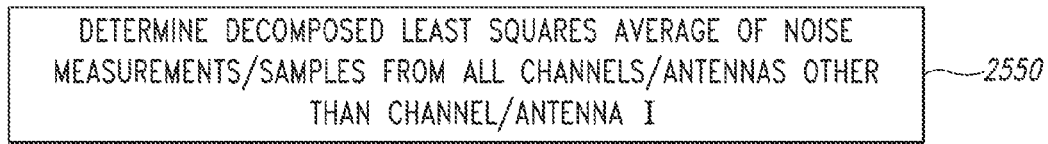

FIG. 25E shows a method 2500e of determining noise estimates, according to one illustrated embodiment.

In particular, at 2550, the interrogation and detection system determines an average noise estimate by determining a decomposed least squares average of noise measurements or samples. While a decomposed least squares approach is illustrated, a wide variety of other approaches may be employed (e.g., Bayesian averaging).

Figure 25F:
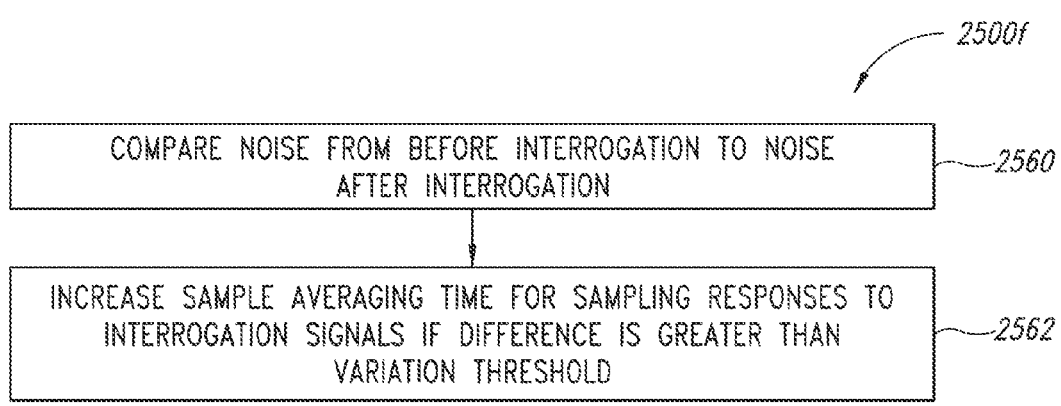

FIG. 25F shows a method 2500f of determining noise estimates, according to one illustrated embodiment.

In particular, at 2560, the interrogation and detection system compares noise measured from before an interrogation portion of the transponder detection to noise measured after the interrogation portion of the transponder detection cycle. A difference between the noise measurements may represent variation in noise. At 2562, the interrogation and detection system may increase the sample averaging time for sampling responses to interrogation signals if a determined difference (i.e., variation in noise) is greater than a variation threshold. Such may allow the interrogation and detection system to accommodate different noise sources, such as those that produce periodic or non-random versus those that produce random noise.

FIG. 26A shows a measured or sampled response 2600a, according to one illustrated embodiment.

The response 2600a in the time domain was measured in an environment which contained a noise source (e.g., fluoroscope) but no transponder. The response 2600a has not be subjected to noise cancellation or adjustment. The amplitude (Y-axis) is in mV, while the time (X-axis) is in µs.

FIG. 26B shows a measured or sampled response 2600b, according to one illustrated embodiment.

The response 2600b is the response 2600a having been subjected to noise cancellation or adjustment. Most of the peaks have noticeably been diminished.

FIG. 26C shows a measured or sampled response 2600c, according to one illustrated embodiment.

The response 2600c is the response 2600a after a fast Fourier transformation to the frequency domain. The amplitude (Y-axis) is in mV, while the time (X-axis) is in frequency. There are three distinctive peaks of noise.

FIG. 26D shows a measured or sampled response 2600d, according to one illustrated embodiment.

The response 2600d is the noise cancelled response 2600b after a fast Fourier transformation to the frequency domain. The peaks have been noticeable diminished, indicating that almost all noise has been removed by the noise cancellation.

Figure 27A:
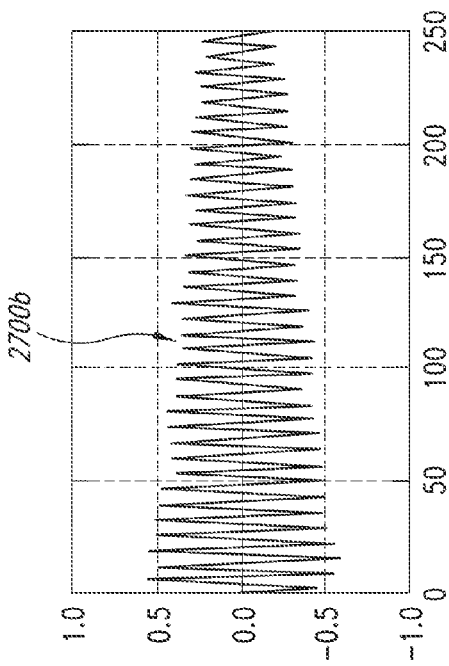
FIG. 27A is a graph showing a measured or sampled response versus time without noise cancellation where a noise source and a transponder are present, according to one illustrated embodiment.

FIG. 27A shows a sampled or measured response 2700a, according to one illustrated embodiment.

The response 2700a in the time domain was measured in an environment which contained a noise source (e.g., fluoroscope) and a transponder. The response 2700a has not be subjected to noise cancellation or adjustment. The amplitude (Y-axis) is in mV, while the time (X-axis) is in µs.

Figure 27B:
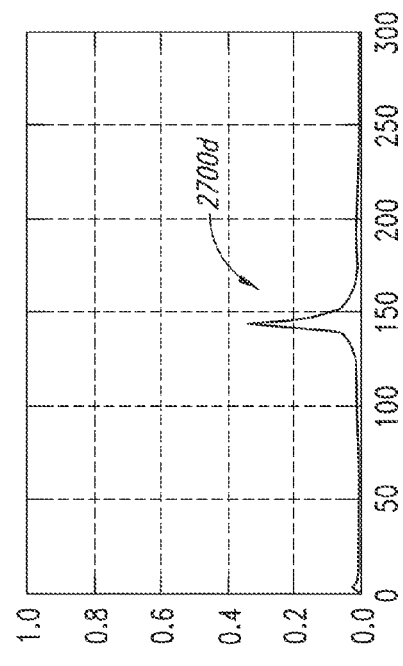
FIG. 27B is a graph showing a measured or sampled response versus time with noise cancellation where a noise source and a transponder are present, according to one illustrated embodiment.

FIG. 27B shows a measured or sampled response 2700b, according to one illustrated embodiment.

The response 2700b is the response 2700a after being subjected to noise cancellation. While many the peaks (associated with noise) have noticeably been diminished, other distinctive peaks remain.

Figure 27C:
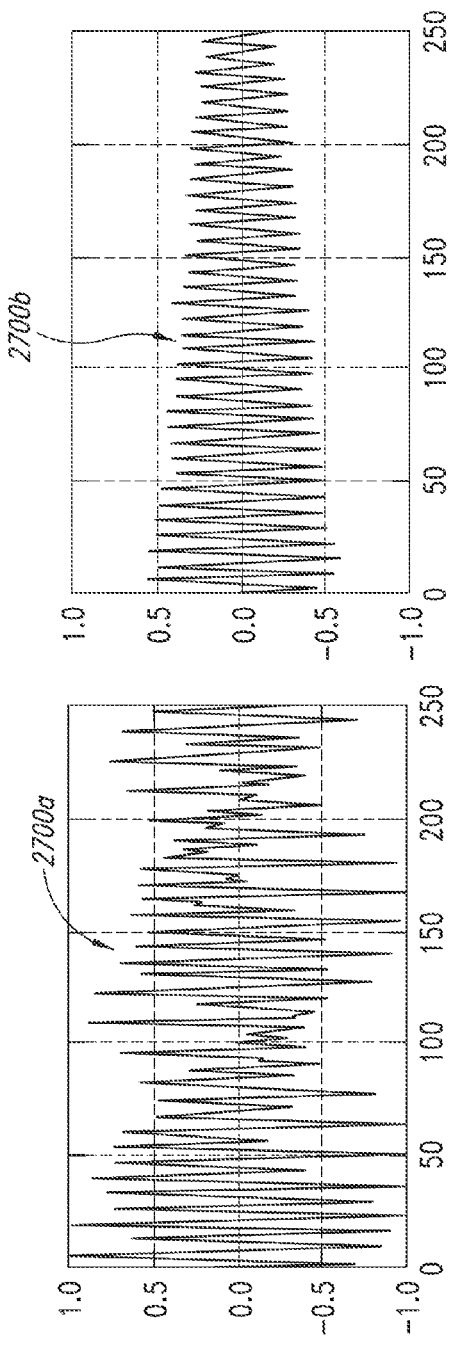
FIG. 27C is a graph showing a measured or sampled response versus frequency without noise cancellation where a noise source and a transponder are present, according to one illustrated embodiment.

FIG. 27C shows a measured or sampled response 2700c, according to one illustrated embodiment.

The response 2700c is the response 2700a after a fast Fourier transformation to the frequency domain. The amplitude (Y-axis) is in mV, while the time (X-axis) is in frequency. There are three distinctive peaks.

Figure 27D:
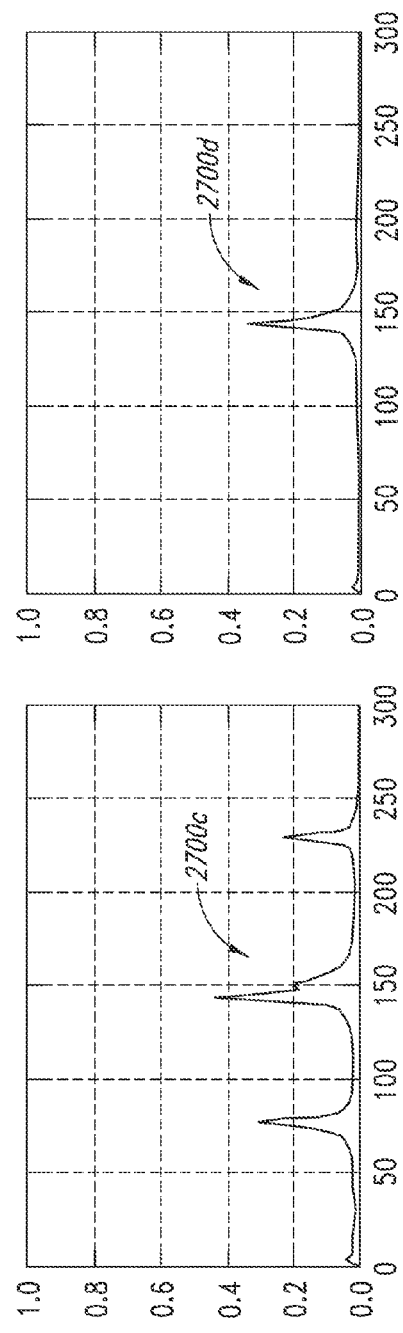
FIG. 27D is a graph showing a measured or sampled response versus frequency with noise cancellation where a noise source and a transponder are present, according to one illustrated embodiment.

FIG. 27D shows a measured or sampled response 2700d, according to one illustrated embodiment.

The response 2700d is the noise cancelled response 2700b after a fast Fourier transformation to the frequency domain. Two of the three peaks have been noticeable diminished, indicating that almost all noise has been removed by the noise cancellation, and leaving a single distinctive peak at the resonant frequency of the transponder.

The above described embodiments may improve a detection range versus noise performance over other more conventional approaches. The embodiment of the present disclosure may be capable of achieving far superior performance, having greater detection range in even mildly noisy environments. Such is particularly advantageous in environments such as operating theaters, and substantially helps reduce false readings (e.g., false positives, false negatives). Thus, such may provide the level of performance demanded by hospitals and doctors.

Thus, during each of a plurality of detection cycles, the interrogation and detection system performs a number of acts or operations. The interrogation and detection system receives unmodulated electromagnetic signals during a noise detection portion of the detection cycle.

The interrogation and detection system determines a noise value indicative of a noise level that corresponds to a highest one of a number N of samples or measurements of the unmodulated electromagnetic signals received during the noise detection portion of the detection cycle, where the number N is greater than one. The interrogation and detection system may determine a noise value indicative of a noise level based at least in part on the unmodulated electromagnetic signals received during the noise detection portion of the detection cycle by setting the noise value based on the highest one of six samples or measurements of the unmodulated electromagnetic signal received during the noise detection portion of the detection cycle. The interrogation and detection system adjusts a signal detection threshold based at least in part on the determined noise value of at least one of the detection cycles. The interrogation and detection system may adjust the signal detection threshold by adjusting the signal detection threshold based at least in part on a first number of determined noise values indicative of a noise level during at least one noise detection portion that occurred before the receive response portion of a first one of the detection cycles and a second number of determined noise values indicative of a noise level during at least one noise detection portion that occurred after the receive response portion of the first one of the detection cycles. The interrogation and detection system may adjust the signal detection threshold based at least in part on the determined noise value of at least one of the detection cycles by adjusting the signal detection threshold to be approximately twice an average of at least one of the first and the second number of determined noise values. The interrogation and detection system may, for example, adjust the signal detection threshold based at least in part on the determined noise value of at least one of the detection cycles by adjusting the signal detection threshold to be approximately twice a greatest one of at least one of the first and the second number of determined noise values.

The interrogation and detection system emits at least one electromagnetic interrogation signal during a transmit portion of the detection cycle. The interrogation and detection system receives unmodulated electromagnetic signals during a receive response portion of the detection cycle that follows the transmit portion of the detection cycle.

The interrogation and detection system determines the presence or absence of a transponder based at least in part on a number M of samples or measurements of the unmodulated electromagnetic signals received during the detection cycle and the adjusted signal detection threshold, where the number M is greater than one. A ratio of N:M may be at least equal to 4. N may be equal to about 200 and M may be equal to about 800. For example, the interrogation and detection system may determine the presence or absence of a transponder by comparing a maximum value of a plurality of matched filter outputs with the adjusted signal threshold.

In some embodiments, the interrogation and detection system determines if an output of at least one matched filter during the noise detection portion of the detection cycle exceeds a noise fault threshold indicative of a noise fault. Such may be employed to prevent extraneous objects (e.g., metal table, EKG leads, etc.) from producing a positive result. For example, the interrogation and detection system may determine if the output of the at least one matched filter during the noise detection portion of the detection cycle exceeds the noise fault threshold for a defined period of time. The interrogation and detection system may then terminate the detection cycle in response to the output of the at least one matched filter exceeding the noise fault threshold for the defined period of time.

The interrogation and detection system may convert the received signal(s) from the time domain to the frequency domain spectrum. Such may be employed, for example in lieu of the match filtering. The interrogation and detection system may, for example, perform a Fourier transform, for instance a fast Fourier transform such as a 256 point fast Fourier transform. Suitable algorithms and/or sets of software code for performing such are available or can be written. The interrogation and detection system may search the frequency domain spectrum to determine the object with the strongest resonance in a defined frequency band. For example, the interrogation and detection system may search the frequency domain spectrum from about 120 KHz to about 175 KHz. An amplitude of the resonant object may be computed as the sum of the resonant power plus and minus 2 fast Fourier transform bins from the peak resonance frequency. This approach may provide a more accurate measurement of power than simply using the peak value. The frequency of the resonant object may be computed using an interpolation approach. This approach may provide a more accurate determination of resonant frequency than simply using the fast Fourier bin number. The interrogation and detection system may determine the presence or absence of a transponder based at least in part on a frequency of the unmodulated electromagnetic signals received during the detection cycle being within a defined frequency range. The defined frequency range may extend from about 137 KHz to about 160 KHz.

The interrogation and detection system may ignore any unmodulated electromagnetic signals received during a recovery portion (if any) of the detection cycle that precedes the receive response portion of the detection cycle. Such may be useful in preventing false positives (i.e., tag detections) from being triggered by the transmission of the interrogation or excitement signals.

The interrogation and detection system may determine a Q value (i.e., Quality factor) of the resonant object from a signal decay slope for the received unmodulated electromagnetic signal(s) returned by the resonant object. For example, the interrogation and detection system may determine a Q value of the unmodulated electromagnetic signals received during the detection cycle being at least equal to a threshold Q value. The threshold Q value may, for example, be 35. The interrogation and detection system may, for example, use multiple windows, for instance five (5) window positions may provide suitable results. The interrogation and detection system may determine the presence or absence of a transponder based at least in part on a Q value of the unmodulated electromagnetic signal(s) received during the detection cycle. The interrogation and detection system may preferably employ the Q value determination in conjunction with determination based on the frequency and on the determination based on the adjusted signal detection threshold.

Consequently, in some embodiments the tag detection may advantageously be based on the received unmodulated electromagnetic signal(s) satisfying all three conditions: 1) measured amplitude is above a threshold, which may be an adjustable threshold, 2) measured frequency is between a lower limit and an upper limit, and 3) measured Q value is above a minimum Q threshold. Interference, for example from RFID tags or EKG cables, are rejected when any of the following three conditions are satisfied: a) measured frequency is below the lower frequency limit, b) measured frequency is above the upper frequency limit, or c) measured Q value is below the threshold Q value. Such may provided significantly superior results over previous approaches, preventing false positives which could otherwise cause a patient to remain open for longer period of time during surgery and tie up hospital personnel and resources.

The above description of illustrated embodiments, particularly the use of multiple antennas, the pulsed wide band frequency hopping with dynamic adjustment of the transmission frequency in the various frequency bands and the use of switched capacitors to achieve such, advantageously permit the use of inexpensive transponders which are not accurately tuned to a chosen or selected resonant frequency. This is in marked contrast to the approach typically taken with other types of resonant transponders (i.e., transponders without memory). Such approaches typically interrogate or excite the resonant transponder using narrow frequency bands centered closely on specific frequencies, to achieve a selected resonant response from a highly accurate transponder in order to differentiate signal from noise. This is also in marked contrast to the approach typically taken with radio frequency identification (RFID) tags whether active or passive, which also typically employ are narrow band to achieve a selected response from a highly accurate RFID tag.

Figure 28:
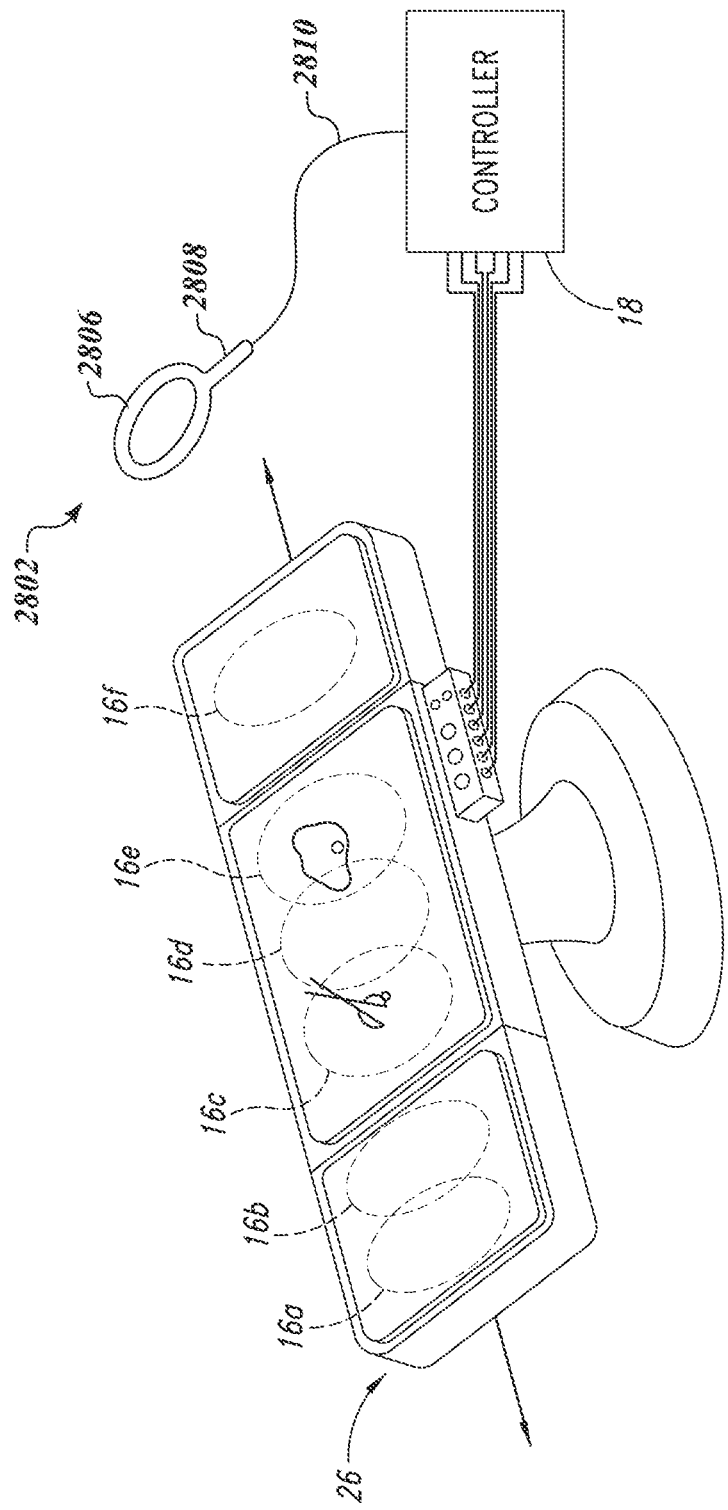
FIG. 28 is an isometric view of a surgical environment including an operating table that carries a plurality of antennas, a hand held wand antenna, and a controller according to one illustrated embodiment.

The interrogation and detection system herein described may further implement a handheld wand 2802 as illustrated in FIG. 28. Wand 2802 comprises a loop antenna 2806, a handle 2808, and a cord 2810. The wand 2802 may be configured to interface with the interrogation and detection system. The wand 2802 may be connected to the controller 18 by means of the chord 2810. The wand 2802 may be waved over the patient on the patient support structure 26 while emitting an interrogation signal to excite any transponder 24 which may be in or near the patient. The antennas 16a-16f may then all be used to detect a signal from the transponder as previously described. In one embodiment the controller 18 controls the wand 2802. In one embodiment the wand 2802 emits an interrogation signal and monitors for a response from a transponder 24. In one embodiment the wand 2802 operates independent of the antennas 16 and the controller 18. In one embodiment the wand 2802 is wirelessly operated. In one embodiment the wand 2802 only detects a transponder and does not emit an interrogation signal. Many other implementations of the wand 2802 will be apparent to those of skill in the art in light of the illustrated embodiments. For example, the wand 2802 may be implemented in a form other than a loop antenna. The illustrated embodiments are given only by way of non-limiting example.

The above description of illustrated embodiments, including what is described in the Abstract, is not intended to be exhaustive or to limit the embodiments to the precise forms disclosed. Although specific embodiments of and examples are described herein for illustrative purposes, various equivalent modifications can be made without departing from the spirit and scope of the disclosure, as will be recognized by those skilled in the relevant art. The teachings provided herein of the various embodiments can be applied to other transponders and interrogation and detection systems, not necessarily the exemplary surgical object transponders and interrogation and detection systems generally described above.

For instance, the foregoing detailed description has set forth various embodiments of the devices and/or processes via the use of block diagrams, schematics, and examples.

Insofar as such block diagrams, schematics, and examples contain one or more functions and/or operations, it will be understood by those skilled in the art that each function and/or operation within such block diagrams, flowcharts, or examples can be implemented, individually and/or collectively, by a wide range of hardware, software, firmware, or virtually any combination thereof. In one embodiment, the present subject matter may be implemented via Application Specific Integrated Circuits (ASICs). However, those skilled in the art will recognize that the embodiments disclosed herein, in whole or in part, can be equivalently implemented in standard integrated circuits, as one or more computer programs running on one or more computers (e.g., as one or more programs running on one or more computer systems), as one or more programs running on one or more controllers (e.g., microcontrollers) as one or more programs running on one or more processors (e.g., microprocessors), as firmware, or as virtually any combination thereof, and that designing the circuitry and/or writing the code for the software and or firmware would be well within the skill of one of ordinary skill in the art in light of this disclosure.

In addition, those skilled in the art will appreciate that the mechanisms of taught herein are capable of being distributed as a program product in a variety of forms, and that an illustrative embodiment applies equally regardless of the particular type of physical signal bearing media used to actually carry out the distribution. Examples of signal bearing media include, but are not limited to, the following: recordable type media such as floppy disks, hard disk drives, CD ROMs, digital tape, and computer memory.

The various embodiments described above can be combined to provide further embodiments. To the extent not inconsistent with the teachings herein, all U.S. patents, U.S. patent application publications, U.S. patent applications, foreign patents, foreign patent applications and non-patent publications commonly owned with this patent application and referred to in this specification and/or listed in the Application Data Sheet including: U.S. Patent Publication No. US 2004/0250819, published Dec. 16, 2004; U.S. Provisional Patent Application No. 60/811,376 filed Jun. 6, 2006; U.S. Provisional Patent Application No. 61/109,104 filed Oct. 28, 2008; U.S. Provisional Patent Application No. 61/222,443 filed Jul. 1, 2009; U.S. Provisional Patent Application No. 61/222,847 filed Jul. 2, 2009; U.S. Provisional Patent Application No. 61/242,699, filed Sep. 15, 2009; U.S. provisional patent application Ser. No. 61/242,704 filed Sep. 15, 2009; U.S. Non-Provisional patent application Ser. No. 11/743,104 filed May 1, 2007; U.S. Non-Provisional patent application Ser. No. 12/472,199 filed May 26, 2009; U.S. Non-Provisional patent application Ser. No. 12/473,059 filed May 27, 2009; and U.S. Pat. No. 6,026,818, issued Feb. 22, 2000, are incorporated herein by reference, in their entirety. Aspects of the embodiments can be modified, if necessary to employ concepts of the various patents, applications and publications to provide yet further embodiments.

These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An apparatus to detect transponder tagged objects which are used in performing medical procedures, the apparatus comprising:

a plurality of antennas spaced at fixed positions along at least a portion of a length of a patient support structure that is sized to support a patient, at least one of the antennas having a measurable physical characteristic that varies in response to a physical force applied to the at least one of the antennas; and a control system communicatively coupled to the antennas to activate respective ones of at least two of the antennas to transmit respective interrogation signals, to detect a response signal generated by a transponder responsive to the interrogation signals, and to detect a value indicative of the measurable physical characteristic that varies in response to the physical force applied to the at least one of the antenna.

2. The apparatus of claim 1 wherein the measurable physical characteristic that varies in response to a physical force applied to the at least one of the antennas is a resistance of the antenna, which indicates an amount of strain at the position of the antenna on the patient support structure.

3. The apparatus of claim 1 wherein a number of the plurality of antennas are electrically coupled in at least one bridge configuration.

4. The apparatus of claim 3 wherein the at least one bridge configuration is a Wheatstone bridge configuration.

5. The apparatus of claim 1 wherein the control system further provides an alert in response to the measurable physical characteristic exceeding a threshold value.

6. The apparatus of claim 5 wherein the control system further provides an indication of a location on the patient support structure where the measurable physical characteristic has exceeded the threshold value.

7. The apparatus of claim 1 wherein the value indicative of the measurable physical characteristic is indicative of at least one of an amount of strain, an amount of force or an amount of pressure.

8. The apparatus of claim 1 wherein the patient support structure comprises a surgical table or a bed.

9. The apparatus of claim 1 wherein the control system sequentially activates respective ones of the antennas to transmit respective interrogation signals and detects via the antennas other than a most recently activated one of the antennas the response signal generated by the transponder responsive to a most recent one of the interrogation signals.

10. A method to detect transponder tagged objects which are used in performing medical procedures, the method comprising:

for a plurality of antennas spaced at fixed positions along at least a portion of a length of a patient support structure that is sized to support a patient,
  activating respective ones of at least two of the antennas to transmit respective interrogation signals,
  detecting through the antennas a response signal generated by a transponder responsive to the interrogation signals, and
  detecting a measurable physical characteristic that varies in response to a physical force applied to at least one of the plurality of antennas.

11. The method of claim 10 wherein detecting a measurable physical characteristic that varies in response to a physical force applied to the at least one of the plurality of antennas comprises detecting a change in a resistance of each antenna.

12. The method of claim 10 further comprising providing an alert in response to a value of the detected measurable physical characteristic equaling or exceeding a threshold value.

13. The method of claim 12 further comprising providing an indication of a location on the patient support structure where the value of the detected measurable physical characteristic has equaled or exceeded the threshold value.

14. The method of claim 10 wherein detecting a measurable physical characteristic that varies in response to a physical force applied to the at least one of the plurality of antennas comprises detecting a physical characteristic indicative of at least one of a strain, a force or a pressure applied to the antenna.

15. The method of claim 10 wherein activating respective ones of at least two of the antennas to transmit respective interrogation signals and detecting through the antennas a response signal generated by a transponder responsive to the interrogation signals comprises sequentially activating respective ones of the antennas to transmit respective interrogation signals and detecting via the antennas other than a most recently activated one of the antennas the response signal generated by the transponder responsive to a most recent one of the interrogation signals.

\* \* \* \* \*